United States Patent
Southwell et al.

(10) Patent No.: US 10,533,172 B2
(45) Date of Patent: Jan. 14, 2020

(54) ALLELE-SPECIFIC THERAPY FOR HUNTINGTON DISEASE HAPLOTYPES

(71) Applicant: The University of British Columbia, Vancouver (CA)

(72) Inventors: Amber L. Southwell, Vancouver (CA); Christopher Kay, Vancouver (CA); Michael R. Hayden, Vancouver (CA); Nicholas S. Caron, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/512,013

(22) PCT Filed: Sep. 18, 2015

(86) PCT No.: PCT/CA2015/000501
§ 371 (c)(1),
(2) Date: Mar. 16, 2017

(87) PCT Pub. No.: WO2016/041058
PCT Pub. Date: Mar. 24, 2016

(65) Prior Publication Data
US 2017/0253877 A1 Sep. 7, 2017

Related U.S. Application Data

(60) Provisional application No. 62/191,144, filed on Jul. 10, 2015, provisional application No. 62/052,282, filed on Sep. 18, 2014.

(51) Int. Cl.
*C12N 15/113* (2010.01)
*C12N 5/00* (2006.01)

(52) U.S. Cl.
CPC ........ *C12N 15/113* (2013.01); *C12N 2310/11* (2013.01); *C12N 2310/315* (2013.01); *C12N 2310/3125* (2013.01); *C12N 2310/3181* (2013.01); *C12N 2310/321* (2013.01); *C12N 2310/3231* (2013.01); *C12N 2310/3233* (2013.01); *C12N 2310/341* (2013.01); *C12N 2320/34* (2013.01)

(58) Field of Classification Search
None
See application file for complete search history.

(56) References Cited

U.S. PATENT DOCUMENTS 7,795,419 B2 9/2010 Bentwich et al.
2006/0270623 A1 11/2006 McSwiggen

FOREIGN PATENT DOCUMENTS

WO 2011/054939 A2 5/2011
WO 2012/177639 A2 12/2012

OTHER PUBLICATIONS

NCBI dbSNP Short Genetic Variantions, Mar. 11, 2011 [database online], RefSNP (rs#) rs72239206, http://www.ncbi.nlm.nig.gov/projects/SNP/snp_ref.cgi?rs=72239206> [retrieved Jan. 4, 2016], 1 page.
Kay, C., et al., "Huntingtin Haplotypes Provide Prioritized Target Panels for Allele-Specific Silencing in Huntington Disease Patients of European Ancestry," Molecular Therapy 23(11):1759-1771, Nov. 2015.
Khvorova, A., et al., "SiRNA Molecules Targeting Bcl-2," Sequence 180547, *Homo sapiens*, submitted Aug. 18, 2010, <http://ibis.internal.epo.org/exam/dbfetch.jsp?id+EM_PAT:HD303831> [retrieved Nov. 12, 2017], 1 page.
Lee, J.-M., et al., "Common SNP-Based Haplotype Analysis of the 4p16.3 Huntington Disease Gene Region," American Journal of Human Genetics 90(3):434-444, Mar. 2012.
Partial Supplementary European Search Report dated Jan. 4, 2018, issued in European Application No. 15841286.6, filed Sep. 18, 2015, 15 pages.
Pfister, E.L., et al., "Five siRNAs Targeting Three SNPs in Huntingtin May Provide Therapy for Three-Quarters of Huntington's Disease Patients," Current Biology 19(9):774-778, May 2009. (Author Manuscript provided, PMCID:PMC2746439, available in PMC Nov. 12, 2009, 11 pages.).
Knauert, M.P., and P.M. Glazer, "Triplex Forming Oligonucleotides: Sequence-Specific Tools for Gene Targeting," Human Molecular Genetics 10(20):2243-2251, Oct. 2001.
Nishina, K., et al., "DNA/RNA Heteroduplex Oligonucleotide for Highly Efficient Gene Silencing," Nature Communications 6:7969, Aug. 2015, 13 pages.
Offord, C., "Oligonucleotide Thereapuetucs Near Approval," The Scientist Magazine, Dec. 2016, 6 pages.
Straarup, E.M., et al., "Short Locked Nucleic Acid Antisense Oligonucleotides Potently Reduce Apolipoprotein B mRNA and Serum Cholesterol in Mice and Non-Human Primates," Nucleic Acids Research 38(20):7100-7111, Jul. 2010.
Watts, J.K., and D.R. Corey, "Gene Silencing by siRNAs and Antisense Oligonucleotides in the Labratory and the Clinic," J Pathol. 226(2):365-379, Jan. 2012 (author manuscript available Feb. 2014).

*Primary Examiner* — Sean McGarry
(74) *Attorney, Agent, or Firm* — Christensen O'Connor Johnson Kindness PLLC

(57) ABSTRACT

The present invention relates to compositions and methods of use thereof for inhibiting mutant HTT mRNA transcription or CAG-expanded HTT protein expression in a cell, comprising contacting the cell with an effective amount of an oligomer targeting a differentiating polymorphism, wherein the differentiating polymorphism is selected from rs72239206, rs363107, rs362313, rs2530595, rs113407847. Specific oligomer sequences are also provided.

34 Claims, 9 Drawing Sheets
Specification includes a Sequence Listing.

|  | n | One Target | | | | Two Targets | | | Three Targets | |
|---|---|---|---|---|---|---|---|---|---|---|
|  |  | A1 | A2 | A3a | A | A1+A2 | A1+A | A2+A | A1+A2+A3a | A1+A2+A |
| Canadian | 283 | 44% | 24% | 10% | 48% | 68% | 66% | 55% | 78% | 73% |
| Swedish | 51 | 47% | 18% | 27% | 51% | 65% | 69% | 59% | 92% | 76% |
| French | 53 | 43% | 21% | 23% | 55% | 64% | 75% | 58% | 87% | 79% |
| Italian | 67 | 15% | 43% | 5% | 27% | 58% | 37% | 48% | 63% | 58% |
| Average |  | 37% | 27% | 16% | 45% | 64% | 62% | 55% | 80% | 72% |

Haplotype heterozygosity in HD patients from each cohort, with the target haplotype phased to expanded CAG.

ALLELE-SPECIFIC THERAPY FOR HUNTINGTON DISEASE HAPLOTYPES

CROSS REFERENCE TO RELATED APPLICATIONS

This application claims the benefit of U.S. Provisional Patent Application Ser. Nos. 62/052,282 filed on 18 Sep. 2014 and 62/191,144 filed on 10 Jul. 2015, both entitled "ALLELE-SPECIFIC THERAPY FOR HUNTINGTON DISEASE HAPLOTYPES".

FIELD OF INVENTION

The present invention relates to methods and compositions for the treatment of Huntington's disease (HD) by allele-specific HTT silencing suitable for the majority of HD patients, via haplotype-specific targeting of mutant HTT in these populations. The present invention further provides potent, selective silencing of the mutant transcript using nucleic acid silencing agents.

BACKGROUND

Huntington disease (HD, [MIM 143100]) is a monogenic movement disorder that is caused by an expanded CAG repeat in exon 1 of the Huntingtin gene (HTT) and is molecularly defined by more than 35 tandem CAG triplets in one copy of the HTT gene [1-3]. Expanded CAG triplets encode similarly repetitive glutamine residues in the HTT protein, leading to multiple downstream pathogenic effects and selective neuropathology [4]. The defined genetic cause of HD, and its consequent gain-of-function toxicity, allow for the suppression of HTT as a therapeutic strategy [5]. Multiple preclinical studies have shown reversal of HD phenotypes by inducible or exogenous silencing of transgenic mutant HTT [6-9]. However, reagents which silence both wild-type HTT and mutant HTT may have detrimental long-term consequences in humans. Constitutive loss of the murine homolog Hdh is embryonic lethal and postnatal repression of Hdh leads to neurodegenerative phenotypes, suggesting a crucial role for HTT in development and adulthood [10-13]. Wild-type HTT has also been shown to be protective against toxic effects of mutant HTT in a dose-dependent manner. The preferential silencing of mutant HTT, and preservation of normal wild-type HTT expression, may minimize loss-of-function effects and yield greater therapeutic benefit than total HTT suppression.

There are two classes of genetic targets which can be used to selectively suppress mutant HTT versus its normal counterpart: the expanded CAG repeat and polymorphisms linked with the pathogenic mutation [14]. The utility of both classes of targets is informed by genetic diversity at the HTT locus in a given patient population [15]. The CAG repeat is intrinsically polymorphic, and the ability to achieve pharmacological discrimination between expanded and normal CAG diminishes with decreasing size difference between the two repeats [16, 17]. In contrast, polymorphism—targeted or SNP-targeted silencing of mutant HTT has achieved potent reduction of mutant HTT with negligible effect on expression of normal HTT transcript by acting to degrade a mutant transcript bearing a specific target allele [18, 19]. Careful structure-activity studies of antisense oligonucleotides (ASOs) suggest that suppression of normal HTT may be avoided with SNP-targeted reagents given appropriate preclinical screens [19, 20].

A crucial question in the development of SNP-targeted reagents is the choice of allele target for maximum therapeutic benefit in the HD patient population. The time and cost of drug development requires clear prioritization of targets for allele-specific HTT silencing in the greatest proportion of patients. Heterozygosity of various target SNPs has been evaluated in local patient cohorts, but few phased estimates are available across diverse patient groups to guide development of allele-specific reagents. For example, the Δ2642 codon deletion present in exon 58 of HTT has been targeted for selective HTT silencing in vitro by siRNA [21], but the frequency of this polymorphism among HD chromosomes varies from 59% in an American cohort [22] to 18.6% in Italy [23]. No study has examined the phased heterozygosity and haplotype relationship of all potential targets, and it remains unclear which HTT polymorphism would offer treatment for the greatest number of patients worldwide.

SUMMARY

The present invention is based, in part, on the identification of polymorphisms associated with HD haplotypes, which may be targeted to preferentially silence the CAG-expanded mutant huntingtin gene. The present invention provides methods and compositions for the treatment of HD.

Provided herein is an efficient and useful panel of targets for allele-specific HTT silencing in the greatest number of HD patients of European ancestry to enable rational, haplotype-specific targeting of mutant HTT in these populations. In part, the present invention further provides potent, selective silencing of the mutant transcript using nucleic acid silencing agents.

In a first aspect, there is a method of reducing the expression of mutant HTT in a cell, including contacting the cell with an effective amount of a nucleic acid silencing agent that targets a specific HD haplotype.

In a further aspect of the invention, there is provided a method of selecting a nucleic acid silencing agent that targets a specific haplotype, including obtaining a nucleic acid sample from the subject; identifying one or more allele-specific polymorphisms in the nucleic acid sample; selecting a nucleic acid silencing agent comprising a sequence that preferentially targets the specific HD haplotype.

In a further aspect of the invention, there is provided a method of reducing the expression of mutant HTT in a subject, including obtaining a nucleic acid sample from the subject; identifying one or more than one allele-specific polymorphisms in the nucleic acid sample; selecting one or more than one nucleic acid silencing agents comprising a sequence that preferentially targets alleles on the specific HD haplotype; and administering to the subject an effective amount of the one or more than one nucleic acid silencing agent.

In a further aspect, there is provided an oligomer of between 10-30 nucleobases in length which includes a contiguous nucleotide sequence of a total of between 10-26 nucleotides, wherein the continuous nucleotide sequence is targeted to hybridize to a sequence selected from the group consisting of:

(SEQ ID NO: 522)
5'-TGACAGTTGTATTTTTGTTTGTGACACGTATTATCTGTTAAAACA

TTTTC-3';

(SEQ ID NO: 523)
5'-TCTTAAACTTTTAAATGCCATTTGATCTTTGAAAATATATGTTTTA

ATAGTGTATTTTAAG-3';

(SEQ ID NO: 524)
5'-CCCTCAGCGAGCAAGTCAAGCTCTTCACAGTGATGTCTTACA

AGCGCAGAGGGCTCTGTGA-3';

(SEQ ID NO: 525)
5'-GCTTTGTCCCTCCCCCGCTTCCTCCCTCTGTGGGGAGGACCC

GGGACCACAGCTGCTGGCC-3';
and (SEQ ID NO: 526)
5'-GGAGAGACTCCACTCTGAATGGGGCCGGGAGGTGGGGAGGA

CTCCATTTCAGATGGGGTCG-3';

wherein the oligomer targets the bolded nucleotide(s), permits between 0-3 mismatches and reduces mutant Huntingtin (HTT) mRNA or mutant HTT protein in a cell or tissue.

In a further aspect, there is provided an oligomer of between 10-30 nucleobases in length and hybridizes to a sequence selected from the group consisting of:

(SEQ ID NO: 522)
5'-TGACAGTTGTATTTTTGTTTGTGACACGTATTATCTGTTAAAAC

ATTTTC-3';

(SEQ ID NO: 523)
5'-TCTTAAACTTTTAAATGCCATTTGATCTTTGAAAATATATGTTTT

AATAGTGTATTTTAAG-3';

(SEQ ID NO: 524)
5'-CCCTCAGCGAGCAAGTCAAGCTCTTCACAGTGATGTCTTACA

AGCGCAGAGGGCTCTGTGA-3';

(SEQ ID NO: 525)
5'-GCTTTGTCCCTCCCCCGCTTCCTCCCTCTGTGGGGAGGACC

CGGGACCACAGCTGCTGGCC-3';
and (SEQ ID NO: 526)
5'-GGAGAGACTCCACTCTGAATGGGGCCGGGAGGTGGGGAGG

ACTCCATTTCAGATGGGGTCG-3';

wherein the oligomer targets the bolded nucleotide(s), and reduces mutant Huntingtin (HTT) mRNA or mutant HTT protein in a cell or tissue.

In a further aspect, there is provided an oligomer of between 10-30 nucleobases in length and hybridizes to a sequence selected from the group consisting of:

(SEQ ID NO: 522)
5'-TGACAGTTGTATTTTTGTTTGTGACACGTATTATCTGTTAAAAC

ATTTTC-3';

(SEQ ID NO: 523)
5'-TCTTAAACTTTTAAATGCCATTTGATCTTTGAAAATATATGTTTT

AATAGTGTATTTTAAG-3';

(SEQ ID NO: 524)
5'-CCCTCAGCGAGCAAGTCAAGCTCTTCACAGTGATGTCTTACA

AGCGCAGAGGGCTCTGTGA-3';

(SEQ ID NO: 525)
5'-GCTTTGTCCCTCCCCCGCTTCCTCCCTCTGTGGGGAGGACC

CGGGACCACAGCTGCTGGCC-3';
and (SEQ ID NO: 526)
5'-GGAGAGACTCCACTCTGAATGGGGCCGGGAGGTGGGGAGG

ACTCCATTTCAGATGGGGTCG-3';

wherein the oligomer targets the bolded nucleotide(s).

In a further aspect, there is provided an oligomer of between 10-30 nucleobases in length and hybridizes to a sequence selected from the group consisting of:

(SEQ ID NO: 522)
5'-TGACAGTTGTATTTTTGTTTGTGACACGTATTATCTGTTAA

AACATTTTC-3';

(SEQ ID NO: 523)
5'-TCTTAAACTTTTAAATGCCATTTGATCTTTGAAAATATATGTT

TTAATAGTGTATTTTAAG-3';

(SEQ ID NO: 524)
5'-CCCTCAGCGAGCAAGTCAAGCTCTTCACAGTGATGTCTTAC

AAGCGCAGAGGGCTCTGTGA-3';

(SEQ ID NO: 525)
5'-GCTTTGTCCCTCCCCCGCTTCCTCCCTCTGTGGGGAGGAC

CCGGGACCACAGCTGCTGGCC-3';
and (SEQ ID NO: 526)
5'-GGAGAGACTCCACTCTGAATGGGGCCGGGAGGTGGGGAGG

ACTCCATTTCAGATGGGGTCG-3';

wherein the oligomer reduces mutant Huntingtin (HTT) mRNA or mutant HTT protein in a cell or tissue.

In a further aspect, there is provided a pharmaceutical composition including the oligomer described herein and a pharmaceutically acceptable diluent, carrier, salt or adjuvant.

In a further aspect, there is provided a method of reducing mutant Huntingtin (HTT) mRNA or mutant HTT protein in a cell or tissue, including contacting the cell or tissue with an effective amount of an oligomer targeting a differentiating polymorphism, wherein the differentiating polymorphism is selected from rs72239206, rs363107, rs362313, rs2530595, rs113407847.

In a further aspect, there is provided a method of reducing mutant Huntingtin (HTT) mRNA or mutant HTT protein in a cell or tissue, including contacting the cell or tissue with an effective amount of an oligomer described herein or a pharmaceutical composition described herein.

In a further aspect, there is provided a method of treating Huntington Disease (HD) in a mammal, including administering to the mammal an effective amount of an oligomer targeting a differentiating polymorphism, wherein the differentiating polymorphism is selected from rs72239206, rs363107, rs362313, rs2530595, rs113407847.

In a further aspect, there is provided a method of treating a Huntington Disease (HD) in a mammal, comprising administering to the mammal an effective amount of an oligomer described herein; or a pharmaceutical composition described herein; wherein the mammal is currently suffering from or at risk of suffering from HD.

In a further aspect, there is provided a use of an oligomer described herein in the preparation of a medicament for the treatment of HD.

In a further aspect, there is provided a use of an oligomer for the treatment of HD, wherein the oligomer targets a differentiating polymorphism, wherein the differentiating polymorphism is selected from rs72239206, rs363107, rs362313, rs2530595, rs113407847.

In a further aspect, there is provided a use of an oligomer described herein for the treatment of HD.

In a further aspect, there is provided a use of a pharmaceutical composition described herein for the treatment of HD.

In a further aspect, there is provided an oligomer described herein for use in the treatment of HD.

In a further aspect, there is provided a commercial package, comprising: an oligomer described herein; and instructions for the treatment of HD.

In a further aspect, there is provided an oligomer wherein the oligomer is selected from the group consisting of:

```
5'-G*A*T*A*A*t*a*c*g*t*g*t*c*a*C*A*A*A*C-3';

5'-A*T*A*A*T*a*c*g*t*g*t*c*A*C*A*A*A-3';

5'-T*A*A*T*a*c*g*t*g*t*c*A*C*A*A-3';

5'-A*T*A*A*t*a*c*g*t*g*t*c*a*C*A*A*A-3';

5'-T*A*T*A*t*t*t*t*c*a*a*a*g*A*T*C*A-3';

5'-A*A*G*A*c*a*t*c*a*c*t*g*t*G*A*A*G-3'

5'-T*C*C*T*c*c*c*c*a*c*a*g*a*G*G*G*A-3';
and

5'-C*T*C*C*c*c*a*c*c*t*c*c*c*G*G*C*C-3'.
``` wherein capital letters represent LNA monomers, lower case letters represent DNA monomers and "*" represents a phosphorothioate linkage group between the monomers.

In a further aspect, there is provided a oligomer having a sequence selected from the group consisting of:

```
                                    (SEQ ID NO: 36)
       5'-GATAATACGTGTCACAAAC-3';

1 (SEQ ID NO: 66)
       5'-ATAATACGTGTCACAAA-3';

(SEQ ID NO: 92)
       5'-TAATACGTGTCACAA-3';

(SEQ ID NO: 163)
       5'-TATATTTTCAAAGATCA-3';

(SEQ ID NO: 268)
       5'-AAGACATCACTGTGAAG-3';

(SEQ ID NO: 373)
       5'-TCCTCCCCACAGAGGGA-3';
       and (SEQ ID NO: 478)
       5'-CTCCCCACCTCCCGGCC-3';
``` wherein the oligomer reduces mutant Huntingtin (HTT) mRNA or mutant HTT protein in a cell or tissue.

The HD haplotype may be the A1, A2 or the A3a haplotype. The allele-specific polymorphism may be selected from the group consisting of rs72239206, rs363107, rs362313, rs2530595 or rs113407847.

The oligomer may be an antisense oligonucleotide. The oligomer may be selected from the group comprising SEQ ID NO: 6-517 or a fragment thereof. The oligomer may be 10 to 30, 10 to 14, 12 to 25, 15 to 25, or 18 to 24 nucleotides in length. The subject or patient may have a European or Caucasian marker as described herein.

The oligomer may be selected from SEQ ID NOs: 6-10. The oligomer may be selected from SEQ ID NOs: 11-517. The oligomer may have a sequence selected from the group consisting of:

```
                                    (SEQ ID NO: 36)
       5'-GATAATACGTGTCACAAAC-3';

(SEQ ID NO: 66)
       5'-ATAATACGTGTCACAAA-3';

(SEQ ID NO: 92)
       5'-TAATACGTGTCACAA-3';

(SEQ ID NO: 163)
       5'-TATATTTTCAAAGATCA-3';

(SEQ ID NO: 268)
       5'-AAGACATCACTGTGAAG-3';

(SEQ ID NO: 373)
       5'-TCCTCCCCACAGAGGGA-3';
       and (SEQ ID NO: 478)
       5'-CTCCCCACCTCCCGGCC-3'.
```

The oligomer may include nucleotide analogues. The oligomer may include a modified internucleoside linkage. The modified internucleoside linkage may be a peptide-nucleic acid linkage, a morpholino linkage, a N3' to P5' phosphoramidate linkage, a methylphosphonate linkage or a phosphorothioate linkage. The oligomer may have one or more modified sugar moieties. The modified sugar moiety may be 2'-O-alkyl oligoribonucleotide. The oligomer may be a gapmer. The oligomer may have a 2'MOE gapmer modification. The oligomer may have a modified nucleobase. The modified nucleobase may be a 5-methyl pyrimidine or a 5-propynyl pyrimidine. The one or more nucleotide analogues may include a locked nucleic acid (LNA). The LNA units include beta-D-oxy-LNA monomers. The cell may be within a tissue of a mammal. The mammal may be a human.

The ASO may further include a modified internucleoside linkage. The modified internucleoside linkage may be a peptide-nucleic acid linkage, a morpholino linkage, a N3' to P5' phosphoramidate linkage, a methylphosphonate linkage or a phosphorothioate linkage. The ASO may further include a modified sugar moiety. The modified sugar moiety may be a 2'-O-alkyl oligoribonucleotide. The ASO may further have a 2'MOE gapmer modification. The ASO may further have a 2'OMe gapmer modification. The ASO may further include a modified nucleobase. The modified nucleobase may be a 5-methyl pyrimidine or a 5-propynyl pyrimidine.

This summary of the invention does not necessarily describe all features of the invention. Other aspects, features and advantages of the present invention will become apparent to those of ordinary skill in the art upon review of the following description of specific embodiments of the invention.

BRIEF DESCRIPTION OF THE FIGURES

FIG. 10 is a table illustrating haplotype heterozygosity in HD patients from each cohort, with the target haplotype phased to expanded CAG.

DETAILED DESCRIPTION

Figure 1:
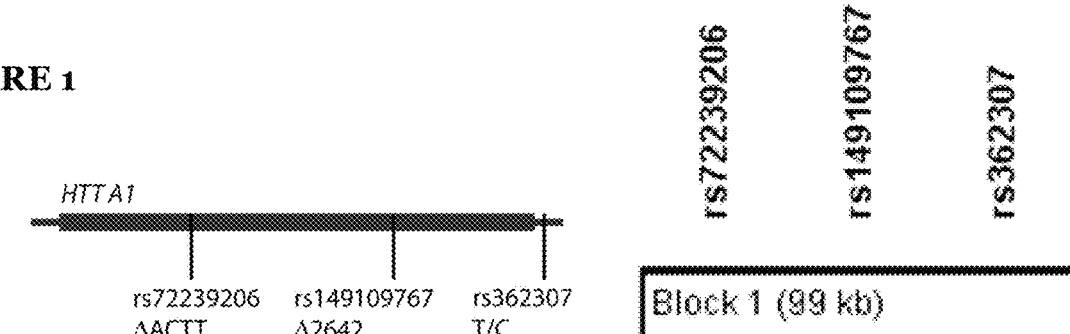
FIG. 1(a) The most common HD haplotype, A1, is uniquely defined by three transcribed polymorphisms in high pairwise linkage disequilibrium across HTT. The 4 bp indel rs72239206 represents a novel polymorphism associated with the CAG expansion. (b) The second most common HD haplotype, A2, is defined by five intragenic SNPs. Three of these polymorphisms (rs363107, rs362313, and rs2530595) represent novel HD-associated polymorphisms. (c) HD-associated A3a, the third most common HD haplotype, is specifically marked by the novel SNP rs113407847. Right panels in (a) and (b) show pairwise LD plot ($r^2$) of A1 and A2 haplotype-defining polymorphisms as calculated from 700 phased haplotypes of European Caucasians.
Figure 1:
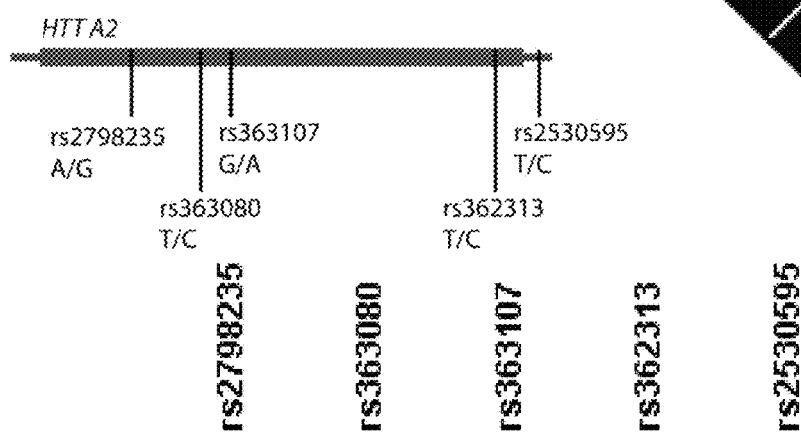
Figure 1:
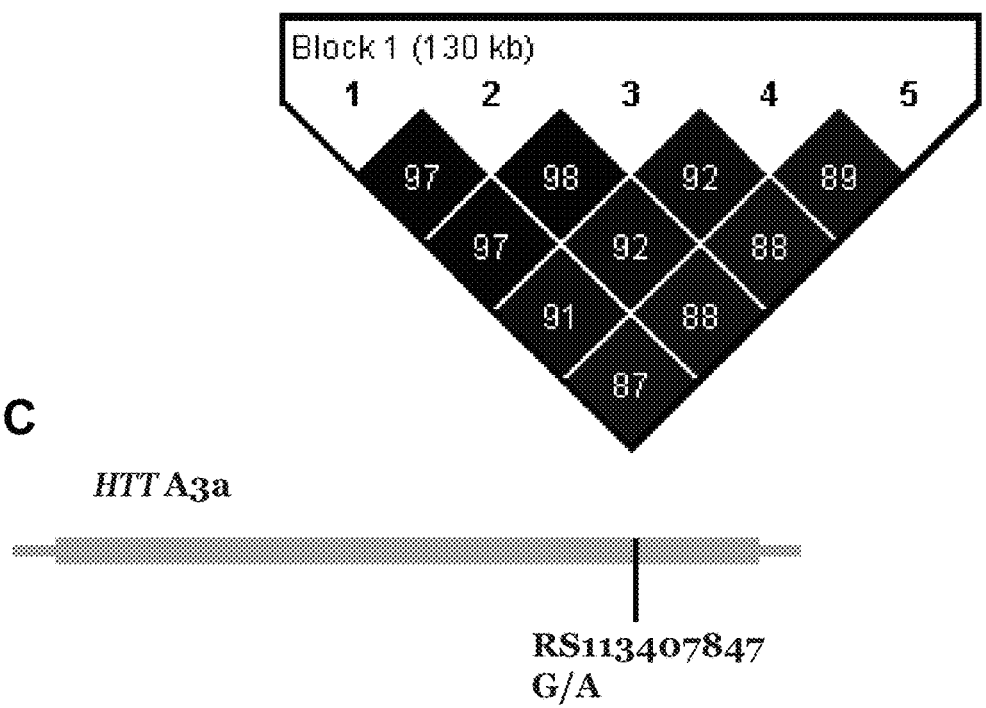

The invention provides, in part, methods and compositions for the treatment of HD. More particularly, polymorphisms are provided that define specific HD haplotypes; such polymorphisms constitute optimal targets for development of allele-specific silencing compounds for use in the treatment, prevention or amelioration of HD.

In the description that follows, a number of terms are used extensively, the following definitions are provided to facilitate understanding of various aspects of the invention. Use of examples in the specification, including examples of terms, is for illustrative purposes only and is not intended to limit the scope and meaning of the embodiments of the invention herein.

Any terms not directly defined herein shall be understood to have the meanings commonly associated with them as understood within the present field of art. Certain terms are discussed below, or elsewhere in the specification, to provide additional guidance to the practitioner in describing the compositions, devices, methods and the like of embodiments, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments described herein.

A method is provided for "treating" Huntington's Disease (HD), wherein treating is meant to encompass selective silencing of CAG-expanded Huntingtin gene (HTT) transcripts and ameliorating symptoms associated with HD, while sparing wild type HTT. The term "treating" as used herein is also meant to include the administration at any stage of HD, including early administration of a compound or late administration. A person of skill in the art would appreciate that the term "ameliorating" is meant to include the prospect of making the HD more tolerable for a subject afflicted therewith (for example, by improving movement and delaying death). Accordingly, as used herein "treatment" may refer to the prevention of HD, the amelioration of symptoms associated with HD, improving movement or other symptoms in the HD patient, extending the life expectancy of the HD patient, or combinations thereof.

Antisense oligonucleotide compounds are typically single stranded DNA or RNA compounds which bind to complementary RNA compounds, such as target mRNA molecules or precursor mRNA molecules, and catalyze downstream events, including inducing RNAse H-dependent degradation of transcripts (Bennett and Swayze 2010). This process is usually passive, in that it does not require or involve additional enzymes to mediate the RNA interference process. Specific targeting of antisense compounds to inhibit the expression of a desired gene may generally involve designing the antisense compound to have a homologous, complementary sequence to the desired gene transcript. Perfect homology may not be necessary for the RNA interference effect. In one embodiment of the invention, the antisense compounds include any DNA or RNA compound with sufficient complementary homology to preferentially bind to the CAG-expanded repeat HTT precursor mRNA or mRNA transcript causing degradation of the CAG-expanded repeat huntingtin transcripts and resulting in reduced production of the polyglutamine expanded repeat huntingtin proteins.

The antisense compounds may be modified to enhance the stability of the oligonucleotides, particularly for in vivo use. Numerous examples of methods for designing and optimizing antisense compounds are found in the journal literature—i.e. (Pan and Clawson 2006; Patzel 2007; Peek and Behlke 2007). The present inventors provide non-limiting examples of antisense compounds which modulate the expression of CAG-expanded huntingtin genes.

Antisense oligonucleotide (ASO) sequences as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

"Oligomer" as used herein is meant to encompass any nucleic acid silencing agent (for example, siRNa, miRNA, ASO in all of their modified forms as described herein) and compositions comprising the nucleic acid silencing agent. An oligomer may act by hybridizing to a target sequence.

A phosphorothioate oligonucleotide bond modification alters the phosphate linkage by replacing one of the non-bridging oxygens with sulfur. The introduction of phosphorothioate linkages alters the chemical properties of the oligonucleotide. In particular, the addition of phosphorothioate linkages reduces nuclease degradation of the oligonucleotide, thereby increasing the half-life in situ. Accordingly, this modification is particularly useful for antisense oligonucleotides, which when introduced into cells or biological matrices can interact with target nucleic acids to silence the expression of a particular transcript. Oligonucleotides containing phosphorothioate linkages accomplish this feat either through direct blockage of translation or enabling enzymatic degradation of the target transcript (for example, via RNase H).

Although phosphorothioate linkages provide improved half-life, the introduction of these linkages into an oligonucleotide may also introduce limitations to their function as antisense oligonucleotides. Each phosphorothioate linkage creates a chiral center at each bond, which may result in multiple isomers of the oligonucleotide generated during synthesis and the isomers may have differential characteristics and functional properties. However, much of the isomer effects may be mitigated through careful positioning of the modifications or by using additional modifications in conjunction with the phosphorothioate bonds.

One or more of the phosphodiester linkages of the oligonucleotide moiety may be modified by replacing one or both of the two bridging oxygen atoms of the linkage with analogues such as —NH, —CH2, or —S. Other oxygen analogues known in the art may also be used.

A "modified oligonucleotide" as used herein is meant to include oligonucleotides that are substituted or modified. In addition to the naturally occurring primary bases adenine, guanine, cytosine, and thymine, or other natural bases such as inosine, deoxyinosine, and hypoxanthine, there are numerous other modifications. For example, isosteric purine 2'deoxy-furanoside analogues, 2'-deoxynebularine or 2'deoxyxanthosine, or other purine and pyrimidine analogues such as 5-methyl pyrimidine or a 5-propynyl pyrimidine may also be utilized to improve stability and target hybridization.

A "modified sugar" as used herein when discussing an oligonucleotide moiety, a sugar modified or replaced so as to be ribose, glucose, sucrose, or galactose, or any other sugar. Alternatively, the oligonucleotide may have one or more of its sugars substituted or modified in its 2' position, i.e. 2'alkyl or 2'-o-alkyl. An example of a 2'-O-alkyl sugar is a 2'-O-methylribonucleotide. Furthermore, the oligonucleotide may have one or more of its sugars substituted or modified to form an α-anomeric sugar.

"Second-generation" oligonucleotides as used herein may be defined as oligonucleotides that are resistant to degradation by cellular nucleases and capable of hybridizing specifically to their target precursor mRNA or mRNA with equal or higher affinity than first generation ASOs. An example of a $2^{nd}$ generation ASO is a 2'-O-(2-Methoxyethyl)-RNA (2'MOE gapmer modification). With a 2'-MOE or a 2'OMe gapmer the 5' and 3' ends may have 2'-MOE modified nucleotides to protect against degradation, but the gap between the 5' and 3' ends may be unmodified phosphodiester or phosphorothioate linkages that are substrates for RNase H. Numerous other chemical modifications have been developed to improve ASOs. For example, morpholino, N3' to P5' phosphoramidate, and methylphosphonate chemical modifications are known in the art (N. Dias, and C. A. Stein 2002). Furthermore, peptide nucleic acids (PNAs) may also be used.

"LNA" as used herein refers to a Locked Nucleic Acid, which is an RNA analog in which the ribose ring is connected by a methylene bridge between the 2'-O and 4'-C atoms thus "locking" the ribose ring in the ideal conformation for Watson-Crick binding. When incorporated into a DNA or RNA oligonucleotide LNAs make the pairing with a complementary nucleotide strand more rapid and increases the stability of the resulting duplex. LNA oligonucleotides have better thermal stability when hybridized to a complementary DNA or RNA strand. Furthermore, LNA oligonucleotides may be made shorter than traditional DNA or RNA oligonucleotides. LNA oligonucleotides are especially useful to detect small or highly similar targets.

"Gapmer" or "gap oligomer", as used herein, refers to a chimeric oligomer having a central portion (a "gap") flanked by 3' and 5' "wings", wherein the gap has a modification that is different as compared to each of the wings. Such modifications may include nucleobase, monomeric linkage, and sugar modifications as well as the absence of a modification (such as unmodified RNA or DNA). Accordingly, a gapmer may be as simple as RNA wings separated by a DNA gap. In some cases, the nucleotide linkages in the wings may be different than the nucleotide linkages in the gap. In certain embodiments, each wing comprises nucleotides with high affinity modifications and the gap comprises nucleotides that do not comprise that modification. Alternatively, the nucleotides in the gap and the nucleotides in the wings may have high affinity modifications, but the high affinity modifications in the gap are different than the high affinity modifications in each of the wings. The modifications in the wings may confer resistance to cleavage by endogenous nucleases, including RNaseH, while the modifications in the gap may be substrates for RNase H. The modifications in the wings may confer resistance to cleavage by endogenous nucleases, including RNaseH, while the modifications in the gap may be substrates for RNase H. The modifications in the wings may be the same or different from one another. The nucleotides in the gap may be unmodified and nucleotides in the wings may be modified. A gapmer has a wing-gap-wing ratio, which may be represented numerically (wing#-gap#-wing#). The gapmer may be symmetric (for example, 9-13-9, 9-12-9, 9-11-9, 9-10-9, 9-9-9, 9-8-9, 9-7-9, 9-6-9, 9-5-9, 9-4-9, 9-3-9, 9-2-9, 9-1-9, 8-15-8, 8-14-8, 8-13-8, 8-12-8, 8-11-8, 8-10-8, 8-9-8, 8-8-8, 8-7-8, 8-6-8, 8-5-8, 8-4-8, 8-3-8, 8-2-8, 8-1-8, 7-15-7, 7-14-7, 7-13-7, 7-12-7, 7-11-7, 7-10-7, 7-9-7, 7-8-7, 7-7-7, 7-6-7, 7-5-7, 7-4-7, 7-3-7, 7-2-7, 7-1-7, 6-15-6, 6-14-6, 6-13-6, 6-12-6, 6-11-6, 6-10-6, 6-9-6, 6-8-6, 6-7-6, 6-6-6, 6-5-6, 6-4-6, 6-3-6, 6-2-6, 6-1-6, 5-15-5, 5-14-5, 5-13-5, 5-12-5, 5-11-5, 5-10-5, 5-9-5, 5-8-5, 5-7-5, 5-6-5, 5-5-5, 5-4-5, 5-3-5, 5-2-5, 5-1-5, 4-17-4, 4-16-4, 4-15-4, 4-14-4, 4-13-4, 4-12-4, 4-11-4, 4-10-4, 4-9-4, 4-8-4, 4-7-4, 4-6-4, 4-5-4, 4-4-4, 4-3-4, 3-24-3, 3-23-3, 3-22-3, 3-21-3, 3-20-3, 3-19-3, 3-18-3, 3-17-3, 3-16-3, 3-15-3, 3-14-3, 3-13-3, 3-12-3, 3-11-3, 3-10-3, 3-9-3, 3-8-3, 3-7-3, 3-6-3, 3-5-3, 3-4-3, 2-26-2, 2-25-2, 2-24-2, 2-22-2, 2-21-2, 2-20-2, 2-19-2, 2-18-2, 2-17-2, 2-16-2, 2-15-2, 2-14-2, 2-13-2, 2-12-2, 2-11-2, 2-10-2, 2-9-2, 2-8-2, 2-7-2, 2-6-2, 2-5-2, 1-26-1, 1-25-1, 1-24-1, 1-22-1, 1-21-1, 1-20-1, 1-19-1, 1-18-1, 1-17-1, 1-16-1, 1-15-1, 1-14-1, 1-13-1, 1-12-1, 1-11-1, 1-10-1, 1-9-1, 1-8-1 or 1-7-1). The gapmer may be asymmetric (for example, 8-13-9, 8-12-9, 8-11-9, 8-10-9, 8-9-9, 8-8-9, 8-7-9, 8-6-9, 8-5-9, 8-4-9, 8-3-9, 8-2-9, 8-1-9, 7-15-8, 7-14-8, 7-13-8, 7-12-8, 7-11-8, 7-10-8, 7-9-8, 7-8-8, 7-7-8, 7-6-8, 7-5-8, 7-4-8, 7-3-8, 7-2-8, 7-1-8, 6-15-7, 6-14-7, 6-13-7, 6-12-7, 6-11-7, 6-10-7, 6-9-7, 6-8-7, 6-7-7, 6-6-7, 6-5-7, 6-4-7, 6-3-7, 6-2-7, 6-1-7, 5-15-6, 5-14-6, 5-13-6, 5-12-6, 5-11-6, 5-10-6, 5-9-6, 5-8-6, 5-7-6, 5-6-6, 5-5-6, 5-4-6, 5-3-6, 5-2-6, 5-1-6, 4-15-5, 4-14-5, 4-13-5, 4-12-5, 4-11-5, 4-10-5, 4-9-5, 4-8-5, 4-7-5, 4-6-5, 4-5-5, 4-4-5, 4-3-5, 4-2-5, 4-1-5, 3-17-4, 3-16-4, 3-15-4, 3-14-4, 3-13-4, 3-12-4, 3-11-4, 3-10-4, 3-9-4, 3-8-4, 3-7-4, 3-6-4, 3-5-4, 3-4-4, 3-3-4, 2-24-3, 2-23-3, 2-22-3, 2-21-3, 2-20-3, 2-19-3, 2-18-3, 2-17-3, 2-16-3, 2-15-3, 2-14-3, 2-13-3, 2-12-3, 2-11-3, 2-10-3, 2-9-3, 2-8-3, 2-7-3, 2-6-3, 2-5-3, 2-4-3, 1-26-2, 1-25-2, 1-24-2, 1-22-2, 1-21-2, 1-20-2, 1-19-2, 1-18-2, 1-17-2, 1-16-2, 1-15-2, 1-14-2, 1-13-2, 1-12-2, 1-11-2, 1-10-2, 1-9-2, 1-8-2, 1-7-2, 3-26-1, 3-25-1, 3-24-1, 3-22-1, 3-21-1, 3-20-1, 3-19-1, 3-18-1, 3-17-1, 3-16-1, 3-15-1, 3-14-1, 4-13-1, 4-12-1, 4-11-1, 4-10-1, 3-9-1, 3-8-1 or 4-7-1).

A chimeric antisense oligonucleotide with a deoxy gap region which is greater than 10 nucleotides in length may be referred as a "gap-widened antisense oligonucleotide". The wing regions may be one to eight high-affinity modified nucleotides in length. The gap-widened antisense oligonucleotides may be 12 to 30 nucleotides in length capable of having, for example, various wing-gap-wing ratio may be selected from: 2-15-1, 1-15-2, 1-14-3, 3-14-1, 1-13-4, 4-13-1, 2-13-3, 3-13-2, 1-12-5, 5-12-1, 2-12-4, 4-12-2, 3-12-3, 1-11-6, 6-11-1, 2-11-5, 5-11-2, 3-11-4, 4-11-3, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-18-1, 1-17-2, 2-17-1, 1-16-3, 3-16-1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. The gap-widened antisense oligonucleotides may have a 2-16-2, 3-14-3, or 4-12-4 wing-gap-wing ratio.

As used herein, the term "high-affinity modification" in relation to a nucleotide refers to a nucleotide having at least one modified nucleobase, internucleoside linkage or sugar moiety, such that the modification increases the affinity of an antisense compound comprising the modified nucleotide to a target nucleic acid. High-affinity modifications include, but are not limited to, bicyclic nucleic acid (BNA)s, LNAs and 2'-MOE. Furthermore, the desirable potency and toxicity characteristics may be obtained by selecting the nucleotide modifications, nucleotide analogues, modified inter-nucleoside linkages, including one or more modified sugar moieties and/or a gapmer wing-gap-wing ratio (for example, see US20100197762).

The compounds, as described herein, may be in isolation, or may be linked to or in combination with tracer compounds, liposomes, carbohydrate carriers, polymeric carriers or other agents or excipients as will be apparent to one of skill in the art. In alternate embodiments, such compounds may further comprise an additional medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent (for example, a transgenic mouse, a mouse or a rat), dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

Compositions or compounds according to some embodiments described herein may be administered in any of a variety of known routes. Examples of methods that may be suitable for the administration of a compound include oral, intravenous, intrathecal, inhalation, intramuscular, subcutaneous, topical, intraperitoneal, intra-rectal or intra-vaginal suppository, sublingual, and the like. The compounds described herein may be administered as a sterile aqueous solution, or may be administered in a fat-soluble excipient, or in another solution, suspension, patch, tablet or paste format as is appropriate. A composition comprising the compounds described herein may be formulated for administration by inhalation. For instance, a compound may be combined with an excipient to allow dispersion in an aerosol. Examples of inhalation formulations will be known to those skilled in the art. Other agents may be included in combination with the compounds described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of the compositions or compounds of some embodiments described herein may vary depending on the route of administration (oral, intravenous, intrathecal, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a compound refers to an amount of the antisense oligomer in such a concentration to result in a therapeutic level of the compound delivered over the term that the compound is used. This may be dependent on the mode of delivery, time period of the dosage, age, weight, general health, sex and diet of the subject receiving the compound. Methods of determining effective amounts are known in the art. It is understood that it may be desirable to target the compounds described herein to a desired tissue or cell type. The compounds described herein may thus be coupled to a targeting moiety. The compounds may be coupled to a cell uptake moiety. The targeting moiety may also function as the cell uptake moiety.

In general, antisense oligonucleotides as described herein may be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some antisense oligonucleotides as described herein may be toxic at some concentrations. Titration studies may be used to determine toxic and non toxic concentrations. Toxicity may be evaluated by examining a particular antisense oligonucleotide's specificity across cell lines. Animal studies may be used to provide an indication if the compound has any effects on other tissues.

A "nucleic acid silencing agent" or an "agent" refers to a composition that acts in a sequence specific manner to effect a reduction in the level of a product (a "gene product") of a given nucleic acid sequence (e.g. a 'gene'). The reduction may be effected by interference with any of the processing of a pre-mRNA following transcription from the DNA of a cell or subject (e.g. splicing, 5' capping, 5' or 3' processing, or export of the processed mRNA to the cytoplasm) or by interference with translation of a mature mRNA, or by specific, directed destruction of the pre-mRNA or mature mRNA. Antisense (ASO) and RNA interference (RNAi-effected by short interfering RNA, or siRNA) are two examples of such methods; microRNA (miRNA) is another.

An antisense oligonucleotide (ASO) is an oligonucleotide that is complementary to a specific RNA sequence, and when hybridized to this specific sequence, interferes with processing or translation of the RNA or triggers degradation of the specific RNA by enzymatic pathways (for example, RNAse H-dependent degradation). The nucleosides comprising an ASO may be purine or pyrimidine nucleosides, or a combination of purine and pyrimidine nucleosides, connected by an internucleoside linkage. ASOs are described generally in, for example, Crooke 2004. Annu. Rev. Med 55:61-95; and in Curr Mol Med 4:465-487. An siRNA is a short (20-30 nucleotide) double-stranded RNA (or modified RNA) molecule that may effect a reduction in the level of a gene product by allowing for specific destruction of mRNA via the RNA interference pathway. The specific mRNA is degraded in the cytoplasm by the RNA-induced silencing complex (RISC). An miRNA is a short (20-30 nucleotide) single-stranded RNA molecule that may effect a reduction in the level of a gene product. An miRNA is complementary to a part of an mRNA, either a coding region or a non-translated region (e.g. 5' untranslated region (UTR), 3' UTR). The miRNA may anneal to form a double-stranded complex and trigger degradation in a process similar to that of siRNA. Translation may also be disrupted by miRNA. A DNA ASO, commonly referred to simply as an ASO, is a short (12-50 nucleotide) single stranded DNA (or modified DNA) molecule that may effect a reduction in the level of a gene product by inducing specific destruction of pre-mRNA or mRNA via RNase H-mediated cleavage. The specific pre-mRNA or mRNA can be degraded in the nucleus and/or the cytoplasm by induction of RNAseH cleavage of DNA-RNA heteroduplexes. A DNA ASO, commonly referred to simply as an ASO, is a short (12-50 nucleotide) single stranded DNA (or modified DNA) molecule that may effect a reduction in the level of a gene product by inducing specific destruction of pre-mRNA or mRNA via RNase H-mediated cleavage. The specific pre-mRNA or mRNA can be degraded in the nucleus and/or the cytoplasm by induction of RNAseH cleavage of DNA-RNA heteroduplexes.

The term 'nucleoside' refers to a molecule of ribose or deoxyribose sugar bonded through carbon-1 of the sugar ring to a nitrogenous base. Examples of nitrogenous bases include purines such as adenine, guanine, 6-thioguanine, hypoxanthine, xanthine, and pyrimidines such as cytosine, thymine and uracil. Examples of purine nucleosides include adenosine (A), guanosine (G), inosine (I), 2'-O-methyl-inosine, 2'-O-methyl-adenosine, 2'-O-methyl-guanine, 2-chlorodeoxyadenosine, 7-halo-7-deaza-adenosine, 7-halo-7-deaza-guanine, 7-propyne-7-deaza adenosine, 7-propyne-7-deaza-guanine, 2-amino-adenosine, 7-deazainosine, 7-thia-7,9-dideazainosine, formycin B, 8-Azainosine, 9-deazainosine, allopurinol riboside, 8-bromo-inosine, 8-chloroinosine, 7-deaza-2-deoxy-xanthosine, 7-Deaza-8-aza-adenosine, 7-deaza-8-aza-guanosine, 7-deaza-8-aza-deoxyadenosine, 7-deaza-8-aza-deoxyguanosine, 7-deaza-adenosine, 7-deaza-guanosine, 7-deaza-deoxyadenosine, 7-deaza-deoxyguanosine, 8-amino-adenosine, 8-amino-deoxyadenosine, 8-amino-guanosine, 8-amino-deoxyguanosine, 3-deaza-deoxyadenosine, 3-deaza-adenosine, 6-thio-deoxyguanosine, and the like, and other purine nucleosides as described in Freier et al 1997 (Nucleic Acids Res. 25:4429-4443), incorporated herein by reference. Examples of pyrimidine nucleosides include deoxyuridine (dU), uridine (U), cytidine (C), deoxycytidine (dC), thymidine (T), deoxy-thymidine (dT), 5-fluoro-uracil, 5-bromouracil, 2'-O-methyl-uridine, 2'-O-methyl cytidine, 5-iodouracil, 5-methoxy-ethoxy-methyl-uracil, 5-propynyl deoxyuridine, pseudoisocytidine, 5-azacytidine, 5-(1-propynyl)cytidine, 2'-deoxypseudouridine, 4-thio-deoxythymidine, 4-thio-deoxyuridine, and the like, and other substituted pyrimidines as disclosed in Freier et al, 1997 (Nucleic Acids Res. 25:4429-4443). Purine or pyrimidine nucleosides also include phosphoramidite derivatives used in oligonucleotide synthesis using standard methods.

"Nucleoside" also includes nucleosides having substituted ribose sugars (bicyclic or otherwise). Some representative patents and publications that teach the preparation of non-bicyclic modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; and 6,600,032; and WO 2005/121371. Some representative patents and publications that teach the preparation of bicyclic modified sugars include, but are not limited to, 'locked nucleic acids', such as those described in WO 99/14226, WO 00/56746, WO 00/56748, WO 01/25248, WO 0148190, WO 02/28875, WO 03/006475, WO 03/09547, WO 2004/083430, U.S. Pat. Nos. 6,268,490, 6,794,499, 7,034,133. Other examples of substituted ribose sugars are described in, for example, Freier, 1997 (Nucleic Acids Res. 25:4429-4443) and Herdewijn et al., 2000. (Antisense Nucleic Acid Drug Dev 10:297-310) both of which are incorporated by reference herein.

A 'nucleotide' refers to a nucleoside having an internucleoside linkage group bonded through the carbon-5 of the sugar ring, usually a mono-, di- or tri-phosphate, and may be suitable for enzymatic polymerization. In other examples, the nucleotides may be phosphoramidites, suitable for non-enzymatic polymerization or synthesis of nucleic acid polymers.

An internucleoside linkage group refers to a group capable of coupling two nucleosides, as part of an oligonucleotide backbone. Examples of internucleoside linkage groups are described by Praseuth et al (Biochimica et Biophysica Acta 1489:181-206) and Summerton et al 1997. (Antisense and Nucleic Acid Drug Dev 7:187-195), both of which are incorporated herein by reference. For example, phosphodiester ($PO_4$—), phosphorothioate ($PO3_s$-), phosphoramidate (N3'-P5') ($PO_3NH$) and methylphosphonate ($PO_3CH_3$), peptidic linkages ("PNA"), and the like; see, for example, U.S. Pat. No. 5,969,118. Inclusion of such modified linkage groups, modified ribose sugars or nitrogenous bases in an oligonucleotide may reduce the rate of hydrolysis of the oligonucleotide in vitro or in vivo.

An "allele" is one of a pair, or one of a series of different forms of a given locus, marker or polymorphism. In a diploid organism or cell, the members of an allelic pair occupy corresponding positions (loci) on a pair of homologous chromosomes. If these alleles are identical, the organism is said to be 'homozygous' for that allele; if they differ, the organism or cell is said to be 'heterozygous' for that allele.

A "haplotype" is a set of alleles of closely linked loci on a chromosome that are generally inherited together. For example, a polymorphic allele at a first site in a nucleic acid sequence on the chromosome may be found to be associated with another polymorphic allele at a second site on the same chromosome, at a frequency other than would be expected for a random association (e.g. "linkage equilibrium"). These two polymorphic alleles may be described as being in linkage disequilibrium (LD). A haplotype may comprise two, three, four or more alleles. The set of alleles in a haplotype along a given segment of a chromosome are generally transmitted to progeny together unless there has been a recombination event.

A "haplogroup" is a group of similar haplotypes that share a common ancestor and that all share the same allele or set of alleles.

A human nucleic acid sequence for "normal" or "wild-type" HTT is exemplified by GenBank reference sequences NM_002111.7 (mRNA) and NC_000004.12 and NT_006051.19 (genomic). The human wild-type HTT protein is exemplified by GenPept reference sequence NP_002102.4. Other examples of such sequences will be available from these or similar databases, or as obtained by sequencing a sample comprising HTT nucleic acid or protein. Subjects with HD are usually heterozygous for the mutant HTT allele of the sequence.

A differentiating polymorphism is a variation in a nucleotide sequence that permits differentiation between a 'wild-type' and mutant allele of a nucleic acid sequence. Differentiating polymorphisms may include insertions or deletions of one or a few nucleotides in a sequence, or changes in one or a few nucleotides in a sequence.

A "single nucleotide polymorphism" or "SNP" is a single nucleotide variation between the genomes of individuals of the same species. In some cases, a SNP may be a single nucleotide deletion or insertion. In general, SNPs occur relatively frequently in genomes and thus contribute to genetic diversity. The density of SNPs in the human genome is estimated to be approximately 1 per 1,000 base pairs. In addition, SNPs are thought to be spaced relatively uniformly throughout the genome. Furthermore, SNPs are thought to be mutationally more stable than other polymorphisms, lending their use to association studies in which linkage disequilibrium between markers and an unknown variant is used to map disease-causing mutations. SNPs may have two, three or four alleles, or (although it may be possible to have three or four different forms of a SNP, corresponding to the different nucleotides), thus facilitating genotyping (by a simple plus/minus assay rather than a length measurement) and automation. The location of a SNP is generally flanked by highly conserved sequences. An individual may be homozygous or heterozygous for an allele at each SNP location. A heterozygous SNP allele is an example of a differentiating polymorphism.

Those of ordinary skill in the art will recognize that nucleic acid molecules are double-stranded and therefore reference to a particular SNP site on a strand also refers to the corresponding site on the complementary strand. Thus, reference may be made to either strand to refer to a particular SNP site or position, SNP allele, or nucleotide sequence, such as those set forth herein.

The sequences (SEQ ID NOs: 1-5) provided in TABLE 1 provide positive strand genomic DNA sequences comprising and flanking the selected polymorphisms illustrated in a 5' to 3' orientation that define the A1, A2 and A3a HD haplotypes of the HTT gene.

TABLE 1

The target DNA sequences for selected polymorphisms that define the A1, A2 and A3a HD haplotypes. The site of the polymorphism is defined in brackets (minor allele/major allele).

| SEQ ID NO: | SNP | Target DNA Sequence (5' to 3') |
| --- | --- | --- |
| 1 and 527 | rs72239206 | tgacagttgtatttttgtttgtgac(-/actt)acgtattatctgttaaaacattttc |
| 2 | rs363107 | tcttaaacttttaaatgccatttgatcttt(g/a)aaaatatatgttttaatagtgtattttaag |
| 3 | rs362313 | ccctcagcgagcaagtcaagctcttcacag(t/c)gatgtcttacaagcgcagagggctctgtga |
| 4 | rs2530595 | gctttgtccctcccccgcttcctccctctg(t/c)ggggaggacccgggaccacagctgctggcc |
| 5 | rs113407847 | ggagagactccactctgaatggggccggga(g/a)gtggggaggactccatttcagatggggtcg |

The sequences provided in TABLE 2 may be useful to a person skilled in the art, to design one or more nucleic acid silencing agents that specifically hybridize to a differentiating polymorphism that defines the A1, A2 or A3 HD haplotypes.

TABLE 2

The reverse complement sequence for selected polymorphisms that define the A1, A2 and A3 HD haplotypes. The site of the polymorphism is defined in brackets.

| SEQ ID NO: | SNP | Reverse Complement of the target DNA Sequence (5' to 3') |
| --- | --- | --- |
| 6 | rs72239206 | gaaaatgttttaacagataatac[GT]gtcacaaacaaaaatacaactgtca |
| 7 | rs363107 | cttaaaatacactattaaaacatatattt[c]aaagatcaaatggcatttaaaagtttaaga |
| 8 | rs362313 | tcacagagccctctgcgcttgtaagacatc[a]ctgtgaagagcttgacttgctcgctgaggg |
| 9 | rs2530595 | ggccagcagctgtggtcccgggtcctcccc[a]cagagggaggaagcggggagggacaaagc |
| 10 | rs113407847 | cgacccatctgaaatggagtcctccccac[c]tcccggccccattcagagtggagtctctcc |

Examples of nucleic acid silencing agents are provided in TABLES 3-7. ASO are examples of nucleic acid silencing agents according to some embodiments of the present invention. Generally, ASOs may be about 20 nucleotides, but may range from about 12 to about 25 nucleotides, or any length in between. For example, an ASO may be 12, 13, 14, 15, 16, 17, 18, 19, 20, 21, 22, 23, 24 or 25 nucleotides in length, with the proviso that the ASO selectively differentiate the nucleic acid molecules at the polymorphism.

TABLE 3

Exemplary ASO sequences that target the rs72239206 polymorphism, which defines the A1 HD haplotype. The location of the specific allele is indicated in upper case font.

| SEQ ID NO: | ASO (5'-3') targeting rs72239206 |
|---|---|
| 11 | gttttaacagataatacGTg |
| 12 | ttttaacagataatacGTgt |
| 13 | tttaacagataatacGTgtc |
| 14 | ttaacagataatacGTgtca |
| 15 | taacagataatacGTgtcac |
| 16 | aacagataatacGTgtcaca |
| 17 | acagataatacGTgtcacaa |
| 18 | cagataatacGTgtcacaaa |
| 19 | agataatacGTgtcacaaac |
| 20 | gataatacGTgtcacaaaca |
| 21 | ataatacGTgtcacaaacaa |
| 22 | taatacGTgtcacaaacaaa |
| 23 | aatacGTgtcacaaacaaaa |
| 24 | atacGTgtcacaaacaaaaa |
| 25 | tacGTgtcacaaacaaaaat |
| 26 | acGTgtcacaaacaaaaata |
| 27 | cGTgtcacaaacaaaaatac |
| 28 | ttttaacagataatacGTg |
| 29 | tttaacagataatacGTgt |
| 30 | ttaacagataatacGTgtc |
| 31 | taacagataatacGTgtca |
| 32 | aacagataatacGTgtcac |
| 33 | acagataatacGTgtcaca |
| 34 | cagataatacGTgtcacaa |
| 35 | agataatacGTgtcacaaa |
| 36 | gataatacGTgtcacaaac |
| 37 | ataatacGTgtcacaaaca |
| 38 | taatacGTgtcacaaacaa |
| 39 | aatacGTgtcacaaacaaa |
| 40 | atacGTgtcacaaacaaaa |
| 41 | tacGTgtcacaaacaaaaa |
| 42 | acGTgtcacaaacaaaaat |
| 43 | cGTgtcacaaacaaaaata |
| 44 | tttaacagataatacGTg |
| 45 | ttaacagataatacGTgt |
| 46 | taacagataatacGTgtc |
| 47 | aacagataatacGTgtca |
| 48 | acagataatacGTgtcac |
| 49 | cagataatacGTgtcaca |
| 50 | agataatacGTgtcacaa |
| 51 | gataatacGTgtcacaaa |
| 52 | ataatacGTgtcacaaac |
| 53 | taatacGTgtcacaaaca |
| 54 | aatacGTgtcacaaacaa |
| 55 | atacGTgtcacaaacaaa |
| 56 | tacGTgtcacaaacaaaa |
| 57 | acGTgtcacaaacaaaaa |
| 58 | cGTgtcacaaacaaaaat |
| 59 | ttaacagataatacGTg |
| 60 | taacagataatacGTgt |
| 61 | aacagataatacGTgtc |
| 62 | acagataatacGTgtca |
| 63 | cagataatacGTgtcac |
| 64 | agataatacGTgtcaca |
| 65 | gataatacGTgtcacaa |
| 66 | ataatacGTgtcacaaa |
| 67 | taatacGTgtcacaaac |
| 68 | aatacGTgtcacaaaca |
| 69 | atacGTgtcacaaacaa |
| 70 | tacGTgtcacaaacaaa |
| 71 | acGTgtcacaaacaaaa |
| 72 | cGTgtcacaaacaaaaa |
| 73 | taacagataatacGTg |
| 74 | aacagataatacGTgt |
| 75 | acagataatacGTgtc |
| 76 | cagataatacGTgtca |
| 77 | agataatacGTgtcac |
| 78 | gataatacGTgtcaca |
| 79 | ataatacGTgtcacaa |
| 80 | taatacGTgtcacaaa |
| 81 | aatacGTgtcacaaac |
| 82 | atacGTgtcacaaaca |

TABLE 3-continued

Exemplary ASO sequences that target the rs72239206 polymorphism, which defines the A1 HD haplotype. The location of the specific allele is indicated in upper case font.

| SEQ ID NO: | ASO (5'-3') targeting rs72239206 |
|---|---|
| 83 | tacGTgtcacaaacaa |
| 84 | acGTgtcacaaacaaa |
| 85 | cGTgtcacaaacaaaa |
| 86 | aacagataatacGTg |
| 87 | acagataatacGTgt |
| 88 | cagataatacGTgtc |
| 89 | agataatacGTgtca |
| 90 | gataatacGTgtcac |
| 91 | ataatacGTgtcaca |
| 92 | taatacGTgtcacaa |
| 93 | aatacGTgtcacaaa |
| 94 | atacGTgtcacaaac |
| 95 | tacGTgtcacaaaca |
| 96 | acGTgtcacaaacaa |
| 97 | cGTgtcacaaacaaa |

TABLE 4

Exemplary ASO sequences that target the rs363107 polymorphism which defines the A2 HD haplotype. The specific allele is indicated in upper case font.

| SEQ ID NO | ASO (5'-3') targeting rs363107 |
|---|---|
| 98 | ctattaaaacatatattttC |
| 99 | tattaaaacatatattttCa |
| 100 | attaaaacatatattttCaa |
| 101 | ttaaaacatatattttCaaa |
| 102 | taaaacatatattttCaaag |
| 103 | aaaacatatattttCaaaga |
| 104 | aaacatatattttCaaagat |
| 105 | aacatatattttCaaagatc |
| 106 | acatatattttCaaagatca |
| 107 | catatattttCaaagatcaa |
| 108 | atatattttCaaagatcaaa |
| 109 | tatattttCaaagatcaaat |
| 110 | atattttCaaagatcaaatg |
| 111 | tattttCaaagatcaaatgg |
| 112 | attttCaaagatcaaatggc |
| 113 | ttttCaaagatcaaatggca |
| 114 | tttCaaagatcaaatggcat |
| 115 | ttCaaagatcaaatggcatt |
| 116 | tCaaagatcaaatggcattt |
| 117 | Caaagatcaaatggcattta |
| 118 | tattaaaacatatattttC |
| 119 | attaaaacatatattttCa |
| 120 | ttaaaacatatattttCaa |
| 121 | taaaacatatattttCaaa |
| 122 | aaaacatatattttCaaag |
| 123 | aaacatatattttCaaaga |
| 124 | aacatatattttCaaagat |
| 125 | acatatattttCaaagatc |
| 126 | catatattttCaaagatca |
| 127 | atatattttCaaagatcaa |
| 128 | tatattttCaaagatcaaa |
| 129 | atattttCaaagatcaaat |
| 130 | tattttCaaagatcaaatg |
| 131 | attttCaaagatcaaatgg |
| 132 | ttttCaaagatcaaatggc |
| 133 | tttCaaagatcaaatggca |
| 134 | ttCaaagatcaaatggcat |
| 135 | tCaaagatcaaatggcatt |
| 136 | Caaagatcaaatggcattt |
| 137 | attaaaacatatattttC |
| 138 | ttaaaacatatattttCa |
| 139 | taaaacatatattttCaa |
| 140 | aaaacatatattttCaaa |
| 141 | aaacatatattttCaaag |
| 142 | aacatatattttCaaaga |
| 143 | acatatattttCaaagat |
| 144 | catatattttCaaagatc |
| 145 | atatattttCaaagatca |
| 146 | tatattttCaaagatcaa |
| 147 | atattttCaaagatcaaa |
| 148 | tattttCaaagatcaaat |

TABLE 4-continued

Exemplary ASO sequences that target the rs363107 polymorphism which defines the A2 HD haplotype. The specific allele is indicated in upper case font.

| SEQ ID NO | ASO (5'-3') targeting rs363107 |
|---|---|
| 149 | attttCaaagatcaaatg |
| 150 | ttttCaaagatcaaatgg |
| 151 | tttCaaagatcaaatggc |
| 152 | ttCaaagatcaaatggca |
| 153 | tCaaagatcaaatggcat |
| 154 | Caaagatcaaatggcatt |
| 155 | ttaaaacatatattttC |
| 156 | taaaacatatattttCa |
| 157 | aaaacatatattttCaa |
| 158 | aaacatatattttCaaa |
| 159 | aacatatattttCaaag |
| 160 | acatatattttCaaaga |
| 161 | catatattttCaaagat |
| 162 | atatattttCaaagatc |
| 163 | tatattttCaaagatca |
| 164 | atattttCaaagatcaa |
| 165 | tattttCaaagatcaaa |
| 166 | attttCaaagatcaaat |
| 167 | ttttCaaagatcaaatg |
| 168 | tttCaaagatcaaatgg |
| 169 | ttCaaagatcaaatggc |
| 170 | tCaaagatcaaatggca |
| 171 | Caaagatcaaatggcat |
| 172 | taaaacatatattttC |
| 173 | aaaacatatattttCa |
| 174 | aaacatatattttCaa |
| 175 | aacatatattttCaaa |
| 176 | acatatattttCaaag |
| 177 | catatattttCaaaga |
| 178 | atatattttCaaagat |
| 179 | tatattttCaaagatc |
| 180 | atattttCaaagatca |
| 181 | tattttCaaagatcaa |
| 182 | attttCaaagatcaaa |
| 183 | ttttCaaagatcaaat |
| 184 | tttCaaagatcaaatg |

TABLE 4-continued

Exemplary ASO sequences that target the rs363107 polymorphism which defines the A2 HD haplotype. The specific allele is indicated in upper case font.

| SEQ ID NO | ASO (5'-3') targeting rs363107 |
|---|---|
| 185 | ttCaaagatcaaatgg |
| 186 | tCaaagatcaaatggc |
| 187 | Caaagatcaaatggca |
| 188 | aaaacatatattttC |
| 189 | aaacatatattttCa |
| 190 | aacatatattttCaa |
| 191 | acatatattttCaaa |
| 192 | catatattttCaaag |
| 193 | atatattttCaaaga |
| 194 | tatattttCaaagat |
| 195 | atattttCaaagatc |
| 196 | tattttCaaagatca |
| 197 | attttCaaagatcaa |
| 198 | ttttCaaagatcaaa |
| 199 | tttCaaagatcaaat |
| 200 | ttCaaagatcaaatg |
| 201 | tCaaagatcaaatgg |
| 202 | Caaagatcaaatggc |

TABLE 5

Exemplary ASO sequences that target the rs362313 polymorphism which defines the A2 HD haplotype. The specific allele is indicated in upper case font.

| SEQ ID NO | ASO (5'-3') targeting rs362313 |
|---|---|
| 203 | tctgcgcttgtaagacatcA |
| 204 | ctgcgcttgtaagacatcAc |
| 205 | tgcgcttgtaagacatcAct |
| 206 | gcgcttgtaagacatcActg |
| 207 | cgcttgtaagacatcActgt |
| 208 | gcttgtaagacatcActgtg |
| 209 | cttgtaagacatcActgtga |
| 210 | ttgtaagacatcActgtgaa |
| 211 | tgtaagacatcActgtgaag |
| 212 | gtaagacatcActgtgaaga |
| 213 | taagacatcActgtgaagag |

TABLE 5-continued

Exemplary ASO sequences that target the rs362313 polymorphism which defines the A2 HD haplotype. The specific allele is indicated in upper case font.

| SEQ ID NO | ASO (5'-3') targeting rs362313 |
|---|---|
| 214 | aagacatcActgtgaagagc |
| 215 | agacatcActgtgaagagct |
| 216 | gacatcActgtgaagagctt |
| 217 | acatcActgtgaagagcttg |
| 218 | catcActgtgaagagcttga |
| 219 | atcActgtgaagagcttgac |
| 220 | tcActgtgaagagcttgact |
| 221 | cActgtgaagagcttgactt |
| 222 | Actgtgaagagcttgacttg |
| 223 | ctgcgcttgtaagacatcA |
| 224 | tgcgcttgtaagacatcAc |
| 225 | gcgcttgtaagacatcAct |
| 226 | cgcttgtaagacatcActg |
| 227 | gcttgtaagacatcActgt |
| 228 | cttgtaagacatcActgtg |
| 229 | ttgtaagacatcActgtga |
| 230 | tgtaagacatcActgtgaa |
| 231 | gtaagacatcActgtgaag |
| 232 | taagacatcActgtgaaga |
| 233 | aagacatcActgtgaagag |
| 234 | agacatcActgtgaagagc |
| 235 | gacatcActgtgaagagct |
| 236 | acatcActgtgaagagctt |
| 237 | catcActgtgaagagcttg |
| 238 | atcActgtgaagagcttga |
| 239 | tcActgtgaagagcttgac |
| 240 | cActgtgaagagcttgact |
| 241 | Actgtgaagagcttgactt |
| 242 | tgcgcttgtaagacatcA |
| 243 | gcgcttgtaagacatcAc |
| 244 | cgcttgtaagacatcAct |
| 245 | gcttgtaagacatcActg |
| 246 | cttgtaagacatcActgt |
| 247 | ttgtaagacatcActgtg |
| 248 | tgtaagacatcActgtga |
| 249 | gtaagacatcActgtgaa |

TABLE 5-continued

Exemplary ASO sequences that target the rs362313 polymorphism which defines the A2 HD haplotype. The specific allele is indicated in upper case font.

| SEQ ID NO | ASO (5'-3') targeting rs362313 |
|---|---|
| 250 | taagacatcActgtgaag |
| 251 | aagacatcActgtgaaga |
| 252 | agacatcActgtgaagag |
| 253 | gacatcActgtgaagagc |
| 254 | acatcActgtgaagagct |
| 255 | catcActgtgaagagctt |
| 256 | atcActgtgaagagcttg |
| 257 | tcActgtgaagagcttga |
| 258 | cActgtgaagagcttgac |
| 259 | Actgtgaagagcttgact |
| 260 | gcgcttgtaagacatcA |
| 261 | cgcttgtaagacatcAc |
| 262 | gcttgtaagacatcAct |
| 263 | cttgtaagacatcActg |
| 264 | ttgtaagacatcActgt |
| 265 | tgtaagacatcActgtg |
| 266 | gtaagacatcActgtga |
| 267 | taagacatcActgtgaa |
| 268 | aagacatcActgtgaag |
| 269 | agacatcActgtgaaga |
| 270 | gacatcActgtgaagag |
| 271 | acatcActgtgaagagc |
| 272 | catcActgtgaagagct |
| 273 | atcActgtgaagagctt |
| 274 | tcActgtgaagagcttg |
| 275 | cActgtgaagagcttga |
| 276 | Actgtgaagagcttgac |
| 277 | cgcttgtaagacatcA |
| 278 | gcttgtaagacatcAc |
| 279 | cttgtaagacatcAct |
| 280 | ttgtaagacatcActg |
| 281 | tgtaagacatcActgt |
| 282 | gtaagacatcActgtg |
| 283 | taagacatcActgtga |
| 284 | aagacatcActgtgaa |
| 285 | agacatcActgtgaag |

TABLE 5-continued

Exemplary ASO sequences that target the rs362313 polymorphism which defines the A2 HD haplotype. The specific allele is indicated in upper case font.

| SEQ ID NO | ASO (5'-3') targeting rs362313 |
|---|---|
| 286 | gacatcActgtgaaga |
| 287 | acatcActgtgaagag |
| 288 | catcActgtgaagagc |
| 289 | atcActgtgaagagct |
| 290 | tcActgtgaagagctt |
| 291 | cActgtgaagagcttg |
| 292 | Actgtgaagagcttga |
| 293 | gcttgtaagacatcA |
| 294 | cttgtaagacatcAc |
| 295 | ttgtaagacatcAct |
| 296 | tgtaagacatcActg |
| 297 | gtaagacatcActgt |
| 298 | taagacatcActgtg |
| 299 | aagacatcActgtga |
| 300 | agacatcActgtgaa |
| 301 | gacatcActgtgaag |
| 302 | acatcActgtgaaga |
| 303 | catcActgtgaagag |
| 304 | atcActgtgaagagc |
| 305 | tcActgtgaagagct |
| 306 | cActgtgaagagctt |
| 307 | Actgtgaagagcttg |

TABLE 6

Exemplary ASO sequences that target the rs2530595 polymorphism which defines the A2 HD haplotype. The specific allele is indicated in upper case font.

| SEQ ID NO: | ASO (5'-3') targeting rs2530595 |
|---|---|
| 308 | gtggtcccgggtcctccccA |
| 309 | tggtcccgggtcctccccAc |
| 310 | ggtcccgggtcctccccAca |
| 311 | gtcccgggtcctccccAcag |
| 312 | tcccgggtcctccccAcaga |
| 313 | cccgggtcctccccAcagag |
| 314 | ccgggtcctccccAcagagg |
| 315 | cgggtcctccccAcagaggg |

TABLE 6-continued

Exemplary ASO sequences that target the rs2530595 polymorphism which defines the A2 HD haplotype. The specific allele is indicated in upper case font.

| SEQ ID NO: | ASO (5'-3') targeting rs2530595 |
|---|---|
| 316 | gggtcctccccAcagaggga |
| 317 | ggtcctccccAcagagggag |
| 318 | gtcctccccAcagagggagg |
| 319 | tcctccccAcagagggagga |
| 320 | cctccccAcagagggaggaa |
| 321 | ctccccAcagagggaggaag |
| 322 | tccccAcagagggaggaagc |
| 323 | ccccAcagagggaggaagcg |
| 324 | cccAcagagggaggaagcgg |
| 325 | ccAcagagggaggaagcggg |
| 326 | cAcagagggaggaagcgggg |
| 327 | Acagagggaggaagcggggg |
| 328 | tggtcccgggtcctccccA |
| 329 | ggtcccgggtcctccccAc |
| 330 | gtcccgggtcctccccAca |
| 331 | tcccgggtcctccccAcag |
| 332 | cccgggtcctccccAcaga |
| 333 | ccgggtcctccccAcagag |
| 334 | cgggtcctccccAcagagg |
| 335 | gggtcctccccAcagaggg |
| 336 | ggtcctccccAcagaggga |
| 337 | gtcctccccAcagagggag |
| 338 | tcctccccAcagagggagg |
| 339 | cctccccAcagagggagga |
| 340 | ctccccAcagagggaggaa |
| 341 | tccccAcagagggaggaag |
| 342 | ccccAcagagggaggaagc |
| 343 | cccAcagagggaggaagcg |
| 344 | ccAcagagggaggaagcgg |
| 345 | cAcagagggaggaagcggg |
| 346 | Acagagggaggaagcgggg |
| 347 | ggtcccgggtcctccccA |
| 348 | gtcccgggtcctccccAc |
| 349 | tcccgggtcctccccAca |
| 350 | cccgggtcctccccAcag |
| 351 | ccgggtcctccccAcaga |

TABLE 6-continued

Exemplary ASO sequences that target the rs2530595 polymorphism which defines the A2 HD haplotype. The specific allele is indicated in upper case font.

| SEQ ID NO: | ASO (5'-3') targeting rs2530595 |
|---|---|
| 352 | cgggtcctccccAcagag |
| 353 | gggtcctccccAcagagg |
| 354 | ggtcctccccAcagaggg |
| 355 | gtcctccccAcagaggga |
| 356 | tcctccccAcagagggag |
| 357 | cctccccAcagagggagg |
| 358 | ctccccAcagagggagga |
| 359 | tccccAcagagggaggaa |
| 360 | ccccAcagagggaggaag |
| 361 | cccAcagagggaggaagc |
| 362 | ccAcagagggaggaagcg |
| 363 | cAcagagggaggaagcgg |
| 364 | Acagagggaggaagcggg |
| 365 | gtcccgggtcctccccA |
| 366 | tcccgggtcctccccAc |
| 367 | cccgggtcctccccAca |
| 368 | ccgggtcctccccAcag |
| 369 | cgggtcctccccAcaga |
| 370 | gggtcctccccAcagag |
| 371 | ggtcctccccAcagagg |
| 372 | gtcctccccAcagaggg |
| 373 | tcctccccAcagaggga |
| 374 | cctccccAcagagggag |
| 375 | ctccccAcagagggagg |
| 376 | tccccAcagagggagga |
| 377 | ccccAcagagggaggaa |
| 378 | cccAcagagggaggaag |
| 379 | ccAcagagggaggaagc |
| 380 | cAcagagggaggaagcg |
| 381 | Acagagggaggaagcgg |
| 382 | tcccgggtcctccccA |
| 383 | cccgggtcctccccAc |
| 384 | ccgggtcctccccAca |
| 385 | cgggtcctccccAcag |
| 386 | gggtcctccccAcaga |
| 387 | ggtcctccccAcagag |

TABLE 6-continued

Exemplary ASO sequences that target the rs2530595 polymorphism which defines the A2 HD haplotype. The specific allele is indicated in upper case font.

| SEQ ID NO: | ASO (5'-3') targeting rs2530595 |
|---|---|
| 388 | gtcctccccAcagagg |
| 389 | tcctccccAcagaggg |
| 390 | cctccccAcagaggga |
| 391 | ctccccAcagagggag |
| 392 | tccccAcagagggagg |
| 393 | ccccAcagagggagga |
| 394 | cccAcagagggaggaa |
| 395 | ccAcagagggaggaag |
| 396 | cAcagagggaggaagc |
| 397 | Acagagggaggaagcg |
| 398 | cccgggtcctccccA |
| 399 | ccgggtcctccccAc |
| 400 | cgggtcctccccAca |
| 401 | gggtcctccccAcag |
| 402 | ggtcctccccAcaga |
| 403 | gtcctccccAcagag |
| 404 | tcctccccAcagagg |
| 405 | cctccccAcagaggg |
| 406 | ctccccAcagaggga |
| 407 | tccccAcagagggag |
| 408 | ccccAcagagggagg |
| 409 | cccAcagagggagga |
| 410 | ccAcagagggaggaa |
| 411 | cAcagagggaggaag |
| 412 | Acagagggaggaagc |

TABLE 7

Exemplary ASO sequences that target the rs113407847 polymorphism, which defines the A3a HD haplotype. The specific allele is indicated in upper case font.

| SEQ ID NO | ASO (5'-3') targeting rs113407847 |
|---|---|
| 413 | gaaatggagtcctccccacC |
| 414 | aaatggagtcctccccacCt |
| 415 | aatggagtcctccccacCtc |
| 416 | atggagtcctccccacCtcc |

TABLE 7-continued

Exemplary ASO sequences that target the rs113407847 polymorphism, which defines the A3a HD haplotype. The specific allele is indicated in upper case font.

| SEQ ID NO | ASO (5'-3') targeting rs113407847 |
|---|---|
| 417 | tggagtcctccccacCtccc |
| 418 | ggagtcctccccacCtcccg |
| 419 | gagtcctccccacCtcccgg |
| 420 | agtcctccccacCtcccggc |
| 421 | gtcctccccacCtcccggcc |
| 422 | tcctccccacCtcccggccc |
| 423 | cctccccacCtcccggcccc |
| 424 | ctccccacCtcccggcccca |
| 425 | tccccacCtcccggccccat |
| 426 | ccccacCtcccggccccatt |
| 427 | cccacCtcccggccccattc |
| 428 | ccacCtcccggccccattca |
| 429 | cacCtcccggccccattcag |
| 430 | acCtcccggccccattcaga |
| 431 | cCtcccggccccattcagag |
| 432 | Ctcccggccccattcagagt |
| 433 | aaatggagtcctccccacC |
| 434 | aatggagtcctccccacCt |
| 435 | atggagtcctccccacCtc |
| 436 | tggagtcctccccacCtcc |
| 437 | ggagtcctccccacCtccc |
| 438 | gagtcctccccacCtcccg |
| 439 | agtcctccccacCtcccgg |
| 440 | gtcctccccacCtcccggc |
| 441 | tcctccccacCtcccggcc |
| 442 | cctccccacCtcccggccc |
| 443 | ctccccacCtcccggcccc |
| 444 | tccccacCtcccggcccca |
| 445 | ccccacCtcccggccccat |
| 446 | cccacCtcccggccccatt |
| 447 | ccacCtcccggccccattc |
| 448 | cacCtcccggccccattca |
| 449 | acCtcccggccccattcag |
| 450 | cCtcccggccccattcaga |
| 451 | Ctcccggccccattcagag |
| 452 | aatggagtcctccccacC |

TABLE 7-continued

Exemplary ASO sequences that target the rs113407847 polymorphism, which defines the A3a HD haplotype. The specific allele is indicated in upper case font.

| SEQ ID NO | ASO (5'-3') targeting rs113407847 |
|---|---|
| 453 | atggagtcctccccacCt |
| 454 | tggagtcctccccacCtc |
| 455 | ggagtcctccccacCtcc |
| 456 | gagtcctccccacCtccc |
| 457 | agtcctccccacCtcccg |
| 458 | gtcctccccacCtcccgg |
| 459 | tcctccccacCtcccggc |
| 460 | cctccccacCtcccggcc |
| 461 | ctccccacCtcccggccc |
| 462 | tccccacCtcccggcccc |
| 463 | ccccacCtcccggcccca |
| 464 | cccacCtcccggccccat |
| 465 | ccacCtcccggccccatt |
| 466 | cacCtcccggccccattc |
| 467 | acCtcccggccccattca |
| 468 | cCtcccggccccattcag |
| 469 | Ctcccggccccattcaga |
| 470 | atggagtcctccccacC |
| 471 | tggagtcctccccacCt |
| 472 | ggagtcctccccacCtc |
| 473 | gagtcctccccacCtcc |
| 474 | agtcctccccacCtccc |
| 475 | gtcctccccacCtcccg |
| 476 | tcctccccacCtcccgg |
| 477 | cctccccacCtcccggc |
| 478 | ctccccacCtcccggcc |
| 479 | tccccacCtcccggccc |
| 480 | ccccacCtcccggcccc |
| 481 | cccacCtcccggcccca |
| 482 | ccacCtcccggccccat |
| 483 | cacCtcccggccccatt |
| 484 | acCtcccggccccattc |
| 485 | cCtcccggccccattca |
| 486 | Ctcccggccccattcag |
| 487 | tggagtcctccccacC |
| 488 | ggagtcctccccacCt |

TABLE 7-continued

Exemplary ASO sequences that target the rs113407847 polymorphism, which defines the A3a HD haplotype. The specific allele is indicated in upper case font.

| SEQ ID NO | ASO (5'-3') targeting rs113407847 |
|---|---|
| 489 | gagtcctccccacCtc |
| 490 | agtcctccccacCtcc |
| 491 | gtcctccccacCtccc |
| 492 | tcctccccacCtcccg |
| 493 | cctccccacCtcccgg |
| 494 | ctccccacCtcccggc |
| 495 | tccccacCtcccggcc |
| 496 | ccccacCtcccggccc |
| 497 | cccacCtcccggcccc |
| 498 | ccacCtcccggcccca |
| 499 | cacCtcccggccccat |
| 500 | acCtcccggccccatt |
| 501 | cCtcccggccccattc |
| 502 | Ctcccggccccattca |
| 503 | ggagtcctccccacC |
| 504 | gagtcctccccacCt |
| 505 | agtcctccccacCtc |
| 506 | gtcctccccacCtcc |
| 507 | tcctccccacCtccc |
| 508 | cctccccacCtcccg |
| 509 | ctccccacCtcccgg |
| 510 | tccccacCtcccggc |
| 511 | ccccacCtcccggcc |
| 512 | cccacCtcccggccc |
| 513 | ccacCtcccggcccc |
| 514 | cacCtcccggcccca |
| 515 | acCtcccggccccat |
| 516 | cCtcccggccccatt |
| 517 | Ctcccggccccattc |

The invention provides one or more nucleic acid silencing agents having a sequence of one or more than one of SEQ ID NO: 6-517 or portions or fragments thereof.

In a further aspect, the invention provides the use of one or more ASOs having a sequence of one or more than one of SEQ ID NO: 6-517 to treat, prevent or ameliorate HD.

TABLE 8

The target DNA sequences for selected polymorphisms that define the A1, A2 and A3 HD haplotypes. Target polymorphic variant shown.

| SEQ ID NO | SNP | Target DNA Sequence (5' to 3') |
|---|---|---|
| 522 | rs72239206 | tgacagttgtattttttgtttgtgacacgtatt atctgttaaaacattttc |
| 523 | rs363107 | tcttaaacttttaaatgccatttgatctttga aaatatatgttttaatagtgtattttaag |
| 524 | rs362313 | ccctcagcgagcaagtcaagctcttcacagtg atgtcttacaagcgcagagggctctgtga |
| 525 | rs2530595 | gctttgtccctcccccgcttcctccctctgtg gggaggacccgggaccacagctgctggcc |
| 526 | rs113407847 | ggagagactccactctgaatggggccgggagg tggggaggactccatttcagatggggtcg |

Materials and Methods

The following methods were employed respect to the Examples described herein.

Genotyping and Haplotype Assignment in Canadian Subjects

91 SNPs were genotyped in >1000 Canadian Caucasian HD patients and relatives using the Illumina GoldenGate genotyping array and BeadXpress platform. Genotypes were called using Illumina GenomeStudio software, and 91-SNP haplotypes were reconstructed using PHASE V2.1. Haplotypes were manually annotated, then phased to CAG repeat length and confirmed for sequence identity by familial relationship. 28/91 SNPs in our original panel are rare or occur predominantly in non-Caucasian ethnic groups, leaving 63 SNPs of >1% frequency in European populations (1000 Genomes). 51 of these 63 common SNPs occur within the HTT gene sequence, and were used for annotation of intragenic haplotypes within the extended 63 SNP haplotype.

Analysis of HTT Haplotypes in 1000 Genomes

Variant call files (VCFs) encompassing the HTT gene region (GRCh37 3034088-3288007, +/- 50 kb of HTT gene, SHAPEIT haplotypes) were downloaded from the 1000 Genomes Project Consortium (Phase I) using the Data Slicer tool and analyzed in the R statistical computing environment. 2166 phased haplotypes of chromosome 4 were available from 1083 individuals. Chromosomes bearing the intragenic A1 haplotype were identified using rs362307, a previously defined tagging SNP [24]. SNPs present on at least 90% of the 76 chromosomes containing rs362307[T] (i.e. SNPs present on at least 70 of 76 chromosomes) but also present on less than 100 of all 2166 chromosomes were identified as candidate A1 markers for further analysis. A2 chromosomes were similarly identified using rs2798235 and rs363080, the defining A2 markers from manual 63-SNP haplotype annotation of the Canadian Caucasian cohort. Discovery of linked A2 variants followed a similar strategy as for linked A1 variants. A3 chromosomes were identified among A haplogroup chromosomes by exclusion of all chromosomes bearing any specific A haplotype-defining SNPs in our 63-SNP panel. A1, A2, and A3 subtype markers were defined as any SNP present on a subset of each haplotype, but on no other chromosomes in the complete 1000 Genomes data set. Following identification of all A1, A2, and A3 variants, phased genotypes of intragenic HTT SNPs present at ≥5% EUR frequency in the 1000 Genomes Phase I data set were extracted from all 738 European chromosomes and manually annotated in comparison to our directly genotyped 63-SNP haplotype data.

Genotyping and Haplotype Assignment in European Subjects

200 Swedish, 100 French, and 291 Italian HD family members were identified from the UBC HD BioBank and in cooperation with IRCCS Neuromed in Pozzilli, Italy. All French and Swedish samples were collected in their respective countries of origin for HD gene mapping studies in the 1990s. Of these samples, 120 Swedish, 76 French, 22 Finnish, and 209 Italian family members were identified as phaseable for haplotype and CAG repeat length. All haplotype-defining 63 SNPs genotyped in the Canadian Caucasian cohort were genotyped in the selected European samples, with addition of 6 novel A1 and A1 subtype SNPs, 5 novel A2 and A2 subtype SNPs, and a novel A3 subtype SNP. European samples were additionally genotyped at 15 SNPs not present in the 63 SNP panel but necessary for reconstruction of haplotypes inferred in prior 4p16.3 locus genotyping [22]. Haplotypes in European samples were reconstructed with PHASE v2.1 and manually annotated as for the Canadian Caucasian cohort.

Direct Genotyping of HTT A1 Variants

A1 markers rs149109767 and rs72239206 are biallelic indels, and were genotyped by fragment analysis in phaseable samples from the UBC HD BioBank with 63-SNP haplotype data. Genotypes of rs149109767 and rs72239206 were phased to SNP haplotype and CAG repeat length by familial relationship. In total, 454 phased, nonredundant HD chromosomes and 652 nonredundant control chromosomes were directly genotyped and phased to CAG repeat length. PCR products containing rs149109767 were amplified using dye-labeled del2642F (6FAM-GCTGGGGAACAGCAT-CACACCC identified as SEQ ID NO: 518) and del2642 R (CCTGGAGTTGACTGGAGACTTG identified as SEQ ID NO: 519). Products containing rs72239206 were amplified with delACTT 3F (GAGGATTGACCACACCACCT identified as SEQ ID NO: 520) and dye-labeled delACTT 3R (HEX-ATGTGGCCATTTGACACGATA identified as SEQ ID NO: 521). Primers were multiplexed for ease of genotyping, and PCR products analyzed by ABI 3730xl BioAnalyzer with GeneMapper software.

Design of A1-Targeted Antisense Oligonucleotides

Locked nucleic acid (LNA) gapmer ASOs targeting the mutant ΔACTT (rs72239206), rs363107, rs362313, rs2530595, rs113407847 minor alleles and corresponding major allele reference sequence were designed in-house and synthesized by Exiqon on a fee-for-service basis. Oligos were resuspended in 1×TE and stored at −20 C between transfection experiments.

Passive Transfection of HD Patient Cells with A1-Targeted ASOs

Human HD lymphoblasts previously haplotyped as A1/C1 haplotypes (Coriell NIGMS Human Genetic Cell Repository ID #GM03620, CAG lengths 59/18), were cultured in 2 mL complete RPMI media (500,000 cells in 15% FBS+1% pen-strep) with 78 nM, 312 nM, or 1250 nM varying doses of ASO sequences were cultured in 2 mL complete RPMI media (500,000 cells in 15% FBS+1% pen-strep) with 78 nM, 312 nM, or 1250 nM varying doses of ASO sequences. Cells were incubated 120 h, and harvested for Western blot analysis as described previously [25]. Anti-non-muscle myosin IIA (Abeam ab24762) immunoblotting was used as a loading control.

Active Transfection of HD Patient Cells with A1, A2, or A3a-Targeted ASOs

Human HD lymphoblasts previously haplotyped as either A1/C1 haplotypes (Coriell NIGMS Human Genetic Cell Repository ID #GM03620, CAG lengths 59/18), A2/C haplotypes (Coriell NIGMS Human Genetic Cell Repository ID #GM02150, CAG lengths 44/18) or A3a/C haplotypes (Coriell NIGMS Human Genetic Cell Repository ID #GM04724, CAG lengths 67/15) were cultured in 2 mL complete RPMI media (15% FBS+1% pen-strep). 1-5×106 cells were transfected by electroporation using the Amaxa Nucleofector Kit C (VCA-1004) for each ASO dose in 100 μL nucleofector solution. Cells were incubated 72 or 120 h, and harvested for Western blot analysis as described previously [25]. Anti-non-muscle myosin IIA (Abeam ab24762) immunoblotting was used as a loading control.

Allele-Specific HTT mRNA Quantification

Figure 3:
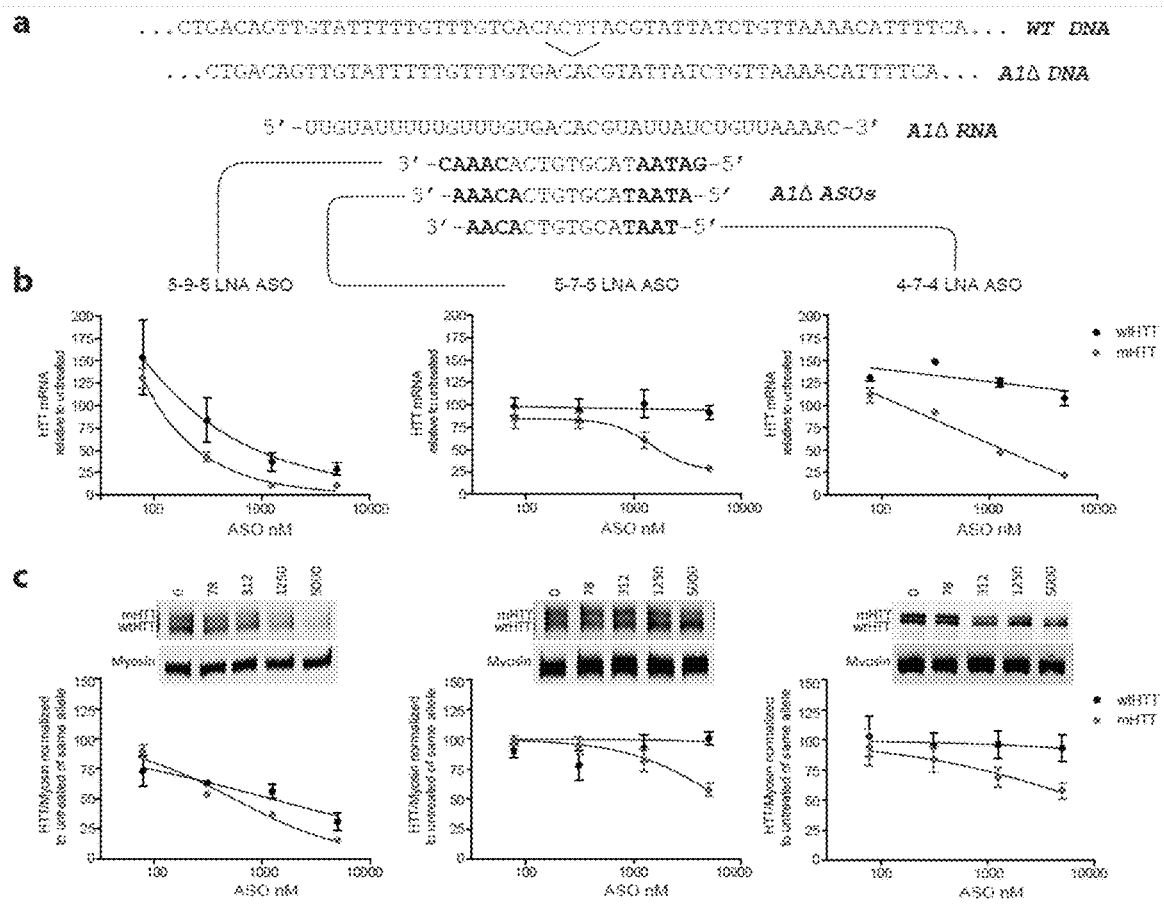
FIG. 3(a) Design of antisense oligonucleotide gapmers selectively targeting mutant HTT A1 mRNA at the ΔACTT (rs72239206) sequence. (b) Transfection of patient-derived lymphoblasts (44/18 CAG) with ΔACTT-complementary ASOs selectively reduces mutant HTT mRNA. Patient lymphoblasts transfected with 5-9-5 (SEQ ID NO: 36), 5-7-5 (SEQ ID NO: 66) and 4-7-4 LNA (SEQ ID NO: 92) gapmers show dose-dependent reduction of mutant HTT mRNA relative to untreated controls, falling to 21.5% mutant HTT mRNA at the highest 4-7-4 dose. Wild-type HTT mRNA levels do not fall below untreated levels at any tested dose of 5-7-5 (SEQ ID NO: 66) or 4-7-4 LNA (SEQ ID NO: 92) gapmer. (c) Dose-dependent reduction of mutant HTT protein relative to untreated controls, sparing wtHTT at all tested 5-7-5 and 4-7-4 LNA gapmer doses. and* represent p=0.01 and p=0.001 by ANOVA with Bonferroni post hoc.

For FIG. 3, transfected cells were re-cultured for 24 h, and half of each culture pelleted for RNA extraction, cDNA synthesis, and allele-specific qPCR. Remaining cell culture was propagated for protein analysis at 72 h. For all other figures, transfected cells were harvested at 120 h for RNA extraction, cDNA synthesis, and allele-specific qPCR. A1 and C1 HTT mRNA transcript was quantified in quadruplicate for each dose of each experiment using TaqMan probe designed to rs362331 (ABI, C_—2231945_10) and normalized to GAPDH (ABI, 4333764F). All experiments were performed three time, with two transfection replicates for each data point in each experiment (n=4-6 for each data point).

Allele-Specific HTT Protein Quantification

Human HD lymphoblasts previously haplotyped as either A1/C haplotypes (Coriell NIGMS Human Genetic Cell Repository ID #GM03620, CAG lengths 59/18), A2/C haplotypes (Coriell NIGMS Human Genetic Cell Repository ID #GM02150, CAG lengths 44/18), A3a/C haplotypes (Coriell NIGMS Human Genetic Cell Repository ID #GM04724, CAG lengths 67/15) were cultured in 2 mL complete RPMI media (15% FBS+1% pen-strep). 1×106 cells were transfected by electroporation using the Amaxa Nucleofector Kit C (VCA-1004) for each ASO dose in 100 μL nucleofector solution. Transfected lymphoblast cultures were harvested at 72 h (FIG. 3) or 120 h (FIGS. 5-9) and pelleted for quantitative Western blot analysis. Cells were pelleted by centrifugation at 250 g for 5 min at 4 C and stored at −80° C. Proteins were extracted by lysis with SDP+ buffer and 30-60 μg of total protein was resolved on 10% low-BIS acrylamide gels and transferred to 0.45 μm nitrocellulose membrane as previously described (Carroll et al., 2011). Membranes were blocked with 5% milk in PBS, and then blotted with anti-HTT antibody 2166 (Millipore) for detection of HTT. Anti-non-muscle myosin IIA (Abcam ab24762) immunoblotting was used as a loading control. Secondary antibodies, IR dye 800CW goat anti-mouse (Rockland 610-131-007) and AlexaFluor 680 goat anti-rabbit (Molecular Probes A21076), were used for detection and membranes were scanned using the LiCor Odyssey Infrared Imaging system. Licor Image Studio Lite was used to quantify the intensity of the individual bands (n=3-6 for each data point). Figure data are presented as mean+/−SEM. Two way ANOVA with Bonferroni post hoc test was performed for each dose series and p-values illustrated with and* for p=0.01 and p=0.001, respectively. Representative images for HTT were chosen.

In Vivo ASO Treatment with ASOs

YAC128 HD model mice [26] were maintained under a 12 h light: 12 h dark cycle in a clean facility and given free access to food and water. Experiments were performed with the approval of the animal care committee of the University of British Columbia. ASOs were delivered by intracerebroventricular injection as in [19] at the indicated doses diluted to a final volume of 10 μl in sterile PBS. Four weeks later, brains were collected and sectioned in a 1 mm coronal rodent brain matrix (ASI Instruments). The most anterior 2 mm section, containing mostly olfactory bulb, was discarded. The next most anterior 2 mm section, containing mostly cortex and striatum, was divided into hemispheres and lysed as previously described [19]. 40 μg total protein was used for allele-specific HTT protein quantification as above.

The following examples are provided for illustrative purposes and are not intended to be limiting as such:

EXAMPLES

Example 1

SNPs Across HTT Represent Gene-Spanning Haplotypes and the A1, A2, and A3a Haplotypes Represent the Most Common Gene-Spanning HD Haplotypes In order to determine the frequency and heterozygosity of different allele-specific HTT targets relative to one another, we sought to establish the haplotypes for a large number of common polymorphisms across the HTT gene region. Various partial haplotypes have been constructed across HTT, but sequence identity and recombination between these haplotypes has remained ambiguous due to low marker density across the ~170 kb gene sequence. We previously genotyped 91 SNPs across the HTT gene region [18], of which 63 are present at greater than 1% frequency in European populations [27]. Of these 63 common SNPs, 51 are located between the start of the HTT 5' UTR and the end of the 3UTR (chr4:3076408-3245687, GRCh37) (not shown). In total, 527 Canadian HD patients and 305 control relatives from the UBC HD Biobank were genotyped and phased at all 63 SNPs for this study. Using patterns of familial segregation, we reconstructed gene-spanning haplotypes at all 63 SNPs for 293 unrelated CAG-expanded chromosomes (CAG>35) and 829 control chromosomes (CAG≤35) from Canadian individuals of European ancestry. The annotation of dense 63-SNP haplotypes replicated the major haplogroup assignments previously obtained using 22 tSNPs across the HTT gene region [24, 28], and confirmed that recombination between common haplotypes principally occurs extragenic to the HTT gene. For example, the A3 haplotype is frequently associated with a historical extragenic 5' crossover with the C1 haplotype, whereas no common haplotype is observed with C1 recombined within the HTT gene sequence. Only 9/283 (3.2%) HD chromosomes and 25/829 (3.0%) control chromosomes in our Canadian cohort represent intragenic recombinants of gene-spanning HTT haplotypes, confirming that recombination within HTT is rare. Analysis of pairwise linkage disequilibrium (LD) between genotypes of all 63 SNPs in 1664 phased haplotypes from Canadian HD patients and controls reveals a ~170 kb region of high LD (D'>0.9) from rs762855 to rs362303 (chr4: 3074795-3242307), indicating a haplotype block of exceedingly low recombination across the entire transcribed HTT sequence (not shown).

In contrast, stringent pairwise LD by correlation coefficient ($r^2$) reveals a punctuated pattern of SNP disequilibrium within the HTT haplotype block, reflecting a diversity of haplotypes spanning the gene locus. Strikingly, SNPs in high pairwise correlation within HTT tag specific intragenic haplotypes. For example, rs2798235 and rs363080 represent unique markers of the A2 haplotype and are found in near-perfect pairwise correlation ($r^2$=0.98), whereas both SNPs show low pairwise correlation with all other variants in the 63-SNP panel. Both SNPs are highly specific, linked markers of the A2 haplotype spanning the entire HTT gene. The observed pattern of high LD across HTT, and the presence of identical haplotypes tagged by unique sets of SNPs, shows that SNPs within HTT represent specific haplotypes or groups of haplotypes encompassing the entire HTT sequence, uninterrupted by historical recombination. Among Canadian subjects, 95.8% (271/283) of HD chromosomes and 95.9% (795/829) of control chromosomes conform to 20 specific non-recombinant haplotypes at 51 common intragenic SNPs and at exon 1 CCG repeat length (TABLE 9).

TABLE 9 shows 20 common intragenic haplotypes from the Canadian Caucasian cohort (51 SNPs).

| | rs3856973 3080173 | rs2285086 3089259 | rs7659144 3098321 | rs16843804 3104390 | rs2024115 3104568 | rs3733217 3107334 | rs10015979 3109442 | rs7691627 3111410 | rs2798235 3114832 | rs1936032 3117168 | rs4690072 3122507 | rs6446723 3126813 | rs363070 3131573 | rs363081 3133627 | rs363080 3133911 | rs363075 3137674 | rs363064 3141410 |
|---|---|---|---|---|---|---|---|---|---|---|---|---|---|---|---|---|---|
| A1 | G | A | C | C | A | C | G | G | G | C | T | T | A | G | C | G | C |
| A2a | G | A | C | C | A | C | G | G | A | C | T | T | A | G | T | A | C |
| A2b | G | A | C | C | A | C | G | G | A | C | T | T | A | G | T | G | C |
| A3 | G | A | C | C | A | C | G | G | G | C | T | T | A | G | C | G | C |
| A4a | G | A | C | C | A | C | G | G | G | C | T | T | A | G | C | G | C |
| A4b | G | A | C | C | A | C | G | G | G | C | T | T | A | G | C | G | C |
| A5a | G | A | C | C | A | C | G | G | G | C | T | T | A | G | C | G | C |
| A5b | G | A | C | C | A | C | A | G | G | C | T | T | A | G | C | G | C |
| A5c | G | A | C | C | A | T | A | G | G | C | T | T | A | G | C | G | C |
| B1 | G | A | C | C | A | C | A | G | G | C | T | T | A | G | C | G | C |
| B2 | A | A | C | T | G | C | A | G | G | C | T | C | C | G | C | G | C |
| C1 | A | A | G | C | G | C | A | A | G | C | G | C | A | G | C | G | C |
| C2a | A | G | G | C | G | C | A | A | G | C | G | C | A | G | C | G | C |
| C2b | A | G | G | C | A | C | A | A | G | C | G | C | A | G | C | G | C |
| C3a | A | G | C | C | A | C | A | A | G | C | G | C | A | G | C | G | C |
| C3b | A | G | C | C | G | C | A | A | G | C | G | C | A | G | C | G | T |
| C4 | A | A | C | C | G | C | A | A | G | G | G | C | A | G | C | G | C |
| C5 | A | A | C | C | G | C | A | A | G | C | G | C | G | G | C | G | C |
| C6 | A | A | C | C | G | C | A | A | G | C | G | C | A | G | C | G | C |
| C8 | A | G | C | T | G | C | A | A | G | G | G | C | A | G | C | G | C |

| | rs363072 3142528 | rs3025849 3143767 | rs12502045 3147268 | rs35892913 3148570 | rs11143646 3148653 | rs363102 3149016 | rs11731237 3151813 | rs4690073 3160150 | rs363144 3161295 | rs363099 3162056 | rs3025837 3174845 | rs363096 3180021 |
|---|---|---|---|---|---|---|---|---|---|---|---|---|
| A1 | A | A | C | G | T | A | T | G | T | C | A | T |
| A2a | A | A | C | G | T | G | C | G | T | C | A | C |
| A2b | A | A | C | G | T | G | G | G | T | C | A | C |
| A3 | A | A | C | G | G | A | T | G | G | C | A | T |
| A4a | A | A | C | G | T | A | C | G | T | C | A | T |
| A4b | T | A | C | G | T | A | T | G | T | T | A | T |
| A5a | T | A | T | G | T | A | C | G | T | C | A | T |
| A5b | A | A | C | G | T | A | C | G | T | C | A | T |
| A5c | T | A | C | G | T | A | C | A | T | C | A | C |
| B1 | A | G | C | G | T | G | C | A | T | C | A | C |
| B2 | T | A | C | G | T | G | C | A | T | C | A | C |
| C1 | T | A | C | G | T | A | C | A | C | C | A | C |
| C2a | A | G | C | G | T | G | C | A | T | C | A | C |
| C2b | A | A | C | G | T | G | C | A | T | C | A | C |
| C3a | A | A | C | G | T | G | C | A | T | C | A | C |
| C3b | A | A | C | G | T | G | C | A | T | C | A | C |
| C4 | A | A | C | G | T | A | C | A | T | C | A | C |
| C5 | A | A | C | G | T | G | C | A | T | T | A | C |
| C6 | A | A | C | G | T | A | C | A | T | C | A | C |
| C8 | A | A | C | G | T | A | C | A | T | C | A | C |

TABLE 9-continued shows 20 common intragenic haplotypes from the Canadian Caucasian cohort (51 SNPs).

| | rs2298967 3185747 | rs2298969 3186244 | rs10488840 3186993 | rs363125 3189547 | rs6844859 3190486 | rs363092 3196029 | rs7685686 3207142 | rs363088 3210330 | rs362331 3215835 | rs916171 3216815 | rs362325 3219326 |
|---|---|---|---|---|---|---|---|---|---|---|---|
| A1 | T | T | G | C | T | C | A | A | T | C | G |
| A2a | T | T | G | C | T | C | A | A | T | C | G |
| A2b | T | T | G | C | T | C | A | A | T | C | G |
| A3 | T | T | G | C | T | C | A | A | T | C | G |
| A4a | T | T | G | C | T | C | A | A | T | C | G |
| A4b | T | T | G | C | T | C | A | A | T | C | G |
| A5a | T | T | G | C | T | C | A | A | T | C | G |
| A5b | T | T | G | C | T | C | A | A | T | C | G |
| A5c | T | T | G | C | T | C | G | A | T | C | G |
| B1 | T | T | G | C | T | C | A | A | T | C | G |
| B2 | T | T | G | C | T | C | A | T | T | C | G |
| C1 | C | C | A | A | C | A | A | A | C | G | C |
| C2a | T | T | A | A | C | A | G | A | C | G | C |
| C2b | T | T | A | A | C | A | G | A | C | G | C |
| C3a | T | T | A | A | C | A | G | A | C | G | C |
| C3b | T | T | A | A | C | A | G | A | C | G | C |
| C4 | T | T | A | A | C | A | G | A | C | G | C |
| C5 | T | T | G | A | C | A | A | A | T | G | G |
| C6 | T | T | A | A | C | A | G | A | C | G | C |
| C8 | C | T | G | C | C | A | G | T | C | G | G |

| | rs362275 3224602 | rs362273 3227419 | rs2276881 3231661 | rs3121419 3232257 | rs362272 3234980 | rs362271 3235518 | rs3775061 3238754 | rs363310 3239776 | rs362307 3241845 | rs362306 3242100 | rs362303 3242307 |
|---|---|---|---|---|---|---|---|---|---|---|---|
| A1 | C | A | G | C | G | G | G | A | T | G | C |
| A2a | C | A | G | C | G | G | G | A | C | G | C |
| A2b | C | A | G | C | G | G | G | A | C | G | C |
| A3 | C | A | G | C | G | G | G | A | C | G | C |
| A4a | C | A | G | C | G | G | G | A | C | G | C |
| A4b | C | A | G | C | G | G | G | A | C | G | C |
| A5a | C | A | A | C | G | G | G | A | C | G | C |
| A5b | C | A | G | C | G | G | G | A | C | G | C |
| A5c | T | G | G | C | G | G | G | A | C | G | C |
| B1 | C | A | G | C | G | G | G | A | C | A | C |
| B2 | C | A | G | C | G | G | G | A | C | G | C |
| C1 | C | A | G | T | A | A | A | G | C | G | T |
| C2a | C | A | G | C | G | G | G | A | C | G | T |
| C2b | C | A | G | C | G | G | G | A | C | G | T |
| C3a | C | A | G | C | G | G | G | A | C | G | T |
| C3b | C | A | G | C | G | G | G | A | C | G | T |
| C4 | C | A | G | C | G | G | G | A | C | G | T |
| C5 | C | A | G | C | G | G | G | A | C | G | C |
| C6 | C | A | G | C | G | G | G | A | C | G | T |
| C8 | T | G | G | T | A | A | A | G | C | A | C |

We next determined the most frequent gene-spanning haplotypes occurring on HD chromosomes. Among 283 unrelated Canadian HD chromosomes, 48.1% (136/283) are found on the A1 haplotype marked by rs362307, 32.2% (91/283) are found on closely related A2a or A2b, and 12.0% (34/283) are found on A3. In total, 92.2% (261/283) of Canadian HD chromosomes are found on A1, A2, or A3 haplotypes spanning HTT. Among control chromosomes, only 8.0% are A1, 16.4% are A2a or A2b, and 13.1% are A3. Haplotypes A4 and A5, each present on 6.3% of control chromosomes, are never observed on Canadian HD chromosomes. Notably, A1 and A2a represent the most genetically distant haplotypes within the A haplogroup, despite representing the most frequent HD haplotypes. Haplogroup B is a distinct genetic lineage in 5.3% of HTT controls, present on only 3/283 HD chromosomes in the Canadian cohort (1.1%). Haplogroup C is a complex collection of haplotypes constituting nearly half of unrelated control chromosomes (42.6%), but is found on only 3.2% of HD chromosomes. The most common intragenic haplotype among all annotations is C1, present on 29.8% of unrelated control chromosomes in the Canadian cohort.

Example 2

Identification of all Defining Intragenic Alleles on HD-Associated Haplotypes

Mutant HTT is enriched for gene-spanning A1 and A2 haplotypes relative to controls. This suggests that alleles found exclusively on these haplotypes may represent attractive targets for allele-specific silencing of mutant HTT. To determine all polymorphisms uniquely found on the most frequent HD-associated haplotypes (A1 and A2), we identified all chromosomes in the 1000 Genomes Project whole genome sequencing data bearing these haplotype-specific SNPs. In total, 2297 intragenic polymorphisms are annotated across HTT (chr4:3076408-3245687, GRCh37) in the 1000 Genomes Phase I data set.

In our 51-SNP panel, the A1 haplotype is uniquely defined by rs362307, a [T/C] SNP present in exon 67 and the 3' UTR of HTT. Among all 1000 Genomes chromosomes, 3.5% (76/2166) carry this SNP. Among the 76 chromosomes bearing rs362307[T], 75 carry the glutamic acid deletion known as Δ2642 (rs149109767) and 74 carry a novel 4 bp intron deletion (rs72239206). Among all 2166 chromosomes, including those 76 bearing rs362307[T], Δ2642 is present on 77 and rs72239206 is present on 83. Therefore 97.4% (75/77) of chromosomes with Δ2642 and 89.2% (74/83) of those with rs72239206 also carry rs362307[T]. Both polymorphisms thus represent highly sensitive proxy markers of rs362307 (FIG. 1a). No other SNPs were as strongly associated with rs362307. For example, the next most common SNP also present on at least 90% of the A1 chromosomes was found nonspecifically on 633/2166 chromosomes. Among SNPs less frequent than rs362307, one intragenic SNP (rs187059132) occurs specifically on a subset of 32/76 A1 chromosomes. Variants rs362307, rs149109767 (Δ2642), and rs72239206 (ΔACTT) are therefore highly specific for the A1 haplotype, having high pairwise correlation ($r^2 > 0.9$) with each other but with no other SNPs in the 1000 Genomes data set. All three A1-defining polymorphisms are found almost exclusively on individuals of European or Admixed European ethnicity (TABLE 10), in agreement with the reported absence of rs149109767 (Δ2642) alleles in individuals of East Asian and black South African ancestry [28, 29].

TABLE 10 shows A1 allele counts (n) and relative frequencies (%) among the HD and control chromosomes from the UBC HD Biobank (labelled as CMMT HD chromosomes and CMMT normal chromosomes) and from normal chromosomes obtained from the 1000 Genomes Phase I sequence data.

| | | chromosomes | rs362307 | | Δ2642 | | ΔACTT | |
|---|---|---|---|---|---|---|---|---|
| | | n | n | % | n | % | n | % |
| CMMT HD chromosomes | | | | | | | | |
| | Caucasian | 454 | 214 | 47.1% | 217 | 47.8% | 216 | 47.6% |
| | East Asian | 53 | 0 | 0.0% | 0 | 0.0% | 0 | 0.0% |
| | Black African | 19 | 0 | 0.0% | 0 | 0.0% | 0 | 0.0% |
| CMMT normal chromosomes | | | | | | | | |
| | Caucasian | 652 | 42 | 6.4% | 43 | 6.6% | 40 | 6.1% |
| | East Asian | 94 | 0 | 0.0% | 0 | 0.0% | 0 | 0.0% |
| | Black African | 211 | 0 | 0.0% | 0 | 0.0% | 0 | 0.0% |
| 1000 Genomes normal chromsomes | | | | | | | | |
| MXL | Mexican | 132 | 11 | 8.33% | 11 | 8.33% | 12 | 9.09% |
| CEU | CEPH (Caucasian, Utah) | 170 | 14 | 8.24% | 13 | 7.65% | 13 | 7.65% |
| GBR | British | 178 | 13 | 7.30% | 13 | 7.30% | 14 | 7.87% |
| FIN | Finnish | 186 | 13 | 6.99% | 13 | 6.99% | 13 | 6.99% |
| CLM | Colombian | 120 | 7 | 5.83% | 7 | 5.83% | 12 | 10.00% |
| TSI | Toscan | 178 | 10 | 5.62% | 11 | 6.18% | 11 | 6.18% |
| PUR | Puerto Rican | 110 | 4 | 3.64% | 4 | 3.64% | 5 | 4.55% |
| ASW | African American | 122 | 3 | 2.46% | 3 | 2.46% | 3 | 2.46% |
| CHB | Han Chinese in Beijing | 194 | 1 | 0.52% | 0 | 0.00% | 0 | 0.00% |
| CHS | Han Chinese South | 200 | 0 | 0.00% | 0 | 0.00% | 0 | 0.00% |
| IBS | Iberian | 28 | 0 | 0.00% | 1 | 3.57% | 0 | 0.00% |

TABLE 10-continued shows A1 allele counts (n) and relative frequencies (%) among the HD and control chromosomes from the UBC HD Biobank (labelled as CMMT HD chromosomes and CMMT normal chromosomes) and from normal chromosomes obtained from the 1000 Genomes Phase I sequence data.

|  |  | chromosomes | rs362307 |  | Δ2642 |  | ΔACTT |  |
|---|---|---|---|---|---|---|---|---|
|  |  | n | n | % | n | % | n | % |
| JPT | Japanese | 178 | 0 | 0.00% | 1 | 0.56% | 0 | 0.00% |
| LWK | Luhya | 194 | 0 | 0.00% | 0 | 0.00% | 0 | 0.00% |
| YRI | Yoruban | 176 | 0 | 0.00% | 0 | 0.00% | 0 | 0.00% |
|  | 1000 Genomes Total | 2166 | 76 | 3.51% | 77 | 3.55% | 83 | 3.83% |

The A2 haplotype, comprised of closely related subtypes A2a and A2b, is uniquely tagged by rs2798235 and rs363080 in our 51-SNP panel as described above. 100 chromosomes in 1000 Genomes Phase I carry rs363080, of which 98 also carry rs2798235. The latter SNP is exclusively found on chromosomes tagged by rs363080, and no other chromosomes. High pairwise correlation between these two markers is similarly observed in direct genotyping of our Canadian HTT chromosomes ($r^2$=0.98). In 1000 Genomes, three additional intragenic SNPs—rs363107, rs362313, and rs2530595—are found on 100, 99, and 99 of chromosomes bearing rs363080, respectively, and are likewise present only on these chromosomes. All five polymorphisms are present on 98% of chromosomes bearing any of the five variants, and therefore represent specific markers of the A2 haplotype (FIG. 1b).

HD also commonly occurs on A3. In our 51-SNP panel, the A3 haplotype is defined by intragenic markers of the A haplo-group in the absence of SNPs specific for the other A haplotypes. 119 A3 haplotypes were identified out of 738 control chromosomes of European ancestry (16.1%). No identifying SNPs were found that uniquely encompass all 119 A3 chromosomes. However, a specific subtype SNP was observed on 45.4% (54/119) of A3 chromosomes—rs113407847—designating A3a (FIG. 1c). In the 738 European individuals, rs113407847 is found only in the subset of A3 haplotypes. Despite common association with HD, no SNPs specific to both A1 and A3 were found, except when shared with other, non-HD associated A haplotypes.

Example 3

Validation of Polymorphisms Specific for the HTT A1 Haplotype

To validate the in silico association of all three A1-defining polymorphisms from low-coverage whole genome sequencing data in 1000 Genomes, Δ2642 and rs72239206 were directly genotyped and phased to the CAG repeat in HTT chromosomes previously genotyped for rs362307. These comprised all Canadian HD chromosomes genotyped with the original 63-SNP panel as well as other previously haplotyped samples from various ethnic groups. In total, 454 phased, nonredundant HD chromosomes and 652 nonredundant control chromosomes were successfully genotyped and phased to the CAG repeat at rs149109767 (Δ2642), and rs72239206. Pairwise LD of direct genotyping data indicates that all three polymorphisms are present in HD and control chromosomes in near-perfect LD ($r^2$>0.99, TABLE 11) and that all three minor alleles are highly enriched on HD chromosomes versus controls.

TABLE 11 direct genotyping of a1 haplotype-defining alleles rs362307, rs149109767, rs72239206 in Caucasian HD and normal chromosomes from the UBC HD BioBank.

|  |  | HD |  | Normal |  | Chi-Square |
|---|---|---|---|---|---|---|
|  |  | n | % | n | % | p = |
| rs72239206 | Δ | 214 | 47.1% | 42 | 6.4% | 5.37E−204 |
| (ΔACTT) | ACTT | 240 | 52.9% | 610 | 93.6% |  |
|  | Total | 454 |  | 652 |  |  |
| rs149109767 | Δ | 217 | 47.8% | 43 | 6.6% | 1.52E−204 |
| (Δ2642) | GAG | 237 | 52.2% | 609 | 93.4% |  |
|  | Total | 454 |  | 652 |  |  |
| rs362307 | T | 216 | 47.6% | 40 | 6.1% | 4.09E−220 |
|  | C | 238 | 52.4% | 612 | 93.9% |  |
|  | Total | 454 |  | 652 |  |  |

Marker studies of the Δ2642 codon deletion suggest that the frequency of the A1 haplotype varies considerably between Caucasian HD patient populations (i.e. Finnish, American, Swedish, Canadian, French, Croatian, Indian, Italian, Chinese and Japanese). A key question following our definition of specific gene-spanning HD haplotypes was therefore to determine the distribution of these haplotypes among different patient populations of European ancestry. A revised SNP panel was designed to include the prior 63-SNP panel as well as the novel defining A1, A2, and A3 SNPs derived from the 1000 Genomes Project. Using this revised panel, we genotyped 120 Swedish, 76 French, and 209 Italian HD family members, derived from respective countries of origin. Haplotypes were reconstructed and phased to CAG repeat size, in the same manner as the Canadian Caucasian cohort. All common 63-SNP haplotypes found in the Canadian Caucasian cohort were replicated by genotyping of the European HD cohorts using our revised panel. All three A1 variants and all five A2 variants conformed to high expected pairwise correlation in direct genotyping of the European cohorts with the revised panel (FIG. 1). Among all European patients, the CAG expansion on A3 was found exclusively in phase with the unique A3a-identifying SNP rs113407847, but not on A3b lacking this SNP, suggesting that A3a is a disease-associated haplotype. Direct genotyping of rs113407847 in Canadian HD A3 chromosomes similarly revealed that the CAG expansion occurs almost exclusively on A3a when present on A3 (31 of 34 A3 Canadian HD chromosomes). Common HD-associated haplotypes A1, A2, and A3a therefore share uniform sets of defining markers in ethnically distinct European HD patient cohorts, implying deep ancestral relationship of these disease-associated haplotypes across different European populations.

Whereas the sequence identity of intragenic HTT haplotypes is consistent across Caucasian HD patient populations, our direct genotyping reveals striking differences in frequency of specific HD-associated haplotypes among both CAG-expanded chromosomes and control chromosomes in different European populations. Among unrelated Swedish HD chromosomes, 51% (26/51) are found on A1, similar to our previously genotyped Canadian HD cohort (p=0.7616, Fisher's Exact). The frequency of A2 among Swedish HD is comparatively lower than in Canada (18% versus 32%, p=0.0455) and A3a is more frequent (28% versus 11% in Canadians, p=0.0033). French HD chromosomes are also most frequently A1 (45% versus 48%, p=0.7654) with A2 present at similar frequencies and A3a more common than in Canadian HD (A2, p=0.1957; A3a, p=0.0256). In contrast, Italian HD chromosomes are predominantly found on A2 (58%, p<0.0001 versus Canadian), with a much smaller proportion of HD on A1 versus the Canadian cohort (19%, p<0.0001) and a similar proportion of A3a (7%, p=0.2647). In a small set of Finnish HD families, haplotyped with our original 63-SNP panel, all unrelated disease chromosomes are A1 (6/10, 60%) or A2 (4/10, 40%). Despite differences in specific haplotype frequency between our Canadian and European cohorts, >90% of HD chromosomes are found on A1, A2, and A3a haplotypes in all four populations of Northern European ancestry and in 84% of Italian HD chromosomes. HTT haplotypes on control chromosomes also differ between European populations, though less dramatically than CAG-expanded chromosomes. The haplogroup trends toward higher frequency in Italian controls versus Canadian (p=0.0597), but is found at similar frequency among Swedish (p=0.6838) and French control chromosomes (p=0.8073). A1 occurs at statistically similar frequencies in all four control cohorts, whereas A2 occurs at higher frequency among Italian controls than in Canadian (24% versus 16%, p=0.0185) or Swedish controls (13%, p=0.0203), mirroring its elevated frequency among Italian HD chromosomes.

Example 4

A1, A2, and A3 Haplotypes Represent Optimal Target Panels for Allele-Specific HTT Silencing in HD Patient Populations High pairwise correlation of specific haplotype-defining polymorphisms allows for targeting of the A1 and A2 haplotypes as a selective HTT silencing strategy. As all three A1 markers are present in near-perfect LD, targeting any single A1 polymorphism will allow allele-specific HTT silencing in a nearly equal number of HD patients heterozygous for this haplotype. Heterozygosity of A1 in HD patients, when phased to the CAG expansion, is highest in Sweden (47%), Canada (44%), and France (43%), but much lower in Italy (15%), suggesting greater utility in patients of Northern European ancestry (FIG. 10).

An estimated 98% of patients with HD on A2 (phased to rs363080) will have all five A2 targets present. The percent of patients heterozygous for A2, phased to the CAG expansion, range from to 18% in Sweden to 43% in Italy, suggesting a greater utility in Southern European populations. Tertiary targeting of rs113407847 would allow treatment of patients bearing the CAG expansion on A3a, ranging from a maximum of 27% of patients in Sweden to only 5% in Italy. In total, targeting three specific polymorphisms representing A1, A2, and A3a may allow selective silencing treatment of ~80% of HD patients overall from the Canadian, Swedish, French, and Italian patient populations. Defining SNPs of these HD-associated haplotypes therefore represent panels of targets that could achieve ~80% patient treatment by allele-specific HTT silencing strategies.

Example 5

ASOs Selectively Silence HTT A1 in Human Cells

Among all genotyped HD patients in this study, A1 is the most frequently heterozygous haplotype in cis with the expanded CAG repeat. The defining A1 markers rs362307, rs149109767 (Δ2642), and rs72239206 therefore represent allele-specific targets with the greatest heterozygosity in HD patients when the variant allele is phased to the CAG repeat expansion. Both rs362307 and rs149109767 (Δ2642) are found in mature mRNA, have known association with the CAG repeat expansion, and have been investigated as targets of siRNA-mediated selective HTT silencing [21, 30]. Unlike these variants, rs72239206 is intronic and has no previously reported association with the CAG expansion. We sought to evaluate the potential of rs72239206 as a selective HTT silencing target using ASOs directed to the mutant sequence.

In addition to offering a novel A1 target not previously associated with HD, we hypothesized that targeting of the 4 bp rs72239206 indel sequence may offer greater selectivity than discrimination by a single nucleotide polymorphism, and sought to evaluate the potential of rs72239206 as a selective mutant HTT silencing target. Unlike rs362307 and Δ2642, rs72239206 is located in an intron (intron 22 of HTT) and is therefore only targetable by agents complementary to un-spliced pre-mRNA. ASOs can induce RNAse H-mediated degradation of complementary pre-mRNA as well as mRNA, [31] and we therefore designed ASO sequences incorporating a gapmer design with locked nucleic acid (LNA) wings and phosphorothioate linkages complementary to the rs72239206 deletion sequence. (FIG. 3a).

Figure 2:
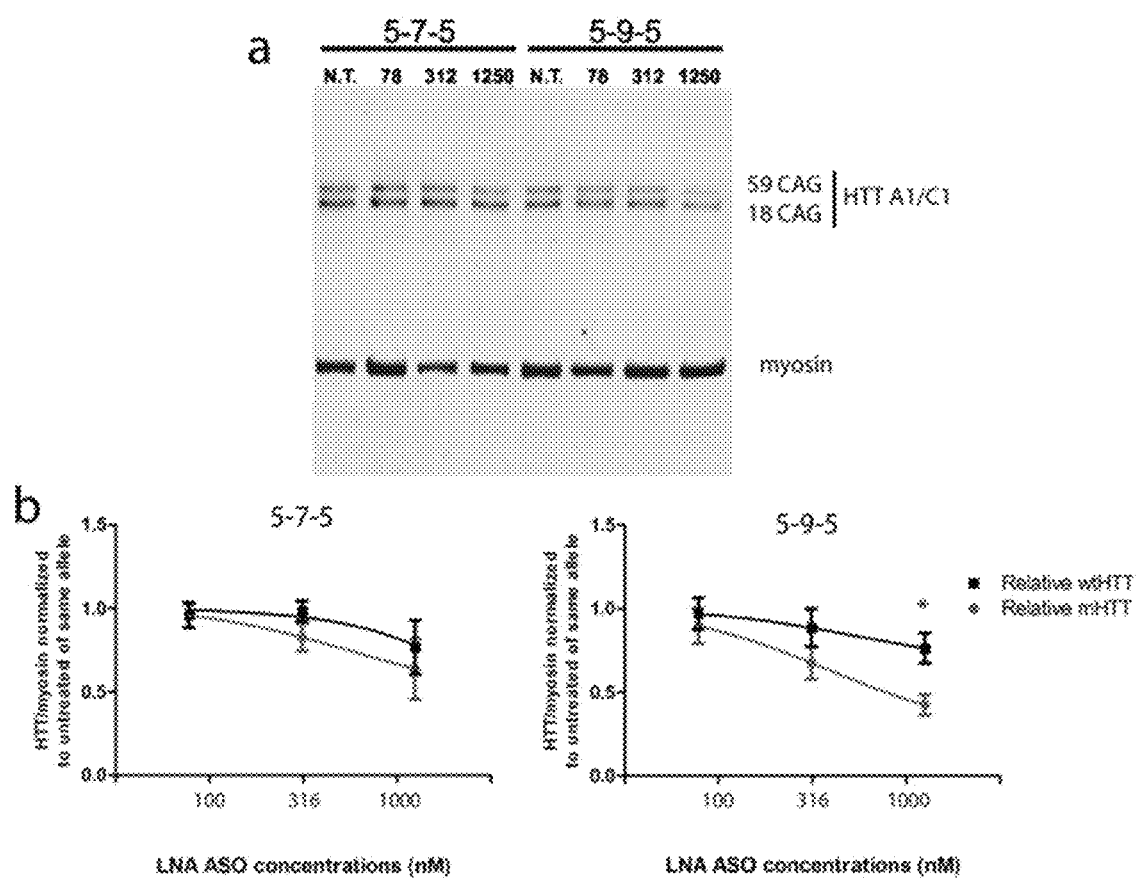
FIG. 2(a) Passive transfection of patient-derived lymphoblasts with ΔACTT-complementary ASO selectively reduces mutant HTT protein. Patient lymphoblasts transfected with 5-7-5 (SEQ ID NO: 66) and 5-9-5 (SEQ ID NO: 36) LNA gapmers show dose-dependent reduction of mutant HTT protein relative to untreated controls. Non-muscle myosin was used as a loading control. (b) Quantification of relative mHTT and wtHTT levels following 120 hr treatment of juvenile A1 lymphoblasts at 78, 312, and 1250 nM ASO in media (n=4, *p<0.05).
Figure 5:
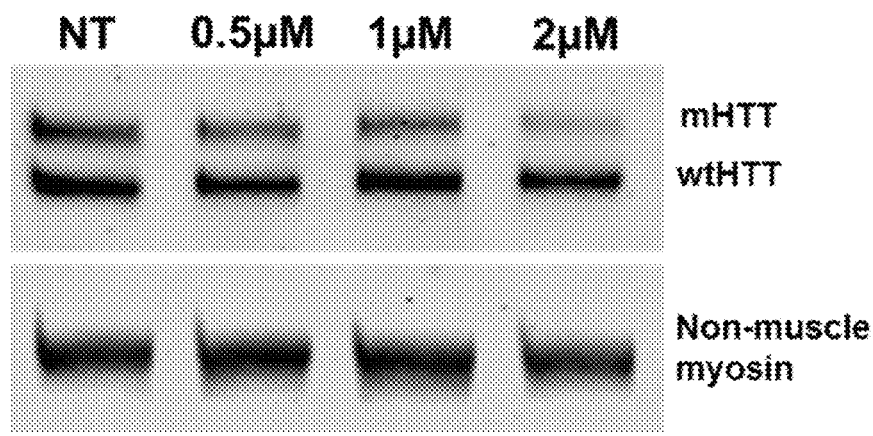
FIG. 5 shows that active transfection of patient-derived lymphoblasts with rs72239206-complementary ASO selectively reduces mutant HTT protein. HD patient-derived lymphoblasts (A1/C haplotypes; CAG lengths 59/18) treated with a 4-9-4 LNA/phosphorothioate backbone gapmer with sequence +A*+T*+A*+A*T*A*C*G*T*G*T*C*A*+C*+A*+A*+A (*=phosphorothioate linkages, +=LNA) (SEQ ID NO: 66) show a dose-dependent reduction of mutant HTT protein relative to untreated controls. Cells were treated with either 0.5, 1, 2 or 5 μM of ASO or left untreated for 120 hrs and harvested for western blot analysis. Mutant and wild type huntingtin were separated on a 7% low-bis gel and band intensities were quantified by densitometry. Non-muscle myosin was used a loading/normalization control. Relative huntingtin levels are presented on the graph. N=4, error bars represent standard error.
Figure 5:
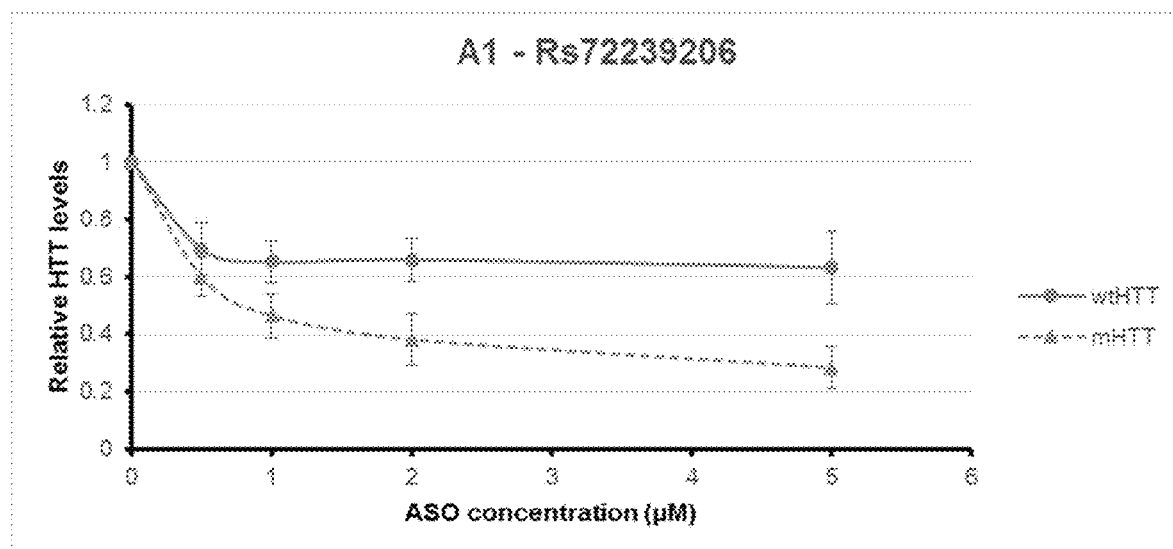

ASOs are passively taken up by neurons in primary culture [18]. In the absence of transgenic HTT neurons bearing rs72239206, we sought to test the silencing potential of LNA gapmers by passive uptake in human HD lymphoblasts bearing the A1 haplotype (GM03620, CAG 59/18). Remarkably, A1 HTT is selectively silenced in human lymphoblasts grown with rs2239206-targeted LNA gapmers in media, suggesting that lymphoblasts also passively take up ASO in culture. (FIG. 2 shows the A1/C1 lymphoblasts treated with a 5-9-5 LNA gapmer (SEQ ID NO: 36) and FIG. 5 shows the A1/C1 lymphoblasts treated with a 4-9-4 LNA gapmer (SEQ ID NO: 66). On the basis of these preliminary experiments, we sought to examine dose-dependent knockdown of A1 HTT mRNA and protein in HD patient lymphoblasts of typical CAG length using active transfection to maximize effective dose.

Transfection of human A1/C1 lymphoblasts with a 5-9-5 LNA gapmer (SEQ ID NO: 36) resulted in potent HTT mRNA silencing, but only minimal discrimination between A1 and C1 transcripts (11% A1 and 29% C1 HTT mRNA remaining at the highest dose versus untreated cells) (FIG. 3). Reduction of the DNA gap by two nucleotides to a 5-7-5 configuration (SEQ ID NO: 66) improved selectivity, with the HTT A1 transcript reduced to 29% of untreated mRNA levels at the highest dose versus 92% HTT C1 control. Shortening this molecule to a 4-7-4 LNA gapmer design (SEQ ID NO: 92) further improved selectivity for the HTT A1 transcript, reducing A1 HTT mRNA to 28.5% of untreated levels at the highest transfection dose while sparing HTT C1 mRNA (FIG. 3b). Western blot analysis using allelic separation of CAG 44/18 bands revealed similar reduction at the protein level for all three LNA gapmer designs, inducing dose-dependent reduction of mutant HTT with 5-7-5 and 4-7-4 gapmers while sparing normal HTT (FIG. 3c). Targeting the A1-specific rs72239206 deletion sequence with complementary ASOs can potently and selectively silence mutant HTT mRNA and protein in cells genetically representative of HD patients bearing the A1 haplotype.

Example 6

Targeting the rs72239206 Deletion Site is Efficacious and Tolerated In Vivo

Figure 4:
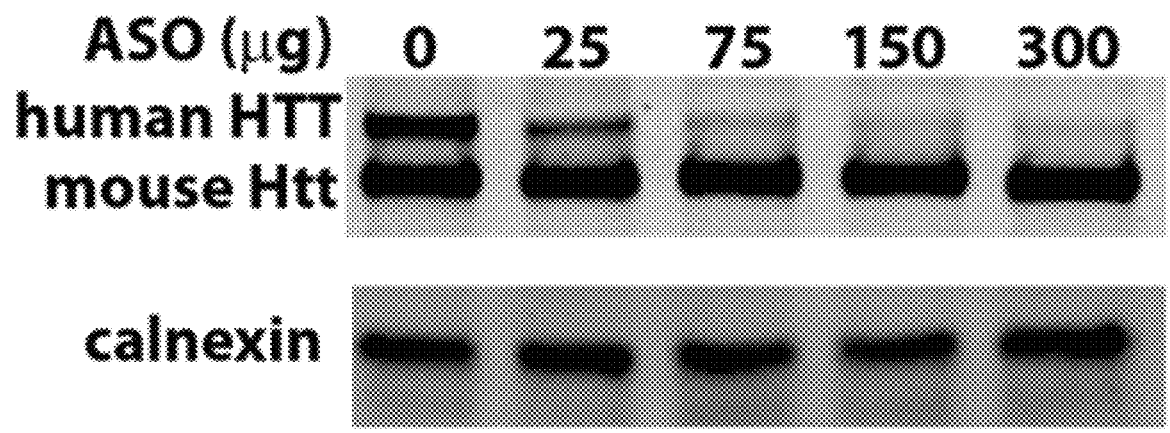
FIG. 4(a) Four weeks post ICV injection of YAC128 mice with WT 5-9-5 LNA gapmer complementary to the rs72239206 major allele results in potent reduction of mutant HTT protein in vivo relative to untreated controls. (b) Quantification of relative human HTT and mouse Htt levels following treatment with the indicated doses of WT 5-9-5 LNA gapmer.
Figure 4:
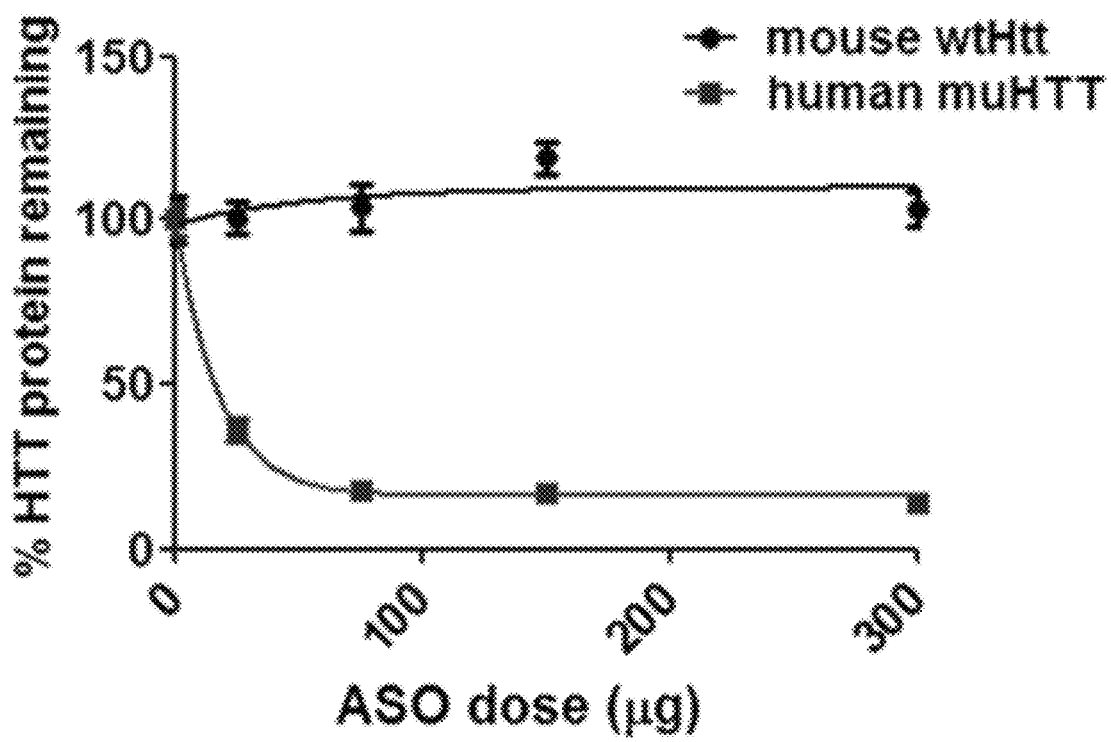

In the absence of transgenic mice bearing the rs72239206 deletion in cis with expanded CAG, in vivo silencing of A1 HTT mRNA and protein could not be directly evaluated. However, the wild-type analog of the 5-9-5 LNA gapmer (SEQ ID NO: 36), designed against reference sequence that includes the four bases deleted in A1, also elicited potent reduction of human HTT in brains of YAC128 mice bearing transgenic full-length mutant HTT (FIG. 4). The rs72239206 deletion site is therefore accessible to ASO-mediated HTT mRNA silencing in vivo.

Example 7

ASOs Silence HTT A2 in Human Cells

Figure 6:
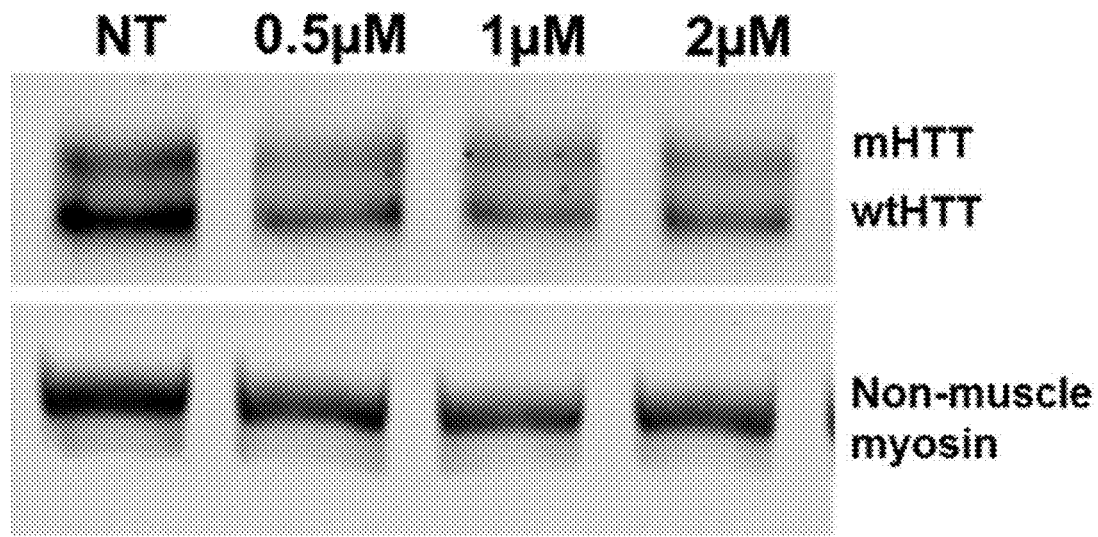
FIG. 6 shows that active transfection of patient-derived lymphoblasts with a rs2530595-complementary ASO reduces mutant HTT protein. HD patient-derived lymphoblasts (A2/C haplotypes; CAG lengths 44/18) treated with a 4-9-4 LNA/phosphorothioate backbone gapmer with the sequence +T*+C*+C*+T*C*C*C*C*A*C*A*G*A*+G*+G*+G*+A (*=phosphorothioate linkages, +=LNA) (SEQ ID NO: 373) show a dose-dependent reduction of mutant HTT protein relative to untreated controls. Cells were treated with either 0.5, 1, 2 or 5 μM of ASO or left untreated for 120 hrs and harvested for western blot analysis. Mutant and wild type huntingtin were separated on a 7% low-bis gel and band intensities were quantified by densitometry. Non-muscle myosin was used a loading/normalization control. Relative huntingtin levels are presented on the graph below. N=3, error bars represent standard error.
Figure 6:
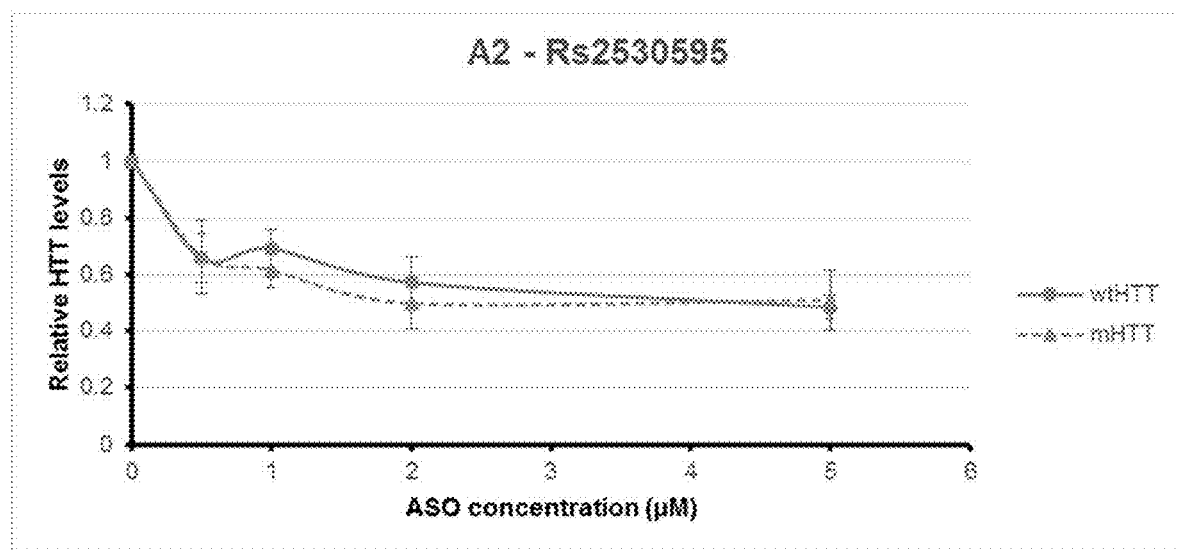
Figure 7:
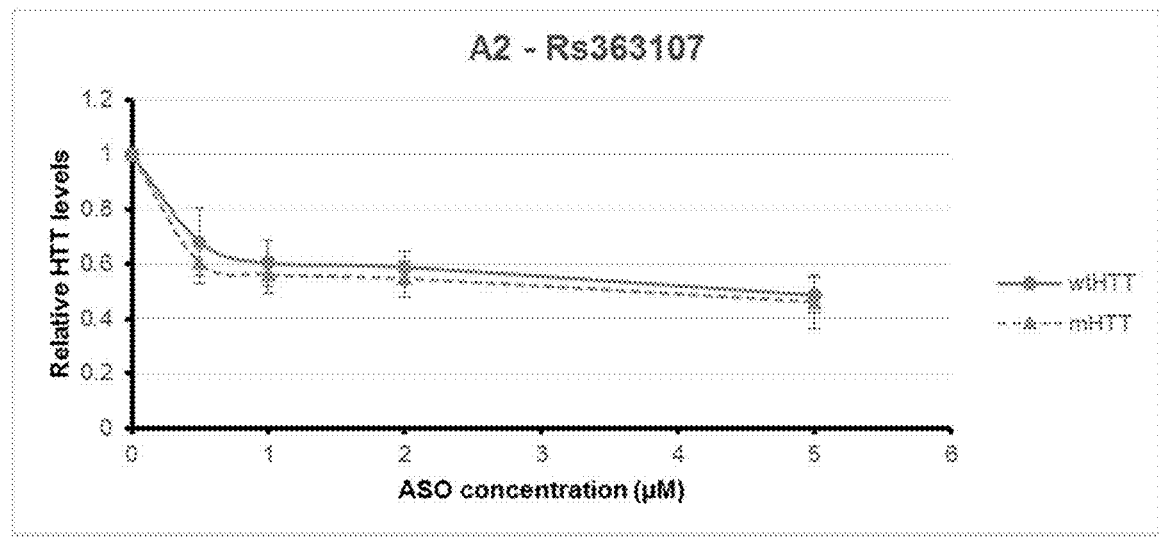
FIG. 7 shows that active transfection of patient-derived lymphoblasts with a rs363107-complementary ASO reduces mutant HTT protein. HD patient-derived lymphoblasts (A2/C haplotypes; CAG lengths 44/18) treated with a 4-9-4 LNA/phosphorothioate backbone gapmer with sequence +T*+A*+T*+A*T*T*T*T*C*A*A*A*G*+A*+T*+C*+A (*=phosphorothioate linkages, +=LNA) (SEQ ID NO: 163) show a dose-dependent reduction of mutant HTT protein relative to untreated controls. Cells were treated with either 0.5, 1, 2 or 5 μM of ASO or left untreated for 120 hrs and harvested for western blot analysis. Mutant and wild type huntingtin were separated on a 7% low-bis gel and band intensities were quantified by densitometry. Non-muscle myosin was used a loading/normalization control. Relative huntingtin levels are presented on the graph below. N=3, error bars represent standard error.
Figure 8:
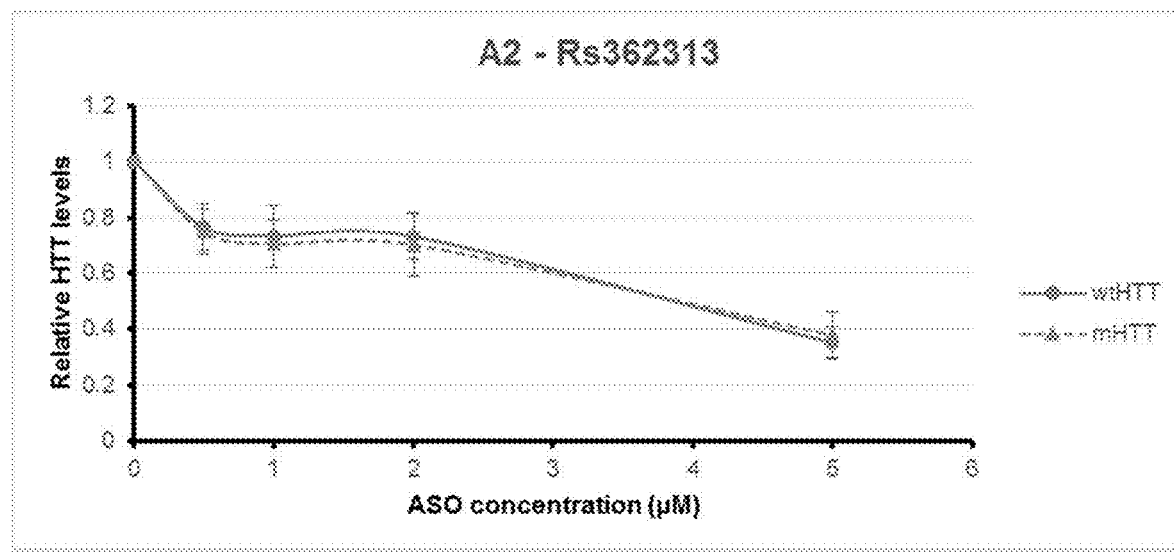
FIG. 8 shows that active transfection of patient-derived lymphoblasts with a rs362313-complementary ASO reduces mutant HTT protein. HD patient-derived lymphoblasts (A2/C haplotypes; CAG lengths 44/18) treated with a 4-9-4 LNA/phosphorothioate backbone gapmer with the sequence +A*+A*+G*+A*C*A*T*C*A*C*T*G*T*+G*+A*+A*+G (*=phosphorothioate linkages, +=LNA) (SEQ ID NO: 268) show a dose-dependent reduction of mutant HTT protein relative to untreated controls. Cells were treated with either 0.5, 1, 2 or 5 μM of ASO or left untreated for 120 hrs and harvested for western blot analysis. Mutant and wild type huntingtin were separated on a 7% low-bis gel and band intensities were quantified by densitometry. Non-muscle myosin was used a loading/normalization control. Relative huntingtin levels are presented on the graph below. N=4, error bars represent standard error.

We sought to evaluate the potential of rs363107, rs362313 and rs2530595 as HTT silencing targets using ASOs directed to these mutant sequences. Specifically, rs36107 was targeted with a locked nucleic acid (LNA)/phosphorothioate backbone gapmer with sequence +T*+A*+T*+A*T*T*T*T*C*A*A*A*G*+A*+T*+C*+A (*=phosphorothioate linkages, +=LNA) (SEQ ID NO: 163); rs362313 was targeted with a locked nucleic acid (LNA)/phosphorothioate backbone gapmer with sequence +A*+A*+G*+A*C*A*T*C*A*C*T*G*T*+G*+A*+A*+G (*=phosphorothioate linkages, +=LNA) (SEQ ID NO: 268); and rs2530595 was targeted with a locked nucleic acid (LNA)/phosphorothioate backbone gapmer with sequence +T*+C*+C*+T*C*C*C*C*A*C*A*G*A*+G*+G*+G*+A (*=phosphorothioate linkages, +=LNA) (SEQ ID NO: 373). Human HD lymphoblasts bearing the A2/C haplotype (GM02150, CAG lengths 44/18) were treated with the LNA gapmer sequences at 0.5, 1, 2 and 5 µM for 120 hrs and harvested for Western blot analysis. As shown in FIGS. 6, 7 and 8, Western blot analysis using allelic separation of CAG 44/18 bands revealed reductions of mutant HTT at the protein level for all three LNA gapmer sequences. In summary, targeting the A2-specific polymorphisms (rs363107, rs362313 and rs2530595) with complementary ASOs can silence mutant HTT protein in cells genetically representative of HD patients bearing the A2 haplotype.

Example 8

ASOs Silence HTT A3a in Human Cells

Figure 9:
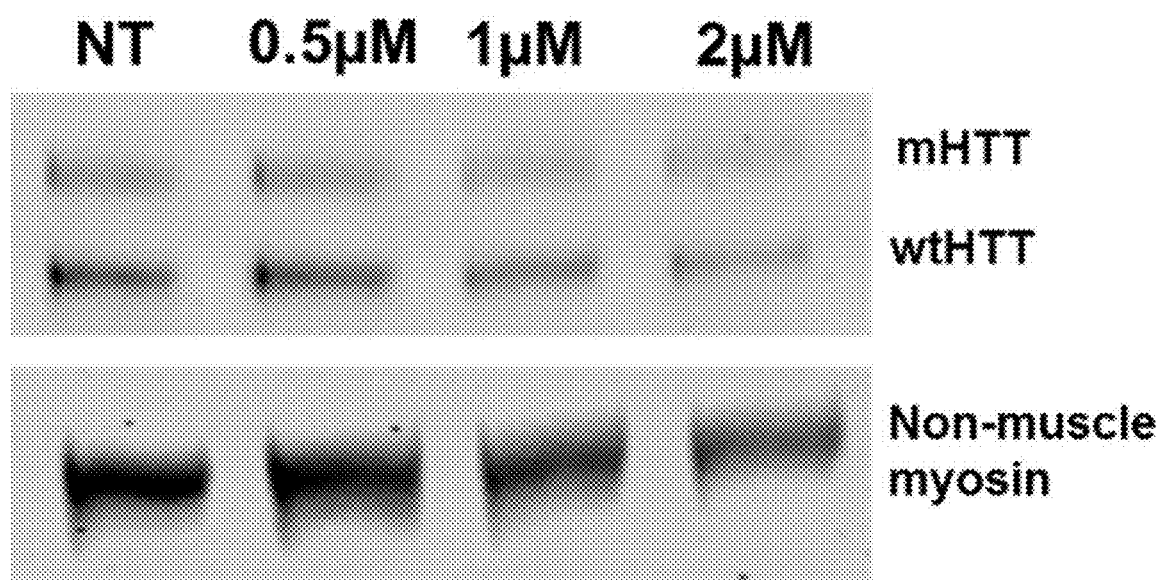
FIG. 9 shows that active transfection of patient-derived lymphoblasts with a rs113407847-complementary ASO reduces mutant HTT protein. HD patient-derived lymphoblasts (A3a/C haplotypes; CAG lengths 67/15) treated with a 4-9-4 LNA/phosphorothioate backbone gapmer with the sequence +C*+T*+C*+C*C*C*A*C*C*T*C*C*C*+G*+G*+C*+C (*=phosphorothioate linkages, +=LNA) (SEQ ID NO: 478) show a dose-dependent reduction of mutant HTT protein relative to untreated controls. Cells were treated with either 0.5, 1, 2 or 5 μM of ASO or left untreated for 120 hrs and harvested for western blot analysis. Mutant and wild type huntingtin were separated on a 7% low-bis gel and band intensities were quantified by densitometry. Non-muscle myosin was used a loading/normalization control. Relative huntingtin levels are presented on the graph below. N=4, error bars represent standard error.
Figure 9:
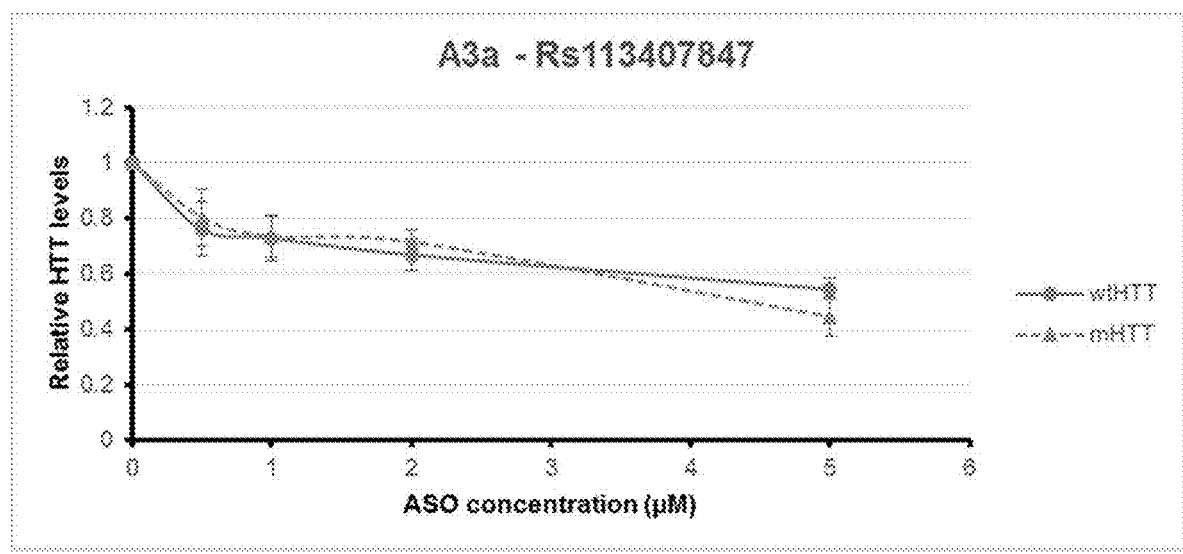

We sought to evaluate the potential of rs113407847 as a selective HTT silencing target using ASO directed to the mutant sequence. Human HD lymphoblasts bearing the A3a/C haplotypes (GM04724, CAG lengths 67/15) were treated with a 4-9-4 locked nucleic acid (LNA)/phosphorothioate backbone gapmer with sequence +C*+T*+C*+C*C*C*A*C*C*T*C*C*C*+G*+G*+C*+C (*=phosphorothioate linkages, +=LNA) (SEQ ID NO: 478) at 0.5, 1, 2 and 5 µM for 120 hrs and harvested for Western blot analysis. As shown in FIG. 9, Western blot analysis using allelic separation of CAG 67/15 bands revealed a dose-dependent reduction of mutant HTT at the protein level. Targeting the A3a-specific rs113407847 with complementary ASOs can reduce the level of the mutant HTT protein in cells genetically representative of HD patients bearing the A3a haplotype.

Discussion

The translation of allele-specific HTT silencing to therapeutic application requires clarity as to which transcribed SNPs are the most useful targets in the HD patient population. The frequency of specific polymorphic targets is known to vary between clinical cohorts, while secondary and tertiary targets that maximize the total number of patients treatable have been incompletely described. Our study provides the first comprehensive heterozygosity estimates across the HTT transcript in multiple patient populations, identifying specific allele targets of highest priority for development of selective antisense therapies. We have fully described the most common gene-spanning haplotypes relevant for selective suppression of mutant HTT in patients of European ancestry—A1, A2, and A3a—and identify all common polymorphisms specific for these haplotypes. In four different patient populations, these gene-spanning haplotypes represent panels of allele-specific targets that would achieve treatment of the greatest proportion of HD patients. We show that as few as three gene silencing reagents targeting the A1, A2, and A3a haplotypes may offer allele-specific HTT silencing therapy for 80% of all patients of European descent. A1 may be silenced using one of three defining polymorphisms, and A2 using one of five defining polymorphisms. If only one allele target can be chosen for development, silencing the A haplogroup by rs2298969 may offer treatment in the greatest proportion of patients. But when two targets are considered additively, A1 and A2 targets in combination allow for treatment of the majority of patients in all four major populations evaluated in this study. When three targets are considered, no combination of intragenic polymorphisms allows for selective silencing in a greater proportion of cases than defining polymorphisms of the A1, A2, and A3a haplotypes. A1 and A2 haplotypes therefore represent sets of priority targets for preclinical evaluation of allele-specific HTT silencing reagents, with rs113407847 a priority tertiary candidate.

Expansion of the CAG repeat has been shown to occur on multiple haplotypes in different Caucasian populations [22, 24]. Here we demonstrate that three intragenic HTT haplotypes, identical across four different populations of European ancestry, account for approximately 90% of HD chromosomes across these groups. This suggests that haplotypes on which repeated CAG expansion events occur are ancestral to all individuals of European descent, and may perhaps be shared by other related populations. The Δ2642 codon deletion (rs149109767), identified here as an exclusive marker of the A1 haplotype, has been observed in HD patients and controls from India [32] whereas A1 is entirely absent among both HD and control chromosomes of black South Africans and East Asians where prevalence of HD is dramatically lower [28, 29]. This suggests that association of the A1 haplotype with HD may occur in all populations of Indo-European ancestry, spanning South Asia, Europe, and American populations of European descent. The frequency of HD on A1, A2, and A3a haplotypes requires detailed haplotype analysis in patient populations from the Middle East, Central Asia, South Asia, and Africa to evaluate the global therapeutic impact of these targets. The high prevalence of expanded CAG on A1, A2, and A3a among all patient populations of European descent, and the presence of these haplotypes in other ancestrally related populations, suggests that these haplotypes may allow allele-specific silencing in the maximum proportion of patients worldwide.

In summary, we show that HTT is defined by a gene-spanning haplotype block in populations of European descent, and that specific sets of SNPs define gene-spanning haplotypes in both HD patients and controls. To our knowledge, this is the first annotation of dense haplotypes encompassing the HTT gene using whole-genome sequencing data. We identify and validate all polymorphisms specific for the three most common HD haplotypes, comprising >90% of HD chromosomes in four distinct populations of European ancestry. The defining polymorphisms of these haplotypes constitute optimal targets for development of allele-specific silencing compounds. Targetable HTT haplotypes revealed by this study represent a crucial step toward that objective, and toward safe gene silencing treatment of the greatest number of HD patients.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings.

REFERENCES

1. *A novel gene containing a trinucleotide repeat that is expanded and unstable on Huntington's disease chromosomes. The Huntington's Disease Collaborative Research Group.* Cell, 1993. 72(6): p. 971-983.
2. Kremer, B., et al., *A Worldwide Study of the Huntington's Disease Mutation: The Sensitivity and Specificity of Measuring CAG Repeats.* New England Journal of Medicine, 1994. 330(20): p. 1401-1406.
3. Rubinsztein, D. C., et al., *Phenotypic Characterization of Individuals with 30-40 CAG Repeats in the Huntington Disease (HD) Gene Reveals HD Cases with 36 Repeats and Apparently Normal Elderly Individuals with 36-39 Repeats.* American Journal of Human Genetics, 1996. 59(1): p. 16-22.
4. Zuccato, C., M. Valenza, and E. Cattaneo, *Molecular Mechanisms and Potential Therapeutical Targets in Huntington's Disease.* Physiological Reviews, 2010. 90(3): p. 905-981.
5. Southwell, A. L., et al., *Antisense oligonucleotide therapeutics for inherited neurodegenerative diseases.* Trends in Molecular Medicine, 2012. 18(11): p. 634-643.
6. Yamamoto, A., J. J. Lucas, and R. Hen, *Reversal of Neuropathology and Motor Dysfunction in a Conditional Model of Huntington's Disease.* Cell, 2000. 101(1): p. 57-66.
7. Kordasiewicz, H. B., et al., *Sustained Therapeutic Reversal of Huntington's Disease by Transient Repression of Huntingtin Synthesis.* Neuron, 2012. 74(6): p. 1031-1044.
8. Harper, S. Q., et al., *RNA interference improves motor and neuropathological abnormalities in a Huntington's disease mouse model.* PNAS, 2005. 102(16): p. 5820-5825.
9. Rodriguez-Lebron, E., et al., *Intrastriatal rAAV-mediated delivery of anti-huntingtin shRNAs induces partial reversal of disease progression in R6/1Huntington's disease transgenic mice.* Mol Ther, 2005. 12(4): p. 618-633.
10. Nasir, J., et al., *Targeted disruption of the Huntington's disease gene results in embryonic lethality and behavioral and morphological changes in heterozygotes.* Cell, 1995. 81(5): p. 811-823.
11. Duyao, M. P., et al., *Inactivation of the Mouse Huntington's Disease Gene Homolog Hdh.* Science, 1995. 269 (5222): p. 407-410.
12. Zeitlin, S., et al., *Increased apoptosis and early embryonic lethality in mice nullizygous for the Huntington's disease gene homologue.* Nature Genetics, 1995. 11(2): p. 155-163.
13. Auerbach, W., et al., *The HD mutation causes progressive lethal neurological disease in mice expressing reduced levels of huntingtin.* Human Molecular Genetics, 2001. 10(22): p. 2515-23.
14. Sah, D. W. Y. and N. Aronin, *Oligonucleotide therapeutic approaches for Huntington disease.* The Journal of Clinical Investigation, 2011. 121(2): p. 500-507.
15. Kay, C., et al., *Personalized gene silencing therapeutics for Huntington disease.* Clinical Genetics, 2014. 86(1): p. 29-36.
16. Yu, D., et al., *Single-Stranded RNAs Use RNAi to Potently and Allele-Selectively Inhibit Mutant Huntingtin Expression.* Cell, 2012. 150(5): p. 895-908.
17. Fiszer, A., et al., *Self-duplexing CUG repeats selectively inhibit mutant huntingtin expression.* Nucleic Acids Res, 2013. 41(22): p. 10426-37.
18. Carroll, J. B., et al., *Potent and Selective Antisense Oligonucleotides Targeting Single-Nucleotide Polymorphisms in the Huntington Disease Gene/Allele-Specific Silencing of Mutant Huntingtin.* Mol Ther, 2011. 19: p. 2178-2185.
19. Southwell, A. L., et al., *In vivo evaluation of candidate allele-specific mutant huntingtin gene silencing antisense oligonucleotides.* Mol Ther, 2014.
20. Ostergaard, M. E., et al., *Rational design of antisense oligonucleotides targeting single nucleotide polymorphisms for potent and allele selective suppression of mutant Huntingtin in the CNS.* Nucleic Acids Res, 2013. 41(21): p. 9634-50.
21. Zhang, Y., J. Engelman, and R. M. Friedlander, *Allele-specific silencing of mutant Huntington's disease gene.* Journal of Neurochemistry, 2009. 108(1): p. 82-90.
22. Lee, J.-M., et al., *Common SNP-Based Haplotype Analysis of the 4p16.3 Huntington Disease Gene Region.* American Journal of Human Genetics, 2012. 90(3): p. 434-444.
23. Novelletto, A., et al., *Analysis of the trinucleotide repeat expansion in Italian families affected with Huntington disease.* Human Molecular Genetics, 1994. 3(1): p. 93-8.

24. Warby, S. C., et al., *CAG expansion in the Huntington disease gene is associated with a specific and targetable predisposing haplogroup*. American Journal of Human Genetics, 2009. 84(3): p. 351-366.
25. Skotte, N. H., et al., *Allele-specific suppression of mutant huntingtin using antisense oligonucleotides: providing a therapeutic option for all Huntington disease patients*. PLoS One, 2014. 9(9): p. e107434.
26. Slow, E. J., et al., *Selective striatal neuronal loss in a YAC128 mouse model of Huntington disease*. Hum Mol Genet, 2003. 12(13): p. 1555-67.
27. Abecasis, G. R., et al., *An integrated map of genetic variation from 1,092 human genomes*. Nature, 2012. 491(7422): p. 56-65.
28. Baine, F. K., et al., *Huntington disease in the South African population occurs on diverse and ethnically distinct genetic haplotypes*. European Journal of Human Genetics, 2013. 21(10): p. 1120-7.
29. Warby, S. C., et al., *HTT haplotypes contribute to differences in Huntington disease prevalence between Europe and East Asia*. European Journal of Human Genetics, 2011. 19(5): p. 561-566.
30. Pfister, E. L., et al., *Five siRNAs Targeting Three SNPs May Provide Therapy for Three-Quarters of Huntington's Disease Patients*. Current Biology, 2009. 19(9): p. 774-778.
31. Bennett, C. F. and E. E. Swayze, *RNA targeting therapeutics: molecular mechanisms of antisense oligonucleotides as a therapeutic platform*. Annual Review of Pharmacology and Toxicology, 2010. 50: p. 259-293.
32. Saleem, Q., et al., *Molecular analysis of Huntington's disease and linked polymorphisms in the Indian population*. Acta Neurologica Scandinavica, 2003. 108(4): p. 281-6.

The invention claimed is:

1. An oligomer of between 10-30 nucleobases in length which comprises a contiguous nucleotide sequence of a total of between 10-26 nucleotides, wherein the contiguous nucleotide sequence is targeted to hybridize to a sequence selected from the group consisting of:

(SEQ ID NO: 522)
5'-TGACAGTTGTATTTTTGTTTGTGA{CACG}TATTATCTGTTAAAACATT

TTC-3';

(SEQ ID NO: 523)
5'-TCTTAAACTTTTAAATGCCATTTGATCTTT{G}AAAATATATGTTTAA

TAGTGTATTTTAAG-3';

(SEQ ID NO: 524)
5'-CCCTCAGCGAGCAAGTCAAGCTCTTCACAG{T}GATGTCTTACAAGCGC

AGAGGGCTCTGTGA-3';

(SEQ ID NO: 525)
5'-GCTTTGTCCCTCCCCCGCTTCCTCCCTCTG{T}GGGGAGGACCCGGGAC

CACAGCTGCTGGCC-3';
and (SEQ ID NO: 526)
5'-GGAGAGACTCCACTCTGAATGGGCCGGGA{G}GTGGGGAGGACTCCAT

TTCAGATGGGGTCG-3';

wherein the oligomer targets the bracketed nucleotide(s) without mismatches, permits between 0-3 mismatches over the remainder of the target sequence and reduces mutant Huntingtin (HTT) mRNA or mutant HTT protein in a cell or tissue; and wherein the oligomer is modified.

2. The oligomer of claim 1, wherein the oligomer is selected from SEQ ID NOs: 6-10.

3. The oligomer of claim 1, wherein the oligomer is selected from SEQ ID NOs: 11-517.

4. The oligomer of claim 1, wherein the oligomer has a sequence selected from the group consisting of:

(SEQ ID NO: 36)
5'-GATAATACGTGTCACAAAC-3';

(SEQ ID NO: 66)
5'-ATAATACGTGTCACAAA-3';

(SEQ ID NO: 92)
5'-TAATACGTGTCACAA-3';

(SEQ ID NO: 163)
5'-TATATTTTCAAAGATCA-3';

(SEQ ID NO: 268)
5'-AAGACATCACTGTGAAG-3';

(SEQ ID NO: 373)
5'-TCCTCCCCACAGAGGGA-3';
and (SEQ ID NO: 478)
5'-CTCCCCACCTCCCGGCC-3'.

5. The oligomer of claim 1, wherein the contiguous nucleotide sequence comprises nucleotide analogues.

6. The oligomer of claim 1, wherein the oligomer has a modified internucleoside linkage.

7. The oligomer of claim 6, wherein the modified internucleoside linkage is a peptide-nucleic acid linkage, a morpholino linkage, a N3' to P5' phosphoramidate linkage, a methylphosphonate linkage or a phosphorothioate linkage.

8. The oligomer of claim 1, wherein the oligomer has one or more modified sugar moiety.

9. The oligomer of claim 8, wherein the modified sugar moiety is 2'-O-alkyl oligoribonucleotide.

10. The oligomer of claim 1, wherein the oligomer is a gapmer.

11. The oligomer of claim 9, wherein the oligomer has a 2'MOE gapmer modification.

12. The oligomer of claim 1, wherein the oligomer has a modified nucleobase.

13. The oligomer of claim 12, wherein the modified nucleobase is a 5-methyl pyrimidine or a 5-propynyl pyrimidine.

14. The oligomer of claim 8, wherein the one or more nucleotide analogues comprise locked nucleic acids (LNA) units.

15. The oligomer according to claim 13, wherein the LNA units consist of beta-D-oxy-LNA monomers.

16. A pharmaceutical composition comprising the oligomer of claim 1 and a pharmaceutically acceptable diluent, carrier, salt or adjuvant.

17. A commercial package, comprising:
an oligomer of claim 1; and
instructions for the treatment of HD.

18. The oligomer of claim 2, wherein the oligomer has a modified internucleoside linkage.

19. The oligomer of claim 3, wherein the oligomer has a modified internucleoside linkage.

20. The oligomer of claim 4, wherein the oligomer has a modified internucleoside linkage.

21. The oligomer of claim 5, wherein the oligomer has a modified internucleoside linkage.

22. The oligomer of claim 18, wherein the modified internucleoside linkage is a peptide-nucleic acid linkage, a morpholino linkage, a N3' to P5' phosphoramidate linkage, a methylphosphonate linkage or a phosphorothioate linkage.

23. The oligomer of claim 19, wherein the modified internucleoside linkage is a peptide-nucleic acid linkage, a morpholino linkage, a N3' to P5' phosphoramidate linkage, a methylphosphonate linkage or a phosphorothioate linkage.

24. The oligomer of claim 20, wherein the modified internucleoside linkage is a peptide-nucleic acid linkage, a morpholino linkage, a N3' to P5' phosphoramidate linkage, a methylphosphonate linkage or a phosphorothioate linkage.

25. The oligomer of claim 21, wherein the modified internucleoside linkage is a peptide-nucleic acid linkage, a morpholino linkage, a N3' to P5' phosphoramidate linkage, a methylphosphonate linkage or a phosphorothioate linkage.

26. The oligomer of claim 2, wherein the oligomer has one or more modified sugar moiety.

27. The oligomer of claim 3, wherein the oligomer has one or more modified sugar moiety.

28. The oligomer of claim 4, wherein the oligomer has one or more modified sugar moiety.

29. The oligomer of claim 5, wherein the oligomer has one or more modified sugar moiety.

30. The oligomer of claim 26, wherein the modified sugar moiety is 2'-O-alkyl oligoribonucleotide.

31. The oligomer of claim 27, wherein the modified sugar moiety is 2'-O-alkyl oligoribonucleotide.

32. The oligomer of claim 28, wherein the modified sugar moiety is 2'-O-alkyl oligoribonucleotide.

33. The oligomer of claim 29, wherein the modified sugar moiety is 2'-O-alkyl oligoribonucleotide.

34. The oligomer according to claim 14, wherein the LNA units consist of beta-D-oxy-LNA monomers.

* * * * *

```
                         SEQUENCE LISTING

<160> NUMBER OF SEQ ID NOS: 527

<210> SEQ ID NO 1
<211> LENGTH: 50
<212> TYPE: DNA
<213> ORGANISM: Homo sapiens

<400> SEQUENCE: 1
tgacagttgt attttttgttt gtgacacgta ttatctgtta aaacattttc            50

<210> SEQ ID NO 2
<211> LENGTH: 61
<212> TYPE: DNA
<213> ORGANISM: Homo sapiens

<400> SEQUENCE: 2
tcttaaactt taaatgcca tttgatcttt raaaatatat gttttaatag tgtattttaa    60
g                                                                  61

<210> SEQ ID NO 3
<211> LENGTH: 61
<212> TYPE: DNA
<213> ORGANISM: Homo sapiens

<400> SEQUENCE: 3
ccctcagcga gcaagtcaag ctcttcacag ygatgtctta caagcgcaga gggctctgtg   60
a                                                                  61

<210> SEQ ID NO 4
<211> LENGTH: 61
<212> TYPE: DNA
<213> ORGANISM: Homo sapiens

<400> SEQUENCE: 4
gctttgtccc tcccccgctt cctccctctg ygggaggac ccgggaccac agctgctggc   60
c                                                                  61

<210> SEQ ID NO 5
<211> LENGTH: 61
<212> TYPE: DNA
<213> ORGANISM: Homo sapiens

<400> SEQUENCE: 5
ggagagactc cactctgaat ggggccggga rgtggggagg actccatttc agatggggtc   60
```

```
                                                  g                                                           61

<210> SEQ ID NO 6
<211> LENGTH: 50
<212> TYPE: DNA
<213> ORGANISM: Homo sapiens

<400> SEQUENCE: 6
gaaaatgttt taacagataa tacgtgtcac aaacaaaaat acaactgtca              50

<210> SEQ ID NO 7
<211> LENGTH: 61
<212> TYPE: DNA
<213> ORGANISM: Homo sapiens

<400> SEQUENCE: 7
cttaaaatac actattaaaa catatatttt caaagatcaa atggcattta aaagtttaag   60
a                                                                  61

<210> SEQ ID NO 8
<211> LENGTH: 61
<212> TYPE: DNA
<213> ORGANISM: Homo sapiens

<400> SEQUENCE: 8
tcacagagcc ctctgcgctt gtaagacatc actgtgaaga gcttgacttg ctcgctgagg   60
g                                                                  61

<210> SEQ ID NO 9
<211> LENGTH: 61
<212> TYPE: DNA
<213> ORGANISM: Homo sapiens

<400> SEQUENCE: 9
ggccagcagc tgtggtcccg ggtcctcccc acagagggag gaagcggggg agggacaaag   60
c                                                                  61

<210> SEQ ID NO 10
<211> LENGTH: 61
<212> TYPE: DNA
<213> ORGANISM: Homo sapiens

<400> SEQUENCE: 10 cgacccatc tgaaatggag tcctccccac ctcccggccc cattcagagt ggagtctctc    60
c                                                                  61

<210> SEQ ID NO 11
<211> LENGTH: 20
<212> TYPE: DNA
<213> ORGANISM: Homo sapiens

<400> SEQUENCE: 11
gttttaacag ataatacgtg                                              20

<210> SEQ ID NO 12
<211> LENGTH: 20
<212> TYPE: DNA
<213> ORGANISM: Homo sapiens

<400> SEQUENCE: 12
```
ttttaacaga taatacgtgt                                            20

<210> SEQ ID NO 13
<211> LENGTH: 20
<212> TYPE: DNA
<213> ORGANISM: Homo sapiens

<400> SEQUENCE: 13
tttaacagat aatacgtgtc                                            20

<210> SEQ ID NO 14
<211> LENGTH: 20
<212> TYPE: DNA
<213> ORGANISM: Homo sapiens

<400> SEQUENCE: 14
ttaacagata atacgtgtca                                            20

<210> SEQ ID NO 15
<211> LENGTH: 20
<212> TYPE: DNA
<213> ORGANISM: Homo sapiens

<400> SEQUENCE: 15
taacagataa tacgtgtcac                                            20

<210> SEQ ID NO 16
<211> LENGTH: 20
<212> TYPE: DNA
<213> ORGANISM: Homo sapiens

<400> SEQUENCE: 16
aacagataat acgtgtcaca                                            20

<210> SEQ ID NO 17
<211> LENGTH: 20
<212> TYPE: DNA
<213> ORGANISM: Homo sapiens

<400> SEQUENCE: 17
acagataata cgtgtcacaa                                            20

<210> SEQ ID NO 18
<211> LENGTH: 20
<212> TYPE: DNA
<213> ORGANISM: Homo sapiens

<400> SEQUENCE: 18
cagataatac gtgtcacaaa                                            20

<210> SEQ ID NO 19
<211> LENGTH: 20
<212> TYPE: DNA
<213> ORGANISM: Homo sapiens

<400> SEQUENCE: 19
agataatacg tgtcacaaac                                            20

<210> SEQ ID NO 20
<211> LENGTH: 20
<212> TYPE: DNA
<213> ORGANISM: Homo sapiens

<400> SEQUENCE: 20
gataatacgt gtcacaaaca                                              20

<210> SEQ ID NO 21
<211> LENGTH: 20
<212> TYPE: DNA
<213> ORGANISM: Homo sapiens

<400> SEQUENCE: 21
ataatacgtg tcacaaacaa                                              20

<210> SEQ ID NO 22
<211> LENGTH: 20
<212> TYPE: DNA
<213> ORGANISM: Homo sapiens

<400> SEQUENCE: 22
taatacgtgt cacaaacaaa                                              20

<210> SEQ ID NO 23
<211> LENGTH: 20
<212> TYPE: DNA
<213> ORGANISM: Homo sapiens

<400> SEQUENCE: 23
aatacgtgtc acaaacaaaa                                              20

<210> SEQ ID NO 24
<211> LENGTH: 20
<212> TYPE: DNA
<213> ORGANISM: Homo sapiens

<400> SEQUENCE: 24
atacgtgtca caaacaaaaa                                              20

<210> SEQ ID NO 25
<211> LENGTH: 20
<212> TYPE: DNA
<213> ORGANISM: Homo sapiens

<400> SEQUENCE: 25
tacgtgtcac aaacaaaaat                                              20

<210> SEQ ID NO 26
<211> LENGTH: 20
<212> TYPE: DNA
<213> ORGANISM: Homo sapiens

<400> SEQUENCE: 26
acgtgtcaca aacaaaaata                                              20

<210> SEQ ID NO 27
<211> LENGTH: 20
<212> TYPE: DNA
<213> ORGANISM: Homo sapiens

<400> SEQUENCE: 27
cgtgtcacaa acaaaaatac                                              20

<210> SEQ ID NO 28
<211> LENGTH: 19
<212> TYPE: DNA
<213> ORGANISM: Homo sapiens

```
<400> SEQUENCE: 28
ttttaacaga taatacgtg                                                19

<210> SEQ ID NO 29
<211> LENGTH: 19
<212> TYPE: DNA
<213> ORGANISM: Homo sapiens

<400> SEQUENCE: 29
tttaacagat aatacgtgt                                                19

<210> SEQ ID NO 30
<211> LENGTH: 19
<212> TYPE: DNA
<213> ORGANISM: Homo sapiens

<400> SEQUENCE: 30
ttaacagata atacgtgtc                                                19

<210> SEQ ID NO 31
<211> LENGTH: 19
<212> TYPE: DNA
<213> ORGANISM: Homo sapiens

<400> SEQUENCE: 31
taacagataa tacgtgtca                                                19

<210> SEQ ID NO 32
<211> LENGTH: 19
<212> TYPE: DNA
<213> ORGANISM: Homo sapiens

<400> SEQUENCE: 32
aacagataat acgtgtcac                                                19

<210> SEQ ID NO 33
<211> LENGTH: 19
<212> TYPE: DNA
<213> ORGANISM: Homo sapiens

<400> SEQUENCE: 33
acagataata cgtgtcaca                                                19

<210> SEQ ID NO 34
<211> LENGTH: 19
<212> TYPE: DNA
<213> ORGANISM: Homo sapiens

<400> SEQUENCE: 34
cagataatac gtgtcacaa                                                19

<210> SEQ ID NO 35
<211> LENGTH: 19
<212> TYPE: DNA
<213> ORGANISM: Homo sapiens

<400> SEQUENCE: 35
agataatacg tgtcacaaa                                                19

<210> SEQ ID NO 36
<211> LENGTH: 19
<212> TYPE: DNA
<213> ORGANISM: Homo sapiens
```

```
<400> SEQUENCE: 36
gataatacgt gtcacaaac                                                19

<210> SEQ ID NO 37
<211> LENGTH: 19
<212> TYPE: DNA
<213> ORGANISM: Homo sapiens

<400> SEQUENCE: 37
ataatacgtg tcacaaaca                                                19

<210> SEQ ID NO 38
<211> LENGTH: 19
<212> TYPE: DNA
<213> ORGANISM: Homo sapiens

<400> SEQUENCE: 38
taatacgtgt cacaaacaa                                                19

<210> SEQ ID NO 39
<211> LENGTH: 19
<212> TYPE: DNA
<213> ORGANISM: Homo sapiens

<400> SEQUENCE: 39
aatacgtgtc acaaacaaa                                                19

<210> SEQ ID NO 40
<211> LENGTH: 19
<212> TYPE: DNA
<213> ORGANISM: Homo sapiens

<400> SEQUENCE: 40
atacgtgtca caaacaaaa                                                19

<210> SEQ ID NO 41
<211> LENGTH: 19
<212> TYPE: DNA
<213> ORGANISM: Homo sapiens

<400> SEQUENCE: 41
tacgtgtcac aaacaaaaa                                                19

<210> SEQ ID NO 42
<211> LENGTH: 19
<212> TYPE: DNA
<213> ORGANISM: Homo sapiens

<400> SEQUENCE: 42
acgtgtcaca aacaaaaat                                                19

<210> SEQ ID NO 43
<211> LENGTH: 19
<212> TYPE: DNA
<213> ORGANISM: Homo sapiens

<400> SEQUENCE: 43
cgtgtcacaa acaaaaata                                                19

<210> SEQ ID NO 44
<211> LENGTH: 18
<212> TYPE: DNA
```

```
<213> ORGANISM: Homo sapiens

<400> SEQUENCE: 44
tttaacagat aatacgtg                                                  18

<210> SEQ ID NO 45
<211> LENGTH: 18
<212> TYPE: DNA
<213> ORGANISM: Homo sapiens

<400> SEQUENCE: 45
ttaacagata atacgtgt                                                  18

<210> SEQ ID NO 46
<211> LENGTH: 18
<212> TYPE: DNA
<213> ORGANISM: Homo sapiens

<400> SEQUENCE: 46
taacagataa tacgtgtc                                                  18

<210> SEQ ID NO 47
<211> LENGTH: 18
<212> TYPE: DNA
<213> ORGANISM: Homo sapiens

<400> SEQUENCE: 47
aacagataat acgtgtca                                                  18

<210> SEQ ID NO 48
<211> LENGTH: 18
<212> TYPE: DNA
<213> ORGANISM: Homo sapiens

<400> SEQUENCE: 48
acagataata cgtgtcac                                                  18

<210> SEQ ID NO 49
<211> LENGTH: 18
<212> TYPE: DNA
<213> ORGANISM: Homo sapiens

<400> SEQUENCE: 49
cagataatac gtgtcaca                                                  18

<210> SEQ ID NO 50
<211> LENGTH: 18
<212> TYPE: DNA
<213> ORGANISM: Homo sapiens

<400> SEQUENCE: 50
agataatacg tgtcacaa                                                  18

<210> SEQ ID NO 51
<211> LENGTH: 18
<212> TYPE: DNA
<213> ORGANISM: Homo sapiens

<400> SEQUENCE: 51
gataatacgt gtcacaaa                                                  18

<210> SEQ ID NO 52
<211> LENGTH: 18
```

```
<212> TYPE: DNA
<213> ORGANISM: Homo sapiens

<400> SEQUENCE: 52
ataatacgtg tcacaaac                                                      18

<210> SEQ ID NO 53
<211> LENGTH: 18
<212> TYPE: DNA
<213> ORGANISM: Homo sapiens

<400> SEQUENCE: 53
taatacgtgt cacaaaca                                                      18

<210> SEQ ID NO 54
<211> LENGTH: 18
<212> TYPE: DNA
<213> ORGANISM: Homo sapiens

<400> SEQUENCE: 54
aatacgtgtc acaaacaa                                                      18

<210> SEQ ID NO 55
<211> LENGTH: 18
<212> TYPE: DNA
<213> ORGANISM: Homo sapiens

<400> SEQUENCE: 55
atacgtgtca caaacaaa                                                      18

<210> SEQ ID NO 56
<211> LENGTH: 18
<212> TYPE: DNA
<213> ORGANISM: Homo sapiens

<400> SEQUENCE: 56
tacgtgtcac aaacaaaa                                                      18

<210> SEQ ID NO 57
<211> LENGTH: 18
<212> TYPE: DNA
<213> ORGANISM: Homo sapiens

<400> SEQUENCE: 57
acgtgtcaca aacaaaaa                                                      18

<210> SEQ ID NO 58
<211> LENGTH: 18
<212> TYPE: DNA
<213> ORGANISM: Homo sapiens

<400> SEQUENCE: 58
cgtgtcacaa acaaaaat                                                      18

<210> SEQ ID NO 59
<211> LENGTH: 17
<212> TYPE: DNA
<213> ORGANISM: Homo sapiens

<400> SEQUENCE: 59
ttaacagata atacgtg                                                       17

<210> SEQ ID NO 60
```

```
<211> LENGTH: 17
<212> TYPE: DNA
<213> ORGANISM: Homo sapiens

<400> SEQUENCE: 60
taacagataa tacgtgt                                                  17

<210> SEQ ID NO 61
<211> LENGTH: 17
<212> TYPE: DNA
<213> ORGANISM: Homo sapiens

<400> SEQUENCE: 61
aacagataat acgtgtc                                                  17

<210> SEQ ID NO 62
<211> LENGTH: 17
<212> TYPE: DNA
<213> ORGANISM: Homo sapiens

<400> SEQUENCE: 62
acagataata cgtgtca                                                  17

<210> SEQ ID NO 63
<211> LENGTH: 17
<212> TYPE: DNA
<213> ORGANISM: Homo sapiens

<400> SEQUENCE: 63
cagataatac gtgtcac                                                  17

<210> SEQ ID NO 64
<211> LENGTH: 17
<212> TYPE: DNA
<213> ORGANISM: Homo sapiens

<400> SEQUENCE: 64
agataatacg tgtcaca                                                  17

<210> SEQ ID NO 65
<211> LENGTH: 17
<212> TYPE: DNA
<213> ORGANISM: Homo sapiens

<400> SEQUENCE: 65
gataatacgt gtcacaa                                                  17

<210> SEQ ID NO 66
<211> LENGTH: 17
<212> TYPE: DNA
<213> ORGANISM: Homo sapiens

<400> SEQUENCE: 66
ataatacgtg tcacaaa                                                  17

<210> SEQ ID NO 67
<211> LENGTH: 17
<212> TYPE: DNA
<213> ORGANISM: Homo sapiens

<400> SEQUENCE: 67
taatacgtgt cacaaac                                                  17
```

```
<210> SEQ ID NO 68
<211> LENGTH: 17
<212> TYPE: DNA
<213> ORGANISM: Homo sapiens

<400> SEQUENCE: 68
aatacgtgtc acaaaca                                                17

<210> SEQ ID NO 69
<211> LENGTH: 17
<212> TYPE: DNA
<213> ORGANISM: Homo sapiens

<400> SEQUENCE: 69
atacgtgtca caaacaa                                                17

<210> SEQ ID NO 70
<211> LENGTH: 17
<212> TYPE: DNA
<213> ORGANISM: Homo sapiens

<400> SEQUENCE: 70
tacgtgtcac aaacaaa                                                17

<210> SEQ ID NO 71
<211> LENGTH: 17
<212> TYPE: DNA
<213> ORGANISM: Homo sapiens

<400> SEQUENCE: 71
acgtgtcaca aacaaaa                                                17

<210> SEQ ID NO 72
<211> LENGTH: 17
<212> TYPE: DNA
<213> ORGANISM: Homo sapiens

<400> SEQUENCE: 72
cgtgtcacaa acaaaaa                                                17

<210> SEQ ID NO 73
<211> LENGTH: 16
<212> TYPE: DNA
<213> ORGANISM: Homo sapiens

<400> SEQUENCE: 73
taacagataa tacgtg                                                 16

<210> SEQ ID NO 74
<211> LENGTH: 16
<212> TYPE: DNA
<213> ORGANISM: Homo sapiens

<400> SEQUENCE: 74
aacagataat acgtgt                                                 16

<210> SEQ ID NO 75
<211> LENGTH: 16
<212> TYPE: DNA
<213> ORGANISM: Homo sapiens

<400> SEQUENCE: 75
acagataata cgtgtc                                                 16
```

```
<210> SEQ ID NO 76
<211> LENGTH: 16
<212> TYPE: DNA
<213> ORGANISM: Homo sapiens

<400> SEQUENCE: 76
cagataatac gtgtca                                                     16

<210> SEQ ID NO 77
<211> LENGTH: 16
<212> TYPE: DNA
<213> ORGANISM: Homo sapiens

<400> SEQUENCE: 77
agataatacg tgtcac                                                     16

<210> SEQ ID NO 78
<211> LENGTH: 16
<212> TYPE: DNA
<213> ORGANISM: Homo sapiens

<400> SEQUENCE: 78
gataatacgt gtcaca                                                     16

<210> SEQ ID NO 79
<211> LENGTH: 16
<212> TYPE: DNA
<213> ORGANISM: Homo sapiens

<400> SEQUENCE: 79
ataatacgtg tcacaa                                                     16

<210> SEQ ID NO 80
<211> LENGTH: 16
<212> TYPE: DNA
<213> ORGANISM: Homo sapiens

<400> SEQUENCE: 80
taatacgtgt cacaaa                                                     16

<210> SEQ ID NO 81
<211> LENGTH: 16
<212> TYPE: DNA
<213> ORGANISM: Homo sapiens

<400> SEQUENCE: 81
aatacgtgtc acaaac                                                     16

<210> SEQ ID NO 82
<211> LENGTH: 16
<212> TYPE: DNA
<213> ORGANISM: Homo sapiens

<400> SEQUENCE: 82
atacgtgtca caaaca                                                     16

<210> SEQ ID NO 83
<211> LENGTH: 16
<212> TYPE: DNA
<213> ORGANISM: Homo sapiens

<400> SEQUENCE: 83
tacgtgtcac aaacaa                                                     16
```

```
<210> SEQ ID NO 84
<211> LENGTH: 16
<212> TYPE: DNA
<213> ORGANISM: Homo sapiens

<400> SEQUENCE: 84
acgtgtcaca aacaaa                                                  16

<210> SEQ ID NO 85
<211> LENGTH: 16
<212> TYPE: DNA
<213> ORGANISM: Homo sapiens

<400> SEQUENCE: 85
cgtgtcacaa acaaaa                                                  16

<210> SEQ ID NO 86
<211> LENGTH: 15
<212> TYPE: DNA
<213> ORGANISM: Homo sapiens

<400> SEQUENCE: 86
aacagataat acgtg                                                   15

<210> SEQ ID NO 87
<211> LENGTH: 15
<212> TYPE: DNA
<213> ORGANISM: Homo sapiens

<400> SEQUENCE: 87
acagataata cgtgt                                                   15

<210> SEQ ID NO 88
<211> LENGTH: 15
<212> TYPE: DNA
<213> ORGANISM: Homo sapiens

<400> SEQUENCE: 88
cagataatac gtgtc                                                   15

<210> SEQ ID NO 89
<211> LENGTH: 15
<212> TYPE: DNA
<213> ORGANISM: Homo sapiens

<400> SEQUENCE: 89
agataatacg tgtca                                                   15

<210> SEQ ID NO 90
<211> LENGTH: 15
<212> TYPE: DNA
<213> ORGANISM: Homo sapiens

<400> SEQUENCE: 90
gataatacgt gtcac                                                   15

<210> SEQ ID NO 91
<211> LENGTH: 15
<212> TYPE: DNA
<213> ORGANISM: Homo sapiens

<400> SEQUENCE: 91
```
ataatacgtg tcaca                                              15

<210> SEQ ID NO 92
<211> LENGTH: 15
<212> TYPE: DNA
<213> ORGANISM: Homo sapiens

<400> SEQUENCE: 92
taatacgtgt cacaa                                              15

<210> SEQ ID NO 93
<211> LENGTH: 15
<212> TYPE: DNA
<213> ORGANISM: Homo sapiens

<400> SEQUENCE: 93
aatacgtgtc acaaa                                              15

<210> SEQ ID NO 94
<211> LENGTH: 15
<212> TYPE: DNA
<213> ORGANISM: Homo sapiens

<400> SEQUENCE: 94
atacgtgtca caaac                                              15

<210> SEQ ID NO 95
<211> LENGTH: 15
<212> TYPE: DNA
<213> ORGANISM: Homo sapiens

<400> SEQUENCE: 95
tacgtgtcac aaaca                                              15

<210> SEQ ID NO 96
<211> LENGTH: 15
<212> TYPE: DNA
<213> ORGANISM: Homo sapiens

<400> SEQUENCE: 96
acgtgtcaca aacaa                                              15

<210> SEQ ID NO 97
<211> LENGTH: 15
<212> TYPE: DNA
<213> ORGANISM: Homo sapiens

<400> SEQUENCE: 97
cgtgtcacaa acaaa                                              15

<210> SEQ ID NO 98
<211> LENGTH: 20
<212> TYPE: DNA
<213> ORGANISM: Homo sapiens

<400> SEQUENCE: 98
ctattaaaac atatattttc                                         20

<210> SEQ ID NO 99
<211> LENGTH: 20
<212> TYPE: DNA
<213> ORGANISM: Homo sapiens

<400> SEQUENCE: 99
tattaaaaca tatattttca                                                     20

<210> SEQ ID NO 100
<211> LENGTH: 20
<212> TYPE: DNA
<213> ORGANISM: Homo sapiens

<400> SEQUENCE: 100
attaaaacat atattttcaa                                                     20

<210> SEQ ID NO 101
<211> LENGTH: 20
<212> TYPE: DNA
<213> ORGANISM: Homo sapiens

<400> SEQUENCE: 101
ttaaaacata tattttcaaa                                                     20

<210> SEQ ID NO 102
<211> LENGTH: 20
<212> TYPE: DNA
<213> ORGANISM: Homo sapiens

<400> SEQUENCE: 102
taaaacatat attttcaaag                                                     20

<210> SEQ ID NO 103
<211> LENGTH: 20
<212> TYPE: DNA
<213> ORGANISM: Homo sapiens

<400> SEQUENCE: 103
aaaacatata ttttcaaaga                                                     20

<210> SEQ ID NO 104
<211> LENGTH: 20
<212> TYPE: DNA
<213> ORGANISM: Homo sapiens

<400> SEQUENCE: 104
aaacatatat tttcaaagat                                                     20

<210> SEQ ID NO 105
<211> LENGTH: 20
<212> TYPE: DNA
<213> ORGANISM: Homo sapiens

<400> SEQUENCE: 105
aacatatatt ttcaaagatc                                                     20

<210> SEQ ID NO 106
<211> LENGTH: 20
<212> TYPE: DNA
<213> ORGANISM: Homo sapiens

<400> SEQUENCE: 106
acatatattt tcaaagatca                                                     20

<210> SEQ ID NO 107
<211> LENGTH: 20
<212> TYPE: DNA
<213> ORGANISM: Homo sapiens

```
<400> SEQUENCE: 107
catatatttt caaagatcaa                                              20

<210> SEQ ID NO 108
<211> LENGTH: 20
<212> TYPE: DNA
<213> ORGANISM: Homo sapiens

<400> SEQUENCE: 108
atatattttc aaagatcaaa                                              20

<210> SEQ ID NO 109
<211> LENGTH: 20
<212> TYPE: DNA
<213> ORGANISM: Homo sapiens

<400> SEQUENCE: 109
tatattttca aagatcaaat                                              20

<210> SEQ ID NO 110
<211> LENGTH: 20
<212> TYPE: DNA
<213> ORGANISM: Homo sapiens

<400> SEQUENCE: 110
atattttcaa agatcaaatg                                              20

<210> SEQ ID NO 111
<211> LENGTH: 20
<212> TYPE: DNA
<213> ORGANISM: Homo sapiens

<400> SEQUENCE: 111
tattttcaaa gatcaaatgg                                              20

<210> SEQ ID NO 112
<211> LENGTH: 20
<212> TYPE: DNA
<213> ORGANISM: Homo sapiens

<400> SEQUENCE: 112
attttcaaag atcaaatggc                                              20

<210> SEQ ID NO 113
<211> LENGTH: 20
<212> TYPE: DNA
<213> ORGANISM: Homo sapiens

<400> SEQUENCE: 113
ttttcaaaga tcaaatggca                                              20

<210> SEQ ID NO 114
<211> LENGTH: 20
<212> TYPE: DNA
<213> ORGANISM: Homo sapiens

<400> SEQUENCE: 114
tttcaaagat caaatggcat                                              20

<210> SEQ ID NO 115
<211> LENGTH: 20
<212> TYPE: DNA
<213> ORGANISM: Homo sapiens
```

-continued

<400> SEQUENCE: 115
ttcaaagatc aaatggcatt                                        20

<210> SEQ ID NO 116
<211> LENGTH: 20
<212> TYPE: DNA
<213> ORGANISM: Homo sapiens

<400> SEQUENCE: 116
tcaaagatca aatggcattt                                        20

<210> SEQ ID NO 117
<211> LENGTH: 20
<212> TYPE: DNA
<213> ORGANISM: Homo sapiens

<400> SEQUENCE: 117
caaagatcaa atggcattta                                        20

<210> SEQ ID NO 118
<211> LENGTH: 19
<212> TYPE: DNA
<213> ORGANISM: Homo sapiens

<400> SEQUENCE: 118
tattaaaaca tatattttc                                         19

<210> SEQ ID NO 119
<211> LENGTH: 19
<212> TYPE: DNA
<213> ORGANISM: Homo sapiens

<400> SEQUENCE: 119
attaaaacat atattttca                                         19

<210> SEQ ID NO 120
<211> LENGTH: 19
<212> TYPE: DNA
<213> ORGANISM: Homo sapiens

<400> SEQUENCE: 120
ttaaaacata tattttcaa                                         19

<210> SEQ ID NO 121
<211> LENGTH: 19
<212> TYPE: DNA
<213> ORGANISM: Homo sapiens

<400> SEQUENCE: 121
taaaacatat attttcaaa                                         19

<210> SEQ ID NO 122
<211> LENGTH: 19
<212> TYPE: DNA
<213> ORGANISM: Homo sapiens

<400> SEQUENCE: 122
aaaacatata ttttcaaag                                         19

<210> SEQ ID NO 123
<211> LENGTH: 19
<212> TYPE: DNA

```
<213> ORGANISM: Homo sapiens

<400> SEQUENCE: 123
aaacatatat tttcaaaga                                               19

<210> SEQ ID NO 124
<211> LENGTH: 19
<212> TYPE: DNA
<213> ORGANISM: Homo sapiens

<400> SEQUENCE: 124
aacatatatt ttcaaagat                                               19

<210> SEQ ID NO 125
<211> LENGTH: 19
<212> TYPE: DNA
<213> ORGANISM: Homo sapiens

<400> SEQUENCE: 125
acatatattt tcaaagatc                                               19

<210> SEQ ID NO 126
<211> LENGTH: 19
<212> TYPE: DNA
<213> ORGANISM: Homo sapiens

<400> SEQUENCE: 126
catatatttt caaagatca                                               19

<210> SEQ ID NO 127
<211> LENGTH: 19
<212> TYPE: DNA
<213> ORGANISM: Homo sapiens

<400> SEQUENCE: 127
atatattttc aaagatcaa                                               19

<210> SEQ ID NO 128
<211> LENGTH: 19
<212> TYPE: DNA
<213> ORGANISM: Homo sapiens

<400> SEQUENCE: 128
tatattttca aagatcaaa                                               19

<210> SEQ ID NO 129
<211> LENGTH: 19
<212> TYPE: DNA
<213> ORGANISM: Homo sapiens

<400> SEQUENCE: 129
atattttcaa agatcaaat                                               19

<210> SEQ ID NO 130
<211> LENGTH: 19
<212> TYPE: DNA
<213> ORGANISM: Homo sapiens

<400> SEQUENCE: 130
tattttcaaa gatcaaatg                                               19

<210> SEQ ID NO 131
<211> LENGTH: 19
```

```
<212> TYPE: DNA
<213> ORGANISM: Homo sapiens

<400> SEQUENCE: 131
attttcaaag atcaaatgg                                                19

<210> SEQ ID NO 132
<211> LENGTH: 19
<212> TYPE: DNA
<213> ORGANISM: Homo sapiens

<400> SEQUENCE: 132
ttttcaaaga tcaaatggc                                                19

<210> SEQ ID NO 133
<211> LENGTH: 19
<212> TYPE: DNA
<213> ORGANISM: Homo sapiens

<400> SEQUENCE: 133
tttcaaagat caaatggca                                                19

<210> SEQ ID NO 134
<211> LENGTH: 19
<212> TYPE: DNA
<213> ORGANISM: Homo sapiens

<400> SEQUENCE: 134
ttcaaagatc aaatggcat                                                19

<210> SEQ ID NO 135
<211> LENGTH: 19
<212> TYPE: DNA
<213> ORGANISM: Homo sapiens

<400> SEQUENCE: 135
tcaaagatca aatggcatt                                                19

<210> SEQ ID NO 136
<211> LENGTH: 19
<212> TYPE: DNA
<213> ORGANISM: Homo sapiens

<400> SEQUENCE: 136
caaagatcaa atggcattt                                                19

<210> SEQ ID NO 137
<211> LENGTH: 18
<212> TYPE: DNA
<213> ORGANISM: Homo sapiens

<400> SEQUENCE: 137
attaaaacat atattttc                                                 18

<210> SEQ ID NO 138
<211> LENGTH: 18
<212> TYPE: DNA
<213> ORGANISM: Homo sapiens

<400> SEQUENCE: 138
ttaaaacata tattttca                                                 18

<210> SEQ ID NO 139
```

```
<211> LENGTH: 18
<212> TYPE: DNA
<213> ORGANISM: Homo sapiens

<400> SEQUENCE: 139
taaaacatat attttcaa                                                 18

<210> SEQ ID NO 140
<211> LENGTH: 18
<212> TYPE: DNA
<213> ORGANISM: Homo sapiens

<400> SEQUENCE: 140
aaaacatata ttttcaaa                                                 18

<210> SEQ ID NO 141
<211> LENGTH: 18
<212> TYPE: DNA
<213> ORGANISM: Homo sapiens

<400> SEQUENCE: 141
aaacatatat tttcaaag                                                 18

<210> SEQ ID NO 142
<211> LENGTH: 18
<212> TYPE: DNA
<213> ORGANISM: Homo sapiens

<400> SEQUENCE: 142
aacatatatt ttcaaaga                                                 18

<210> SEQ ID NO 143
<211> LENGTH: 18
<212> TYPE: DNA
<213> ORGANISM: Homo sapiens

<400> SEQUENCE: 143
acatatattt tcaaagat                                                 18

<210> SEQ ID NO 144
<211> LENGTH: 18
<212> TYPE: DNA
<213> ORGANISM: Homo sapiens

<400> SEQUENCE: 144
catatatttt caaagatc                                                 18

<210> SEQ ID NO 145
<211> LENGTH: 18
<212> TYPE: DNA
<213> ORGANISM: Homo sapiens

<400> SEQUENCE: 145
atatattttc aaagatca                                                 18

<210> SEQ ID NO 146
<211> LENGTH: 18
<212> TYPE: DNA
<213> ORGANISM: Homo sapiens

<400> SEQUENCE: 146
tatattttca aagatcaa                                                 18
```

```
<210> SEQ ID NO 147
<211> LENGTH: 18
<212> TYPE: DNA
<213> ORGANISM: Homo sapiens

<400> SEQUENCE: 147
atattttcaa agatcaaa                                                 18

<210> SEQ ID NO 148
<211> LENGTH: 18
<212> TYPE: DNA
<213> ORGANISM: Homo sapiens

<400> SEQUENCE: 148
tattttcaaa gatcaaat                                                 18

<210> SEQ ID NO 149
<211> LENGTH: 18
<212> TYPE: DNA
<213> ORGANISM: Homo sapiens

<400> SEQUENCE: 149
attttcaaag atcaaatg                                                 18

<210> SEQ ID NO 150
<211> LENGTH: 18
<212> TYPE: DNA
<213> ORGANISM: Homo sapiens

<400> SEQUENCE: 150
ttttcaaaga tcaaatgg                                                 18

<210> SEQ ID NO 151
<211> LENGTH: 18
<212> TYPE: DNA
<213> ORGANISM: Homo sapiens

<400> SEQUENCE: 151
tttcaaagat caaatggc                                                 18

<210> SEQ ID NO 152
<211> LENGTH: 18
<212> TYPE: DNA
<213> ORGANISM: Homo sapiens

<400> SEQUENCE: 152
ttcaaagatc aaatggca                                                 18

<210> SEQ ID NO 153
<211> LENGTH: 18
<212> TYPE: DNA
<213> ORGANISM: Homo sapiens

<400> SEQUENCE: 153
tcaaagatca aatggcat                                                 18

<210> SEQ ID NO 154
<211> LENGTH: 18
<212> TYPE: DNA
<213> ORGANISM: Homo sapiens

<400> SEQUENCE: 154
caaagatcaa atggcatt                                                 18
```

<210> SEQ ID NO 155
<211> LENGTH: 17
<212> TYPE: DNA
<213> ORGANISM: Homo sapiens

<400> SEQUENCE: 155
ttaaaacata tattttc                                                  17

<210> SEQ ID NO 156
<211> LENGTH: 17
<212> TYPE: DNA
<213> ORGANISM: Homo sapiens

<400> SEQUENCE: 156
taaaacatat attttca                                                  17

<210> SEQ ID NO 157
<211> LENGTH: 17
<212> TYPE: DNA
<213> ORGANISM: Homo sapiens

<400> SEQUENCE: 157
aaaacatata ttttcaa                                                  17

<210> SEQ ID NO 158
<211> LENGTH: 17
<212> TYPE: DNA
<213> ORGANISM: Homo sapiens

<400> SEQUENCE: 158
aaacatatat tttcaaa                                                  17

<210> SEQ ID NO 159
<211> LENGTH: 17
<212> TYPE: DNA
<213> ORGANISM: Homo sapiens

<400> SEQUENCE: 159
aacatatatt ttcaaag                                                  17

<210> SEQ ID NO 160
<211> LENGTH: 17
<212> TYPE: DNA
<213> ORGANISM: Homo sapiens

<400> SEQUENCE: 160
acatatattt tcaaaga                                                  17

<210> SEQ ID NO 161
<211> LENGTH: 17
<212> TYPE: DNA
<213> ORGANISM: Homo sapiens

<400> SEQUENCE: 161
catatatttt caaagat                                                  17

<210> SEQ ID NO 162
<211> LENGTH: 17
<212> TYPE: DNA
<213> ORGANISM: Homo sapiens

<400> SEQUENCE: 162
atatattttc aaagatc                                                  17

<210> SEQ ID NO 163
<211> LENGTH: 17
<212> TYPE: DNA
<213> ORGANISM: Homo sapiens

<400> SEQUENCE: 163
tatattttca aagatca                                                 17

<210> SEQ ID NO 164
<211> LENGTH: 17
<212> TYPE: DNA
<213> ORGANISM: Homo sapiens

<400> SEQUENCE: 164
atattttcaa agatcaa                                                 17

<210> SEQ ID NO 165
<211> LENGTH: 17
<212> TYPE: DNA
<213> ORGANISM: Homo sapiens

<400> SEQUENCE: 165
tattttcaaa gatcaaa                                                 17

<210> SEQ ID NO 166
<211> LENGTH: 17
<212> TYPE: DNA
<213> ORGANISM: Homo sapiens

<400> SEQUENCE: 166
attttcaaag atcaaat                                                 17

<210> SEQ ID NO 167
<211> LENGTH: 17
<212> TYPE: DNA
<213> ORGANISM: Homo sapiens

<400> SEQUENCE: 167
ttttcaaaga tcaaatg                                                 17

<210> SEQ ID NO 168
<211> LENGTH: 17
<212> TYPE: DNA
<213> ORGANISM: Homo sapiens

<400> SEQUENCE: 168
tttcaaagat caaatgg                                                 17

<210> SEQ ID NO 169
<211> LENGTH: 17
<212> TYPE: DNA
<213> ORGANISM: Homo sapiens

<400> SEQUENCE: 169
ttcaaagatc aaatggc                                                 17

<210> SEQ ID NO 170
<211> LENGTH: 17
<212> TYPE: DNA
<213> ORGANISM: Homo sapiens

<400> SEQUENCE: 170
tcaaagatca aatggca                                    17

<210> SEQ ID NO 171
<211> LENGTH: 17
<212> TYPE: DNA
<213> ORGANISM: Homo sapiens

<400> SEQUENCE: 171
caaagatcaa atggcat                                    17

<210> SEQ ID NO 172
<211> LENGTH: 16
<212> TYPE: DNA
<213> ORGANISM: Homo sapiens

<400> SEQUENCE: 172
taaaacatat attttc                                     16

<210> SEQ ID NO 173
<211> LENGTH: 16
<212> TYPE: DNA
<213> ORGANISM: Homo sapiens

<400> SEQUENCE: 173
aaaacatata ttttca                                     16

<210> SEQ ID NO 174
<211> LENGTH: 16
<212> TYPE: DNA
<213> ORGANISM: Homo sapiens

<400> SEQUENCE: 174
aaacatatat tttcaa                                     16

<210> SEQ ID NO 175
<211> LENGTH: 16
<212> TYPE: DNA
<213> ORGANISM: Homo sapiens

<400> SEQUENCE: 175
aacatatatt ttcaaa                                     16

<210> SEQ ID NO 176
<211> LENGTH: 16
<212> TYPE: DNA
<213> ORGANISM: Homo sapiens

<400> SEQUENCE: 176
acatatattt tcaaag                                     16

<210> SEQ ID NO 177
<211> LENGTH: 16
<212> TYPE: DNA
<213> ORGANISM: Homo sapiens

<400> SEQUENCE: 177
catatatttt caaaga                                     16

<210> SEQ ID NO 178
<211> LENGTH: 16
<212> TYPE: DNA
<213> ORGANISM: Homo sapiens

<400> SEQUENCE: 178

```
atatattttc aaagat                                              16

<210> SEQ ID NO 179
<211> LENGTH: 16
<212> TYPE: DNA
<213> ORGANISM: Homo sapiens

<400> SEQUENCE: 179
tatattttca aagatc                                              16

<210> SEQ ID NO 180
<211> LENGTH: 16
<212> TYPE: DNA
<213> ORGANISM: Homo sapiens

<400> SEQUENCE: 180
atattttcaa agatca                                              16

<210> SEQ ID NO 181
<211> LENGTH: 16
<212> TYPE: DNA
<213> ORGANISM: Homo sapiens

<400> SEQUENCE: 181
tattttcaaa gatcaa                                              16

<210> SEQ ID NO 182
<211> LENGTH: 16
<212> TYPE: DNA
<213> ORGANISM: Homo sapiens

<400> SEQUENCE: 182
attttcaaag atcaaa                                              16

<210> SEQ ID NO 183
<211> LENGTH: 16
<212> TYPE: DNA
<213> ORGANISM: Homo sapiens

<400> SEQUENCE: 183
ttttcaaaga tcaaat                                              16

<210> SEQ ID NO 184
<211> LENGTH: 16
<212> TYPE: DNA
<213> ORGANISM: Homo sapiens

<400> SEQUENCE: 184
tttcaaagat caaatg                                              16

<210> SEQ ID NO 185
<211> LENGTH: 16
<212> TYPE: DNA
<213> ORGANISM: Homo sapiens

<400> SEQUENCE: 185
ttcaaagatc aaatgg                                              16

<210> SEQ ID NO 186
<211> LENGTH: 16
<212> TYPE: DNA
<213> ORGANISM: Homo sapiens
```

```
<400> SEQUENCE: 186
tcaaagatca aatggc                                                   16

<210> SEQ ID NO 187
<211> LENGTH: 16
<212> TYPE: DNA
<213> ORGANISM: Homo sapiens

<400> SEQUENCE: 187
caaagatcaa atggca                                                   16

<210> SEQ ID NO 188
<211> LENGTH: 15
<212> TYPE: DNA
<213> ORGANISM: Homo sapiens

<400> SEQUENCE: 188
aaaacatata ttttc                                                    15

<210> SEQ ID NO 189
<211> LENGTH: 15
<212> TYPE: DNA
<213> ORGANISM: Homo sapiens

<400> SEQUENCE: 189
aaacatatat tttca                                                    15

<210> SEQ ID NO 190
<211> LENGTH: 15
<212> TYPE: DNA
<213> ORGANISM: Homo sapiens

<400> SEQUENCE: 190
aacatatatt ttcaa                                                    15

<210> SEQ ID NO 191
<211> LENGTH: 15
<212> TYPE: DNA
<213> ORGANISM: Homo sapiens

<400> SEQUENCE: 191
acatatattt tcaaa                                                    15

<210> SEQ ID NO 192
<211> LENGTH: 15
<212> TYPE: DNA
<213> ORGANISM: Homo sapiens

<400> SEQUENCE: 192
catatatttt caaag                                                    15

<210> SEQ ID NO 193
<211> LENGTH: 15
<212> TYPE: DNA
<213> ORGANISM: Homo sapiens

<400> SEQUENCE: 193
atatattttc aaaga                                                    15

<210> SEQ ID NO 194
<211> LENGTH: 15
<212> TYPE: DNA
<213> ORGANISM: Homo sapiens
```

```
<400> SEQUENCE: 194
tatattttca aagat                                                15

<210> SEQ ID NO 195
<211> LENGTH: 15
<212> TYPE: DNA
<213> ORGANISM: Homo sapiens

<400> SEQUENCE: 195
atattttcaa agatc                                                15

<210> SEQ ID NO 196
<211> LENGTH: 15
<212> TYPE: DNA
<213> ORGANISM: Homo sapiens

<400> SEQUENCE: 196
tattttcaaa gatca                                                15

<210> SEQ ID NO 197
<211> LENGTH: 15
<212> TYPE: DNA
<213> ORGANISM: Homo sapiens

<400> SEQUENCE: 197
attttcaaag atcaa                                                15

<210> SEQ ID NO 198
<211> LENGTH: 15
<212> TYPE: DNA
<213> ORGANISM: Homo sapiens

<400> SEQUENCE: 198
ttttcaaaga tcaaa                                                15

<210> SEQ ID NO 199
<211> LENGTH: 15
<212> TYPE: DNA
<213> ORGANISM: Homo sapiens

<400> SEQUENCE: 199
tttcaaagat caaat                                                15

<210> SEQ ID NO 200
<211> LENGTH: 15
<212> TYPE: DNA
<213> ORGANISM: Homo sapiens

<400> SEQUENCE: 200
ttcaaagatc aaatg                                                15

<210> SEQ ID NO 201
<211> LENGTH: 15
<212> TYPE: DNA
<213> ORGANISM: Homo sapiens

<400> SEQUENCE: 201
tcaaagatca aatgg                                                15

<210> SEQ ID NO 202
<211> LENGTH: 15
<212> TYPE: DNA
```

<213> ORGANISM: Homo sapiens

<400> SEQUENCE: 202
caaagatcaa atggc                                                    15

<210> SEQ ID NO 203
<211> LENGTH: 20
<212> TYPE: DNA
<213> ORGANISM: Homo sapiens

<400> SEQUENCE: 203
tctgcgcttg taagacatca                                               20

<210> SEQ ID NO 204
<211> LENGTH: 20
<212> TYPE: DNA
<213> ORGANISM: Homo sapiens

<400> SEQUENCE: 204
ctgcgcttgt aagacatcac                                               20

<210> SEQ ID NO 205
<211> LENGTH: 20
<212> TYPE: DNA
<213> ORGANISM: Homo sapiens

<400> SEQUENCE: 205
tgcgcttgta agacatcact                                               20

<210> SEQ ID NO 206
<211> LENGTH: 20
<212> TYPE: DNA
<213> ORGANISM: Homo sapiens

<400> SEQUENCE: 206
gcgcttgtaa gacatcactg                                               20

<210> SEQ ID NO 207
<211> LENGTH: 20
<212> TYPE: DNA
<213> ORGANISM: Homo sapiens

<400> SEQUENCE: 207
cgcttgtaag acatcactgt                                               20

<210> SEQ ID NO 208
<211> LENGTH: 20
<212> TYPE: DNA
<213> ORGANISM: Homo sapiens

<400> SEQUENCE: 208
gcttgtaaga catcactgtg                                               20

<210> SEQ ID NO 209
<211> LENGTH: 20
<212> TYPE: DNA
<213> ORGANISM: Homo sapiens

<400> SEQUENCE: 209
cttgtaagac atcactgtga                                               20

<210> SEQ ID NO 210
<211> LENGTH: 20

```
<212> TYPE: DNA
<213> ORGANISM: Homo sapiens

<400> SEQUENCE: 210
ttgtaagaca tcactgtgaa                                                 20

<210> SEQ ID NO 211
<211> LENGTH: 20
<212> TYPE: DNA
<213> ORGANISM: Homo sapiens

<400> SEQUENCE: 211
tgtaagacat cactgtgaag                                                 20

<210> SEQ ID NO 212
<211> LENGTH: 20
<212> TYPE: DNA
<213> ORGANISM: Homo sapiens

<400> SEQUENCE: 212
gtaagacatc actgtgaaga                                                 20

<210> SEQ ID NO 213
<211> LENGTH: 20
<212> TYPE: DNA
<213> ORGANISM: Homo sapiens

<400> SEQUENCE: 213
taagacatca ctgtgaagag                                                 20

<210> SEQ ID NO 214
<211> LENGTH: 20
<212> TYPE: DNA
<213> ORGANISM: Homo sapiens

<400> SEQUENCE: 214
aagacatcac tgtgaagagc                                                 20

<210> SEQ ID NO 215
<211> LENGTH: 20
<212> TYPE: DNA
<213> ORGANISM: Homo sapiens

<400> SEQUENCE: 215
agacatcact gtgaagagct                                                 20

<210> SEQ ID NO 216
<211> LENGTH: 20
<212> TYPE: DNA
<213> ORGANISM: Homo sapiens

<400> SEQUENCE: 216
gacatcactg tgaagagctt                                                 20

<210> SEQ ID NO 217
<211> LENGTH: 20
<212> TYPE: DNA
<213> ORGANISM: Homo sapiens

<400> SEQUENCE: 217
acatcactgt gaagagcttg                                                 20

<210> SEQ ID NO 218
```

```
<211> LENGTH: 20
<212> TYPE: DNA
<213> ORGANISM: Homo sapiens

<400> SEQUENCE: 218
catcactgtg aagagcttga                                              20

<210> SEQ ID NO 219
<211> LENGTH: 20
<212> TYPE: DNA
<213> ORGANISM: Homo sapiens

<400> SEQUENCE: 219
atcactgtga agagcttgac                                              20

<210> SEQ ID NO 220
<211> LENGTH: 20
<212> TYPE: DNA
<213> ORGANISM: Homo sapiens

<400> SEQUENCE: 220
tcactgtgaa gagcttgact                                              20

<210> SEQ ID NO 221
<211> LENGTH: 20
<212> TYPE: DNA
<213> ORGANISM: Homo sapiens

<400> SEQUENCE: 221
cactgtgaag agcttgactt                                              20

<210> SEQ ID NO 222
<211> LENGTH: 20
<212> TYPE: DNA
<213> ORGANISM: Homo sapiens

<400> SEQUENCE: 222
actgtgaaga gcttgacttg                                              20

<210> SEQ ID NO 223
<211> LENGTH: 19
<212> TYPE: DNA
<213> ORGANISM: Homo sapiens

<400> SEQUENCE: 223
ctgcgcttgt aagacatca                                               19

<210> SEQ ID NO 224
<211> LENGTH: 19
<212> TYPE: DNA
<213> ORGANISM: Homo sapiens

<400> SEQUENCE: 224
tgcgcttgta agacatcac                                               19

<210> SEQ ID NO 225
<211> LENGTH: 19
<212> TYPE: DNA
<213> ORGANISM: Homo sapiens

<400> SEQUENCE: 225
gcgcttgtaa gacatcact                                               19
```

```
<210> SEQ ID NO 226
<211> LENGTH: 19
<212> TYPE: DNA
<213> ORGANISM: Homo sapiens

<400> SEQUENCE: 226
cgcttgtaag acatcactg                                                  19

<210> SEQ ID NO 227
<211> LENGTH: 19
<212> TYPE: DNA
<213> ORGANISM: Homo sapiens

<400> SEQUENCE: 227
gcttgtaaga catcactgt                                                  19

<210> SEQ ID NO 228
<211> LENGTH: 19
<212> TYPE: DNA
<213> ORGANISM: Homo sapiens

<400> SEQUENCE: 228
cttgtaagac atcactgtg                                                  19

<210> SEQ ID NO 229
<211> LENGTH: 19
<212> TYPE: DNA
<213> ORGANISM: Homo sapiens

<400> SEQUENCE: 229
ttgtaagaca tcactgtga                                                  19

<210> SEQ ID NO 230
<211> LENGTH: 19
<212> TYPE: DNA
<213> ORGANISM: Homo sapiens

<400> SEQUENCE: 230
tgtaagacat cactgtgaa                                                  19

<210> SEQ ID NO 231
<211> LENGTH: 19
<212> TYPE: DNA
<213> ORGANISM: Homo sapiens

<400> SEQUENCE: 231
gtaagacatc actgtgaag                                                  19

<210> SEQ ID NO 232
<211> LENGTH: 19
<212> TYPE: DNA
<213> ORGANISM: Homo sapiens

<400> SEQUENCE: 232
taagacatca ctgtgaaga                                                  19

<210> SEQ ID NO 233
<211> LENGTH: 19
<212> TYPE: DNA
<213> ORGANISM: Homo sapiens

<400> SEQUENCE: 233
aagacatcac tgtgaagag                                                  19
```

<210> SEQ ID NO 234
<211> LENGTH: 19
<212> TYPE: DNA
<213> ORGANISM: Homo sapiens

<400> SEQUENCE: 234
agacatcact gtgaagagc                                               19

<210> SEQ ID NO 235
<211> LENGTH: 19
<212> TYPE: DNA
<213> ORGANISM: Homo sapiens

<400> SEQUENCE: 235
gacatcactg tgaagagct                                               19

<210> SEQ ID NO 236
<211> LENGTH: 19
<212> TYPE: DNA
<213> ORGANISM: Homo sapiens

<400> SEQUENCE: 236
acatcactgt gaagagctt                                               19

<210> SEQ ID NO 237
<211> LENGTH: 19
<212> TYPE: DNA
<213> ORGANISM: Homo sapiens

<400> SEQUENCE: 237
catcactgtg aagagcttg                                               19

<210> SEQ ID NO 238
<211> LENGTH: 19
<212> TYPE: DNA
<213> ORGANISM: Homo sapiens

<400> SEQUENCE: 238
atcactgtga agagcttga                                               19

<210> SEQ ID NO 239
<211> LENGTH: 19
<212> TYPE: DNA
<213> ORGANISM: Homo sapiens

<400> SEQUENCE: 239
tcactgtgaa gagcttgac                                               19

<210> SEQ ID NO 240
<211> LENGTH: 19
<212> TYPE: DNA
<213> ORGANISM: Homo sapiens

<400> SEQUENCE: 240
cactgtgaag agcttgact                                               19

<210> SEQ ID NO 241
<211> LENGTH: 19
<212> TYPE: DNA
<213> ORGANISM: Homo sapiens

<400> SEQUENCE: 241
actgtgaaga gcttgactt                                               19

<210> SEQ ID NO 242
<211> LENGTH: 18
<212> TYPE: DNA
<213> ORGANISM: Homo sapiens

<400> SEQUENCE: 242
tgcgcttgta agacatca                                                 18

<210> SEQ ID NO 243
<211> LENGTH: 18
<212> TYPE: DNA
<213> ORGANISM: Homo sapiens

<400> SEQUENCE: 243
gcgcttgtaa gacatcac                                                 18

<210> SEQ ID NO 244
<211> LENGTH: 18
<212> TYPE: DNA
<213> ORGANISM: Homo sapiens

<400> SEQUENCE: 244
cgcttgtaag acatcact                                                 18

<210> SEQ ID NO 245
<211> LENGTH: 18
<212> TYPE: DNA
<213> ORGANISM: Homo sapiens

<400> SEQUENCE: 245
gcttgtaaga catcactg                                                 18

<210> SEQ ID NO 246
<211> LENGTH: 18
<212> TYPE: DNA
<213> ORGANISM: Homo sapiens

<400> SEQUENCE: 246
cttgtaagac atcactgt                                                 18

<210> SEQ ID NO 247
<211> LENGTH: 18
<212> TYPE: DNA
<213> ORGANISM: Homo sapiens

<400> SEQUENCE: 247
ttgtaagaca tcactgtg                                                 18

<210> SEQ ID NO 248
<211> LENGTH: 18
<212> TYPE: DNA
<213> ORGANISM: Homo sapiens

<400> SEQUENCE: 248
tgtaagacat cactgtga                                                 18

<210> SEQ ID NO 249
<211> LENGTH: 18
<212> TYPE: DNA
<213> ORGANISM: Homo sapiens

<400> SEQUENCE: 249
gtaagacatc actgtgaa                                                    18

<210> SEQ ID NO 250
<211> LENGTH: 18
<212> TYPE: DNA
<213> ORGANISM: Homo sapiens

<400> SEQUENCE: 250
taagacatca ctgtgaag                                                    18

<210> SEQ ID NO 251
<211> LENGTH: 18
<212> TYPE: DNA
<213> ORGANISM: Homo sapiens

<400> SEQUENCE: 251
aagacatcac tgtgaaga                                                    18

<210> SEQ ID NO 252
<211> LENGTH: 18
<212> TYPE: DNA
<213> ORGANISM: Homo sapiens

<400> SEQUENCE: 252
agacatcact gtgaagag                                                    18

<210> SEQ ID NO 253
<211> LENGTH: 18
<212> TYPE: DNA
<213> ORGANISM: Homo sapiens

<400> SEQUENCE: 253
gacatcactg tgaagagc                                                    18

<210> SEQ ID NO 254
<211> LENGTH: 18
<212> TYPE: DNA
<213> ORGANISM: Homo sapiens

<400> SEQUENCE: 254
acatcactgt gaagagct                                                    18

<210> SEQ ID NO 255
<211> LENGTH: 18
<212> TYPE: DNA
<213> ORGANISM: Homo sapiens

<400> SEQUENCE: 255
catcactgtg aagagctt                                                    18

<210> SEQ ID NO 256
<211> LENGTH: 18
<212> TYPE: DNA
<213> ORGANISM: Homo sapiens

<400> SEQUENCE: 256
atcactgtga agagcttg                                                    18

<210> SEQ ID NO 257
<211> LENGTH: 18
<212> TYPE: DNA
<213> ORGANISM: Homo sapiens

<400> SEQUENCE: 257

```
tcactgtgaa gagcttga                                                18

<210> SEQ ID NO 258
<211> LENGTH: 18
<212> TYPE: DNA
<213> ORGANISM: Homo sapiens

<400> SEQUENCE: 258
cactgtgaag agcttgac                                                18

<210> SEQ ID NO 259
<211> LENGTH: 18
<212> TYPE: DNA
<213> ORGANISM: Homo sapiens

<400> SEQUENCE: 259
actgtgaaga gcttgact                                                18

<210> SEQ ID NO 260
<211> LENGTH: 17
<212> TYPE: DNA
<213> ORGANISM: Homo sapiens

<400> SEQUENCE: 260
gcgcttgtaa gacatca                                                 17

<210> SEQ ID NO 261
<211> LENGTH: 17
<212> TYPE: DNA
<213> ORGANISM: Homo sapiens

<400> SEQUENCE: 261
cgcttgtaag acatcac                                                 17

<210> SEQ ID NO 262
<211> LENGTH: 17
<212> TYPE: DNA
<213> ORGANISM: Homo sapiens

<400> SEQUENCE: 262
gcttgtaaga catcact                                                 17

<210> SEQ ID NO 263
<211> LENGTH: 17
<212> TYPE: DNA
<213> ORGANISM: Homo sapiens

<400> SEQUENCE: 263
cttgtaagac atcactg                                                 17

<210> SEQ ID NO 264
<211> LENGTH: 17
<212> TYPE: DNA
<213> ORGANISM: Homo sapiens

<400> SEQUENCE: 264
ttgtaagaca tcactgt                                                 17

<210> SEQ ID NO 265
<211> LENGTH: 17
<212> TYPE: DNA
<213> ORGANISM: Homo sapiens
```

```
<400> SEQUENCE: 265
tgtaagacat cactgtg                                                    17

<210> SEQ ID NO 266
<211> LENGTH: 17
<212> TYPE: DNA
<213> ORGANISM: Homo sapiens

<400> SEQUENCE: 266
gtaagacatc actgtga                                                    17

<210> SEQ ID NO 267
<211> LENGTH: 17
<212> TYPE: DNA
<213> ORGANISM: Homo sapiens

<400> SEQUENCE: 267
taagacatca ctgtgaa                                                    17

<210> SEQ ID NO 268
<211> LENGTH: 17
<212> TYPE: DNA
<213> ORGANISM: Homo sapiens

<400> SEQUENCE: 268
aagacatcac tgtgaag                                                    17

<210> SEQ ID NO 269
<211> LENGTH: 17
<212> TYPE: DNA
<213> ORGANISM: Homo sapiens

<400> SEQUENCE: 269
agacatcact gtgaaga                                                    17

<210> SEQ ID NO 270
<211> LENGTH: 17
<212> TYPE: DNA
<213> ORGANISM: Homo sapiens

<400> SEQUENCE: 270
gacatcactg tgaagag                                                    17

<210> SEQ ID NO 271
<211> LENGTH: 17
<212> TYPE: DNA
<213> ORGANISM: Homo sapiens

<400> SEQUENCE: 271
acatcactgt gaagagc                                                    17

<210> SEQ ID NO 272
<211> LENGTH: 17
<212> TYPE: DNA
<213> ORGANISM: Homo sapiens

<400> SEQUENCE: 272
catcactgtg aagagct                                                    17

<210> SEQ ID NO 273
<211> LENGTH: 17
<212> TYPE: DNA
<213> ORGANISM: Homo sapiens
```

```
<400> SEQUENCE: 273
atcactgtga agagctt                                                       17

<210> SEQ ID NO 274
<211> LENGTH: 17
<212> TYPE: DNA
<213> ORGANISM: Homo sapiens

<400> SEQUENCE: 274
tcactgtgaa gagcttg                                                       17

<210> SEQ ID NO 275
<211> LENGTH: 17
<212> TYPE: DNA
<213> ORGANISM: Homo sapiens

<400> SEQUENCE: 275
cactgtgaag agcttga                                                       17

<210> SEQ ID NO 276
<211> LENGTH: 17
<212> TYPE: DNA
<213> ORGANISM: Homo sapiens

<400> SEQUENCE: 276
actgtgaaga gcttgac                                                       17

<210> SEQ ID NO 277
<211> LENGTH: 16
<212> TYPE: DNA
<213> ORGANISM: Homo sapiens

<400> SEQUENCE: 277
cgcttgtaag acatca                                                        16

<210> SEQ ID NO 278
<211> LENGTH: 16
<212> TYPE: DNA
<213> ORGANISM: Homo sapiens

<400> SEQUENCE: 278
gcttgtaaga catcac                                                        16

<210> SEQ ID NO 279
<211> LENGTH: 16
<212> TYPE: DNA
<213> ORGANISM: Homo sapiens

<400> SEQUENCE: 279
cttgtaagac atcact                                                        16

<210> SEQ ID NO 280
<211> LENGTH: 16
<212> TYPE: DNA
<213> ORGANISM: Homo sapiens

<400> SEQUENCE: 280
ttgtaagaca tcactg                                                        16

<210> SEQ ID NO 281
<211> LENGTH: 16
<212> TYPE: DNA
```

<213> ORGANISM: Homo sapiens

<400> SEQUENCE: 281
tgtaagacat cactgt                                                        16

<210> SEQ ID NO 282
<211> LENGTH: 16
<212> TYPE: DNA
<213> ORGANISM: Homo sapiens

<400> SEQUENCE: 282
gtaagacatc actgtg                                                        16

<210> SEQ ID NO 283
<211> LENGTH: 16
<212> TYPE: DNA
<213> ORGANISM: Homo sapiens

<400> SEQUENCE: 283
taagacatca ctgtga                                                        16

<210> SEQ ID NO 284
<211> LENGTH: 16
<212> TYPE: DNA
<213> ORGANISM: Homo sapiens

<400> SEQUENCE: 284
aagacatcac tgtgaa                                                        16

<210> SEQ ID NO 285
<211> LENGTH: 16
<212> TYPE: DNA
<213> ORGANISM: Homo sapiens

<400> SEQUENCE: 285
agacatcact gtgaag                                                        16

<210> SEQ ID NO 286
<211> LENGTH: 16
<212> TYPE: DNA
<213> ORGANISM: Homo sapiens

<400> SEQUENCE: 286
gacatcactg tgaaga                                                        16

<210> SEQ ID NO 287
<211> LENGTH: 16
<212> TYPE: DNA
<213> ORGANISM: Homo sapiens

<400> SEQUENCE: 287
acatcactgt gaagag                                                        16

<210> SEQ ID NO 288
<211> LENGTH: 16
<212> TYPE: DNA
<213> ORGANISM: Homo sapiens

<400> SEQUENCE: 288
catcactgtg aagagc                                                        16

<210> SEQ ID NO 289
<211> LENGTH: 16

<212> TYPE: DNA
<213> ORGANISM: Homo sapiens

<400> SEQUENCE: 289
atcactgtga agagct                                                  16

<210> SEQ ID NO 290
<211> LENGTH: 16
<212> TYPE: DNA
<213> ORGANISM: Homo sapiens

<400> SEQUENCE: 290
tcactgtgaa gagctt                                                  16

<210> SEQ ID NO 291
<211> LENGTH: 16
<212> TYPE: DNA
<213> ORGANISM: Homo sapiens

<400> SEQUENCE: 291
cactgtgaag agcttg                                                  16

<210> SEQ ID NO 292
<211> LENGTH: 16
<212> TYPE: DNA
<213> ORGANISM: Homo sapiens

<400> SEQUENCE: 292
actgtgaaga gcttga                                                  16

<210> SEQ ID NO 293
<211> LENGTH: 15
<212> TYPE: DNA
<213> ORGANISM: Homo sapiens

<400> SEQUENCE: 293
gcttgtaaga catca                                                   15

<210> SEQ ID NO 294
<211> LENGTH: 15
<212> TYPE: DNA
<213> ORGANISM: Homo sapiens

<400> SEQUENCE: 294
cttgtaagac atcac                                                   15

<210> SEQ ID NO 295
<211> LENGTH: 15
<212> TYPE: DNA
<213> ORGANISM: Homo sapiens

<400> SEQUENCE: 295
ttgtaagaca tcact                                                   15

<210> SEQ ID NO 296
<211> LENGTH: 15
<212> TYPE: DNA
<213> ORGANISM: Homo sapiens

<400> SEQUENCE: 296
tgtaagacat cactg                                                   15

<210> SEQ ID NO 297

```
<211> LENGTH: 15
<212> TYPE: DNA
<213> ORGANISM: Homo sapiens

<400> SEQUENCE: 297
gtaagacatc actgt                                                          15

<210> SEQ ID NO 298
<211> LENGTH: 15
<212> TYPE: DNA
<213> ORGANISM: Homo sapiens

<400> SEQUENCE: 298
taagacatca ctgtg                                                          15

<210> SEQ ID NO 299
<211> LENGTH: 15
<212> TYPE: DNA
<213> ORGANISM: Homo sapiens

<400> SEQUENCE: 299
aagacatcac tgtga                                                          15

<210> SEQ ID NO 300
<211> LENGTH: 15
<212> TYPE: DNA
<213> ORGANISM: Homo sapiens

<400> SEQUENCE: 300
agacatcact gtgaa                                                          15

<210> SEQ ID NO 301
<211> LENGTH: 15
<212> TYPE: DNA
<213> ORGANISM: Homo sapiens

<400> SEQUENCE: 301
gacatcactg tgaag                                                          15

<210> SEQ ID NO 302
<211> LENGTH: 15
<212> TYPE: DNA
<213> ORGANISM: Homo sapiens

<400> SEQUENCE: 302
acatcactgt gaaga                                                          15

<210> SEQ ID NO 303
<211> LENGTH: 15
<212> TYPE: DNA
<213> ORGANISM: Homo sapiens

<400> SEQUENCE: 303
catcactgtg aagag                                                          15

<210> SEQ ID NO 304
<211> LENGTH: 15
<212> TYPE: DNA
<213> ORGANISM: Homo sapiens

<400> SEQUENCE: 304
atcactgtga agagc                                                          15
```

```
<210> SEQ ID NO 305
<211> LENGTH: 15
<212> TYPE: DNA
<213> ORGANISM: Homo sapiens

<400> SEQUENCE: 305
tcactgtgaa gagct                                                    15

<210> SEQ ID NO 306
<211> LENGTH: 15
<212> TYPE: DNA
<213> ORGANISM: Homo sapiens

<400> SEQUENCE: 306
cactgtgaag agctt                                                    15

<210> SEQ ID NO 307
<211> LENGTH: 15
<212> TYPE: DNA
<213> ORGANISM: Homo sapiens

<400> SEQUENCE: 307
actgtgaaga gcttg                                                    15

<210> SEQ ID NO 308
<211> LENGTH: 20
<212> TYPE: DNA
<213> ORGANISM: Homo sapiens

<400> SEQUENCE: 308
gtggtcccgg gtcctcccca                                               20

<210> SEQ ID NO 309
<211> LENGTH: 20
<212> TYPE: DNA
<213> ORGANISM: Homo sapiens

<400> SEQUENCE: 309
tggtcccggg tcctccccac                                               20

<210> SEQ ID NO 310
<211> LENGTH: 20
<212> TYPE: DNA
<213> ORGANISM: Homo sapiens

<400> SEQUENCE: 310
ggtcccgggt cctccccaca                                               20

<210> SEQ ID NO 311
<211> LENGTH: 20
<212> TYPE: DNA
<213> ORGANISM: Homo sapiens

<400> SEQUENCE: 311
gtcccgggtc ctccccacag                                               20

<210> SEQ ID NO 312
<211> LENGTH: 20
<212> TYPE: DNA
<213> ORGANISM: Homo sapiens

<400> SEQUENCE: 312
tcccgggtcc tccccacaga                                               20
```

<210> SEQ ID NO 313
<211> LENGTH: 20
<212> TYPE: DNA
<213> ORGANISM: Homo sapiens

<400> SEQUENCE: 313
cccgggtcct ccccacagag                                          20

<210> SEQ ID NO 314
<211> LENGTH: 20
<212> TYPE: DNA
<213> ORGANISM: Homo sapiens

<400> SEQUENCE: 314
ccgggtcctc cccacagagg                                          20

<210> SEQ ID NO 315
<211> LENGTH: 20
<212> TYPE: DNA
<213> ORGANISM: Homo sapiens

<400> SEQUENCE: 315
cgggtcctcc ccacagaggg                                          20

<210> SEQ ID NO 316
<211> LENGTH: 20
<212> TYPE: DNA
<213> ORGANISM: Homo sapiens

<400> SEQUENCE: 316
gggtcctccc cacagaggga                                          20

<210> SEQ ID NO 317
<211> LENGTH: 20
<212> TYPE: DNA
<213> ORGANISM: Homo sapiens

<400> SEQUENCE: 317
ggtcctcccc acagagggag                                          20

<210> SEQ ID NO 318
<211> LENGTH: 20
<212> TYPE: DNA
<213> ORGANISM: Homo sapiens

<400> SEQUENCE: 318
gtcctcccca cagagggagg                                          20

<210> SEQ ID NO 319
<211> LENGTH: 20
<212> TYPE: DNA
<213> ORGANISM: Homo sapiens

<400> SEQUENCE: 319
tcctccccac agagggagga                                          20

<210> SEQ ID NO 320
<211> LENGTH: 20
<212> TYPE: DNA
<213> ORGANISM: Homo sapiens

<400> SEQUENCE: 320
cctccccaca gagggaggaa                                          20

```
<210> SEQ ID NO 321
<211> LENGTH: 20
<212> TYPE: DNA
<213> ORGANISM: Homo sapiens

<400> SEQUENCE: 321
ctccccacag agggaggaag                                              20

<210> SEQ ID NO 322
<211> LENGTH: 20
<212> TYPE: DNA
<213> ORGANISM: Homo sapiens

<400> SEQUENCE: 322
tccccacaga gggaggaagc                                              20

<210> SEQ ID NO 323
<211> LENGTH: 20
<212> TYPE: DNA
<213> ORGANISM: Homo sapiens

<400> SEQUENCE: 323
ccccacagag ggaggaagcg                                              20

<210> SEQ ID NO 324
<211> LENGTH: 20
<212> TYPE: DNA
<213> ORGANISM: Homo sapiens

<400> SEQUENCE: 324
cccacagagg gaggaagcgg                                              20

<210> SEQ ID NO 325
<211> LENGTH: 20
<212> TYPE: DNA
<213> ORGANISM: Homo sapiens

<400> SEQUENCE: 325
ccacagaggg aggaagcggg                                              20

<210> SEQ ID NO 326
<211> LENGTH: 20
<212> TYPE: DNA
<213> ORGANISM: Homo sapiens

<400> SEQUENCE: 326
cacagaggga ggaagcgggg                                              20

<210> SEQ ID NO 327
<211> LENGTH: 20
<212> TYPE: DNA
<213> ORGANISM: Homo sapiens

<400> SEQUENCE: 327
acagagggag gaagcggggg                                              20

<210> SEQ ID NO 328
<211> LENGTH: 19
<212> TYPE: DNA
<213> ORGANISM: Homo sapiens

<400> SEQUENCE: 328
```

```
tggtcccggg tcctcccca                                          19

<210> SEQ ID NO 329
<211> LENGTH: 19
<212> TYPE: DNA
<213> ORGANISM: Homo sapiens

<400> SEQUENCE: 329
ggtcccgggt cctccccac                                          19

<210> SEQ ID NO 330
<211> LENGTH: 19
<212> TYPE: DNA
<213> ORGANISM: Homo sapiens

<400> SEQUENCE: 330
gtcccgggtc ctccccaca                                          19

<210> SEQ ID NO 331
<211> LENGTH: 19
<212> TYPE: DNA
<213> ORGANISM: Homo sapiens

<400> SEQUENCE: 331
tcccgggtcc tccccacag                                          19

<210> SEQ ID NO 332
<211> LENGTH: 19
<212> TYPE: DNA
<213> ORGANISM: Homo sapiens

<400> SEQUENCE: 332
cccgggtcct ccccacaga                                          19

<210> SEQ ID NO 333
<211> LENGTH: 19
<212> TYPE: DNA
<213> ORGANISM: Homo sapiens

<400> SEQUENCE: 333
ccgggtcctc cccacagag                                          19

<210> SEQ ID NO 334
<211> LENGTH: 19
<212> TYPE: DNA
<213> ORGANISM: Homo sapiens

<400> SEQUENCE: 334
cgggtcctcc ccacagagg                                          19

<210> SEQ ID NO 335
<211> LENGTH: 19
<212> TYPE: DNA
<213> ORGANISM: Homo sapiens

<400> SEQUENCE: 335
gggtcctccc cacagaggg                                          19

<210> SEQ ID NO 336
<211> LENGTH: 19
<212> TYPE: DNA
<213> ORGANISM: Homo sapiens

<400> SEQUENCE: 336
```
ggtcctcccc acagaggga 19

<210> SEQ ID NO 337
<211> LENGTH: 19
<212> TYPE: DNA
<213> ORGANISM: Homo sapiens

<400> SEQUENCE: 337
gtcctcccca cagagggag 19

<210> SEQ ID NO 338
<211> LENGTH: 19
<212> TYPE: DNA
<213> ORGANISM: Homo sapiens

<400> SEQUENCE: 338
tcctccccac agagggagg 19

<210> SEQ ID NO 339
<211> LENGTH: 19
<212> TYPE: DNA
<213> ORGANISM: Homo sapiens

<400> SEQUENCE: 339
cctccccaca gagggagga 19

<210> SEQ ID NO 340
<211> LENGTH: 19
<212> TYPE: DNA
<213> ORGANISM: Homo sapiens

<400> SEQUENCE: 340
ctccccacag agggaggaa 19

<210> SEQ ID NO 341
<211> LENGTH: 19
<212> TYPE: DNA
<213> ORGANISM: Homo sapiens

<400> SEQUENCE: 341
tccccacaga gggaggaag 19

<210> SEQ ID NO 342
<211> LENGTH: 19
<212> TYPE: DNA
<213> ORGANISM: Homo sapiens

<400> SEQUENCE: 342
ccccacagag ggaggaagc 19

<210> SEQ ID NO 343
<211> LENGTH: 19
<212> TYPE: DNA
<213> ORGANISM: Homo sapiens

<400> SEQUENCE: 343
cccacagagg gaggaagcg 19

<210> SEQ ID NO 344
<211> LENGTH: 19
<212> TYPE: DNA
<213> ORGANISM: Homo sapiens

```
<400> SEQUENCE: 344
ccacagaggg aggaagcgg                                          19

<210> SEQ ID NO 345
<211> LENGTH: 19
<212> TYPE: DNA
<213> ORGANISM: Homo sapiens

<400> SEQUENCE: 345
cacagaggga ggaagcggg                                          19

<210> SEQ ID NO 346
<211> LENGTH: 19
<212> TYPE: DNA
<213> ORGANISM: Homo sapiens

<400> SEQUENCE: 346
acagagggag gaagcgggg                                          19

<210> SEQ ID NO 347
<211> LENGTH: 18
<212> TYPE: DNA
<213> ORGANISM: Homo sapiens

<400> SEQUENCE: 347
ggtcccgggt cctcccca                                           18

<210> SEQ ID NO 348
<211> LENGTH: 18
<212> TYPE: DNA
<213> ORGANISM: Homo sapiens

<400> SEQUENCE: 348
gtcccgggtc ctccccac                                           18

<210> SEQ ID NO 349
<211> LENGTH: 18
<212> TYPE: DNA
<213> ORGANISM: Homo sapiens

<400> SEQUENCE: 349
tcccgggtcc tccccaca                                           18

<210> SEQ ID NO 350
<211> LENGTH: 18
<212> TYPE: DNA
<213> ORGANISM: Homo sapiens

<400> SEQUENCE: 350
cccgggtcct ccccacag                                           18

<210> SEQ ID NO 351
<211> LENGTH: 18
<212> TYPE: DNA
<213> ORGANISM: Homo sapiens

<400> SEQUENCE: 351
ccgggtcctc cccacaga                                           18

<210> SEQ ID NO 352
<211> LENGTH: 18
<212> TYPE: DNA
<213> ORGANISM: Homo sapiens
```

```
<400> SEQUENCE: 352
cgggtcctcc ccacagag                                                 18

<210> SEQ ID NO 353
<211> LENGTH: 18
<212> TYPE: DNA
<213> ORGANISM: Homo sapiens

<400> SEQUENCE: 353
gggtcctccc cacagagg                                                 18

<210> SEQ ID NO 354
<211> LENGTH: 18
<212> TYPE: DNA
<213> ORGANISM: Homo sapiens

<400> SEQUENCE: 354
ggtcctcccc acagaggg                                                 18

<210> SEQ ID NO 355
<211> LENGTH: 18
<212> TYPE: DNA
<213> ORGANISM: Homo sapiens

<400> SEQUENCE: 355
gtcctcccca cagaggga                                                 18

<210> SEQ ID NO 356
<211> LENGTH: 18
<212> TYPE: DNA
<213> ORGANISM: Homo sapiens

<400> SEQUENCE: 356
tcctccccac agagggag                                                 18

<210> SEQ ID NO 357
<211> LENGTH: 18
<212> TYPE: DNA
<213> ORGANISM: Homo sapiens

<400> SEQUENCE: 357
cctccccaca gagggagg                                                 18

<210> SEQ ID NO 358
<211> LENGTH: 18
<212> TYPE: DNA
<213> ORGANISM: Homo sapiens

<400> SEQUENCE: 358
ctccccacag agggagga                                                 18

<210> SEQ ID NO 359
<211> LENGTH: 18
<212> TYPE: DNA
<213> ORGANISM: Homo sapiens

<400> SEQUENCE: 359
tccccacaga gggaggaa                                                 18

<210> SEQ ID NO 360
<211> LENGTH: 18
<212> TYPE: DNA
```

```
<213> ORGANISM: Homo sapiens

<400> SEQUENCE: 360
ccccacagag ggaggaag                                                  18

<210> SEQ ID NO 361
<211> LENGTH: 18
<212> TYPE: DNA
<213> ORGANISM: Homo sapiens

<400> SEQUENCE: 361
cccacagagg gaggaagc                                                  18

<210> SEQ ID NO 362
<211> LENGTH: 18
<212> TYPE: DNA
<213> ORGANISM: Homo sapiens

<400> SEQUENCE: 362
ccacagaggg aggaagcg                                                  18

<210> SEQ ID NO 363
<211> LENGTH: 18
<212> TYPE: DNA
<213> ORGANISM: Homo sapiens

<400> SEQUENCE: 363
cacagaggga ggaagcgg                                                  18

<210> SEQ ID NO 364
<211> LENGTH: 18
<212> TYPE: DNA
<213> ORGANISM: Homo sapiens

<400> SEQUENCE: 364
acagagggag gaagcggg                                                  18

<210> SEQ ID NO 365
<211> LENGTH: 17
<212> TYPE: DNA
<213> ORGANISM: Homo sapiens

<400> SEQUENCE: 365
gtcccgggtc ctcccca                                                   17

<210> SEQ ID NO 366
<211> LENGTH: 17
<212> TYPE: DNA
<213> ORGANISM: Homo sapiens

<400> SEQUENCE: 366
tcccgggtcc tccccac                                                   17

<210> SEQ ID NO 367
<211> LENGTH: 17
<212> TYPE: DNA
<213> ORGANISM: Homo sapiens

<400> SEQUENCE: 367
cccgggtcct ccccaca                                                   17

<210> SEQ ID NO 368
<211> LENGTH: 17
```

<212> TYPE: DNA
<213> ORGANISM: Homo sapiens

<400> SEQUENCE: 368
ccgggtcctc cccacag                                                17

<210> SEQ ID NO 369
<211> LENGTH: 17
<212> TYPE: DNA
<213> ORGANISM: Homo sapiens

<400> SEQUENCE: 369
cgggtcctcc ccacaga                                                17

<210> SEQ ID NO 370
<211> LENGTH: 17
<212> TYPE: DNA
<213> ORGANISM: Homo sapiens

<400> SEQUENCE: 370
gggtcctccc cacagag                                                17

<210> SEQ ID NO 371
<211> LENGTH: 17
<212> TYPE: DNA
<213> ORGANISM: Homo sapiens

<400> SEQUENCE: 371
ggtcctcccc acagagg                                                17

<210> SEQ ID NO 372
<211> LENGTH: 17
<212> TYPE: DNA
<213> ORGANISM: Homo sapiens

<400> SEQUENCE: 372
gtcctcccca cagaggg                                                17

<210> SEQ ID NO 373
<211> LENGTH: 17
<212> TYPE: DNA
<213> ORGANISM: Homo sapiens

<400> SEQUENCE: 373
tcctccccac agaggga                                                17

<210> SEQ ID NO 374
<211> LENGTH: 17
<212> TYPE: DNA
<213> ORGANISM: Homo sapiens

<400> SEQUENCE: 374
cctccccaca gagggag                                                17

<210> SEQ ID NO 375
<211> LENGTH: 17
<212> TYPE: DNA
<213> ORGANISM: Homo sapiens

<400> SEQUENCE: 375
ctccccacag agggagg                                                17

<210> SEQ ID NO 376

```
<211> LENGTH: 17
<212> TYPE: DNA
<213> ORGANISM: Homo sapiens

<400> SEQUENCE: 376
tccccacaga gggagga                                                  17

<210> SEQ ID NO 377
<211> LENGTH: 17
<212> TYPE: DNA
<213> ORGANISM: Homo sapiens

<400> SEQUENCE: 377
ccccacagag ggaggaa                                                  17

<210> SEQ ID NO 378
<211> LENGTH: 17
<212> TYPE: DNA
<213> ORGANISM: Homo sapiens

<400> SEQUENCE: 378
cccacagagg gaggaag                                                  17

<210> SEQ ID NO 379
<211> LENGTH: 17
<212> TYPE: DNA
<213> ORGANISM: Homo sapiens

<400> SEQUENCE: 379
ccacagaggg aggaagc                                                  17

<210> SEQ ID NO 380
<211> LENGTH: 17
<212> TYPE: DNA
<213> ORGANISM: Homo sapiens

<400> SEQUENCE: 380
cacagaggga ggaagcg                                                  17

<210> SEQ ID NO 381
<211> LENGTH: 17
<212> TYPE: DNA
<213> ORGANISM: Homo sapiens

<400> SEQUENCE: 381
acagagggag gaagcgg                                                  17

<210> SEQ ID NO 382
<211> LENGTH: 16
<212> TYPE: DNA
<213> ORGANISM: Homo sapiens

<400> SEQUENCE: 382
tcccgggtcc tcccca                                                   16

<210> SEQ ID NO 383
<211> LENGTH: 16
<212> TYPE: DNA
<213> ORGANISM: Homo sapiens

<400> SEQUENCE: 383
cccgggtcct ccccac                                                   16
```

```
<210> SEQ ID NO 384
<211> LENGTH: 16
<212> TYPE: DNA
<213> ORGANISM: Homo sapiens

<400> SEQUENCE: 384
ccgggtcctc cccaca                                                   16

<210> SEQ ID NO 385
<211> LENGTH: 16
<212> TYPE: DNA
<213> ORGANISM: Homo sapiens

<400> SEQUENCE: 385
cgggtcctcc ccacag                                                   16

<210> SEQ ID NO 386
<211> LENGTH: 16
<212> TYPE: DNA
<213> ORGANISM: Homo sapiens

<400> SEQUENCE: 386
gggtcctccc cacaga                                                   16

<210> SEQ ID NO 387
<211> LENGTH: 16
<212> TYPE: DNA
<213> ORGANISM: Homo sapiens

<400> SEQUENCE: 387
ggtcctcccc acagag                                                   16

<210> SEQ ID NO 388
<211> LENGTH: 16
<212> TYPE: DNA
<213> ORGANISM: Homo sapiens

<400> SEQUENCE: 388
gtcctcccca cagagg                                                   16

<210> SEQ ID NO 389
<211> LENGTH: 16
<212> TYPE: DNA
<213> ORGANISM: Homo sapiens

<400> SEQUENCE: 389
tcctccccac agaggg                                                   16

<210> SEQ ID NO 390
<211> LENGTH: 16
<212> TYPE: DNA
<213> ORGANISM: Homo sapiens

<400> SEQUENCE: 390
cctccccaca gaggga                                                   16

<210> SEQ ID NO 391
<211> LENGTH: 16
<212> TYPE: DNA
<213> ORGANISM: Homo sapiens

<400> SEQUENCE: 391
ctccccacag agggag                                                   16
```

<210> SEQ ID NO 392
<211> LENGTH: 16
<212> TYPE: DNA
<213> ORGANISM: Homo sapiens

<400> SEQUENCE: 392
tccccacaga gggagg                                            16

<210> SEQ ID NO 393
<211> LENGTH: 16
<212> TYPE: DNA
<213> ORGANISM: Homo sapiens

<400> SEQUENCE: 393
ccccacagag ggagga                                            16

<210> SEQ ID NO 394
<211> LENGTH: 16
<212> TYPE: DNA
<213> ORGANISM: Homo sapiens

<400> SEQUENCE: 394
cccacagagg gaggaa                                            16

<210> SEQ ID NO 395
<211> LENGTH: 16
<212> TYPE: DNA
<213> ORGANISM: Homo sapiens

<400> SEQUENCE: 395
ccacagaggg aggaag                                            16

<210> SEQ ID NO 396
<211> LENGTH: 16
<212> TYPE: DNA
<213> ORGANISM: Homo sapiens

<400> SEQUENCE: 396
cacagaggga ggaagc                                            16

<210> SEQ ID NO 397
<211> LENGTH: 16
<212> TYPE: DNA
<213> ORGANISM: Homo sapiens

<400> SEQUENCE: 397
acagagggag gaagcg                                            16

<210> SEQ ID NO 398
<211> LENGTH: 15
<212> TYPE: DNA
<213> ORGANISM: Homo sapiens

<400> SEQUENCE: 398
cccgggtcct cccca                                             15

<210> SEQ ID NO 399
<211> LENGTH: 15
<212> TYPE: DNA
<213> ORGANISM: Homo sapiens

<400> SEQUENCE: 399
ccgggtcctc ccac                                              15

```
<210> SEQ ID NO 400
<211> LENGTH: 15
<212> TYPE: DNA
<213> ORGANISM: Homo sapiens

<400> SEQUENCE: 400
cgggtcctcc ccaca                                                    15

<210> SEQ ID NO 401
<211> LENGTH: 15
<212> TYPE: DNA
<213> ORGANISM: Homo sapiens

<400> SEQUENCE: 401
gggtcctccc cacag                                                    15

<210> SEQ ID NO 402
<211> LENGTH: 15
<212> TYPE: DNA
<213> ORGANISM: Homo sapiens

<400> SEQUENCE: 402
ggtcctcccc acaga                                                    15

<210> SEQ ID NO 403
<211> LENGTH: 15
<212> TYPE: DNA
<213> ORGANISM: Homo sapiens

<400> SEQUENCE: 403
gtcctcccca cagag                                                    15

<210> SEQ ID NO 404
<211> LENGTH: 15
<212> TYPE: DNA
<213> ORGANISM: Homo sapiens

<400> SEQUENCE: 404
tcctccccac agagg                                                    15

<210> SEQ ID NO 405
<211> LENGTH: 15
<212> TYPE: DNA
<213> ORGANISM: Homo sapiens

<400> SEQUENCE: 405
cctccccaca gaggg                                                    15

<210> SEQ ID NO 406
<211> LENGTH: 15
<212> TYPE: DNA
<213> ORGANISM: Homo sapiens

<400> SEQUENCE: 406
ctccccacag aggga                                                    15

<210> SEQ ID NO 407
<211> LENGTH: 15
<212> TYPE: DNA
<213> ORGANISM: Homo sapiens

<400> SEQUENCE: 407
```

```
tccccacaga gggag                                                    15

<210> SEQ ID NO 408
<211> LENGTH: 15
<212> TYPE: DNA
<213> ORGANISM: Homo sapiens

<400> SEQUENCE: 408
ccccacagag ggagg                                                    15

<210> SEQ ID NO 409
<211> LENGTH: 15
<212> TYPE: DNA
<213> ORGANISM: Homo sapiens

<400> SEQUENCE: 409
cccacagagg gagga                                                    15

<210> SEQ ID NO 410
<211> LENGTH: 15
<212> TYPE: DNA
<213> ORGANISM: Homo sapiens

<400> SEQUENCE: 410
ccacagaggg aggaa                                                    15

<210> SEQ ID NO 411
<211> LENGTH: 15
<212> TYPE: DNA
<213> ORGANISM: Homo sapiens

<400> SEQUENCE: 411
cacagaggga ggaag                                                    15

<210> SEQ ID NO 412
<211> LENGTH: 15
<212> TYPE: DNA
<213> ORGANISM: Homo sapiens

<400> SEQUENCE: 412
acagagggag gaagc                                                    15

<210> SEQ ID NO 413
<211> LENGTH: 20
<212> TYPE: DNA
<213> ORGANISM: Homo sapiens

<400> SEQUENCE: 413
gaaatggagt cctccccacc                                               20

<210> SEQ ID NO 414
<211> LENGTH: 20
<212> TYPE: DNA
<213> ORGANISM: Homo sapiens

<400> SEQUENCE: 414
aaatggagtc ctccccacct                                               20

<210> SEQ ID NO 415
<211> LENGTH: 20
<212> TYPE: DNA
<213> ORGANISM: Homo sapiens

<400> SEQUENCE: 415
```

```
aatggagtcc tccccacctc                                              20

<210> SEQ ID NO 416
<211> LENGTH: 20
<212> TYPE: DNA
<213> ORGANISM: Homo sapiens

<400> SEQUENCE: 416
atggagtcct ccccacctcc                                              20

<210> SEQ ID NO 417
<211> LENGTH: 20
<212> TYPE: DNA
<213> ORGANISM: Homo sapiens

<400> SEQUENCE: 417
tggagtcctc cccacctccc                                              20

<210> SEQ ID NO 418
<211> LENGTH: 20
<212> TYPE: DNA
<213> ORGANISM: Homo sapiens

<400> SEQUENCE: 418
ggagtcctcc ccacctcccg                                              20

<210> SEQ ID NO 419
<211> LENGTH: 20
<212> TYPE: DNA
<213> ORGANISM: Homo sapiens

<400> SEQUENCE: 419
gagtcctccc cacctcccgg                                              20

<210> SEQ ID NO 420
<211> LENGTH: 20
<212> TYPE: DNA
<213> ORGANISM: Homo sapiens

<400> SEQUENCE: 420
agtcctcccc acctcccggc                                              20

<210> SEQ ID NO 421
<211> LENGTH: 20
<212> TYPE: DNA
<213> ORGANISM: Homo sapiens

<400> SEQUENCE: 421
gtcctcccca cctcccggcc                                              20

<210> SEQ ID NO 422
<211> LENGTH: 20
<212> TYPE: DNA
<213> ORGANISM: Homo sapiens

<400> SEQUENCE: 422
tcctccccac ctcccggccc                                              20

<210> SEQ ID NO 423
<211> LENGTH: 20
<212> TYPE: DNA
<213> ORGANISM: Homo sapiens
```

<400> SEQUENCE: 423
cctccccacc tcccggcccc                                                   20

<210> SEQ ID NO 424
<211> LENGTH: 20
<212> TYPE: DNA
<213> ORGANISM: Homo sapiens

<400> SEQUENCE: 424
ctccccacct cccggcccca                                                   20

<210> SEQ ID NO 425
<211> LENGTH: 20
<212> TYPE: DNA
<213> ORGANISM: Homo sapiens

<400> SEQUENCE: 425
tccccacctc ccggccccat                                                   20

<210> SEQ ID NO 426
<211> LENGTH: 20
<212> TYPE: DNA
<213> ORGANISM: Homo sapiens

<400> SEQUENCE: 426
ccccacctcc cggccccatt                                                   20

<210> SEQ ID NO 427
<211> LENGTH: 20
<212> TYPE: DNA
<213> ORGANISM: Homo sapiens

<400> SEQUENCE: 427
cccacctccc ggccccattc                                                   20

<210> SEQ ID NO 428
<211> LENGTH: 20
<212> TYPE: DNA
<213> ORGANISM: Homo sapiens

<400> SEQUENCE: 428
ccacctcccg gccccattca                                                   20

<210> SEQ ID NO 429
<211> LENGTH: 20
<212> TYPE: DNA
<213> ORGANISM: Homo sapiens

<400> SEQUENCE: 429
cacctcccgg ccccattcag                                                   20

<210> SEQ ID NO 430
<211> LENGTH: 20
<212> TYPE: DNA
<213> ORGANISM: Homo sapiens

<400> SEQUENCE: 430
acctcccggc cccattcaga                                                   20

<210> SEQ ID NO 431
<211> LENGTH: 20
<212> TYPE: DNA
<213> ORGANISM: Homo sapiens

```
<400> SEQUENCE: 431
cctcccggcc ccattcagag                                              20

<210> SEQ ID NO 432
<211> LENGTH: 20
<212> TYPE: DNA
<213> ORGANISM: Homo sapiens

<400> SEQUENCE: 432
ctcccggccc cattcagagt                                              20

<210> SEQ ID NO 433
<211> LENGTH: 19
<212> TYPE: DNA
<213> ORGANISM: Homo sapiens

<400> SEQUENCE: 433
aaatggagtc ctccccacc                                               19

<210> SEQ ID NO 434
<211> LENGTH: 19
<212> TYPE: DNA
<213> ORGANISM: Homo sapiens

<400> SEQUENCE: 434
aatggagtcc tccccacct                                               19

<210> SEQ ID NO 435
<211> LENGTH: 19
<212> TYPE: DNA
<213> ORGANISM: Homo sapiens

<400> SEQUENCE: 435
atggagtcct ccccacctc                                               19

<210> SEQ ID NO 436
<211> LENGTH: 19
<212> TYPE: DNA
<213> ORGANISM: Homo sapiens

<400> SEQUENCE: 436
tggagtcctc cccacctcc                                               19

<210> SEQ ID NO 437
<211> LENGTH: 19
<212> TYPE: DNA
<213> ORGANISM: Homo sapiens

<400> SEQUENCE: 437
ggagtcctcc ccacctccc                                               19

<210> SEQ ID NO 438
<211> LENGTH: 19
<212> TYPE: DNA
<213> ORGANISM: Homo sapiens

<400> SEQUENCE: 438
gagtcctccc cacctcccg                                               19

<210> SEQ ID NO 439
<211> LENGTH: 19
<212> TYPE: DNA
```

<213> ORGANISM: Homo sapiens

<400> SEQUENCE: 439
agtcctcccc acctcccgg					19

<210> SEQ ID NO 440
<211> LENGTH: 19
<212> TYPE: DNA
<213> ORGANISM: Homo sapiens

<400> SEQUENCE: 440
gtcctcccca cctcccggc					19

<210> SEQ ID NO 441
<211> LENGTH: 19
<212> TYPE: DNA
<213> ORGANISM: Homo sapiens

<400> SEQUENCE: 441 tcctcccac ctcccggcc					19

<210> SEQ ID NO 442
<211> LENGTH: 19
<212> TYPE: DNA
<213> ORGANISM: Homo sapiens

<400> SEQUENCE: 442
cctccccacc tcccggccc					19

<210> SEQ ID NO 443
<211> LENGTH: 19
<212> TYPE: DNA
<213> ORGANISM: Homo sapiens

<400> SEQUENCE: 443
ctccccacct cccggcccc					19

<210> SEQ ID NO 444
<211> LENGTH: 19
<212> TYPE: DNA
<213> ORGANISM: Homo sapiens

<400> SEQUENCE: 444
tccccacctc ccggcccca					19

<210> SEQ ID NO 445
<211> LENGTH: 19
<212> TYPE: DNA
<213> ORGANISM: Homo sapiens

<400> SEQUENCE: 445
ccccacctcc cggcccat					19

<210> SEQ ID NO 446
<211> LENGTH: 19
<212> TYPE: DNA
<213> ORGANISM: Homo sapiens

<400> SEQUENCE: 446
cccacctccc ggcccatt					19

<210> SEQ ID NO 447
<211> LENGTH: 19

<212> TYPE: DNA
<213> ORGANISM: Homo sapiens

<400> SEQUENCE: 447
ccacctcccg gccccattc                                           19

<210> SEQ ID NO 448
<211> LENGTH: 19
<212> TYPE: DNA
<213> ORGANISM: Homo sapiens

<400> SEQUENCE: 448
cacctcccgg ccccattca                                           19

<210> SEQ ID NO 449
<211> LENGTH: 19
<212> TYPE: DNA
<213> ORGANISM: Homo sapiens

<400> SEQUENCE: 449
acctcccggc cccattcag                                           19

<210> SEQ ID NO 450
<211> LENGTH: 19
<212> TYPE: DNA
<213> ORGANISM: Homo sapiens

<400> SEQUENCE: 450
cctcccggcc ccattcaga                                           19

<210> SEQ ID NO 451
<211> LENGTH: 19
<212> TYPE: DNA
<213> ORGANISM: Homo sapiens

<400> SEQUENCE: 451
ctcccggccc cattcagag                                           19

<210> SEQ ID NO 452
<211> LENGTH: 18
<212> TYPE: DNA
<213> ORGANISM: Homo sapiens

<400> SEQUENCE: 452
aatggagtcc tccccacc                                            18

<210> SEQ ID NO 453
<211> LENGTH: 18
<212> TYPE: DNA
<213> ORGANISM: Homo sapiens

<400> SEQUENCE: 453
atggagtcct ccccacct                                            18

<210> SEQ ID NO 454
<211> LENGTH: 18
<212> TYPE: DNA
<213> ORGANISM: Homo sapiens

<400> SEQUENCE: 454
tggagtcctc cccacctc                                            18

<210> SEQ ID NO 455

```
<211> LENGTH: 18
<212> TYPE: DNA
<213> ORGANISM: Homo sapiens

<400> SEQUENCE: 455
ggagtcctcc ccacctcc                                                18

<210> SEQ ID NO 456
<211> LENGTH: 18
<212> TYPE: DNA
<213> ORGANISM: Homo sapiens

<400> SEQUENCE: 456
gagtcctccc cacctccc                                                18

<210> SEQ ID NO 457
<211> LENGTH: 18
<212> TYPE: DNA
<213> ORGANISM: Homo sapiens

<400> SEQUENCE: 457
agtcctcccc acctcccg                                                18

<210> SEQ ID NO 458
<211> LENGTH: 18
<212> TYPE: DNA
<213> ORGANISM: Homo sapiens

<400> SEQUENCE: 458
gtcctcccca cctcccgg                                                18

<210> SEQ ID NO 459
<211> LENGTH: 18
<212> TYPE: DNA
<213> ORGANISM: Homo sapiens

<400> SEQUENCE: 459
tcctccccac ctcccggc                                                18

<210> SEQ ID NO 460
<211> LENGTH: 18
<212> TYPE: DNA
<213> ORGANISM: Homo sapiens

<400> SEQUENCE: 460
cctccccacc tcccggcc                                                18

<210> SEQ ID NO 461
<211> LENGTH: 18
<212> TYPE: DNA
<213> ORGANISM: Homo sapiens

<400> SEQUENCE: 461
ctccccacct cccggccc                                                18

<210> SEQ ID NO 462
<211> LENGTH: 18
<212> TYPE: DNA
<213> ORGANISM: Homo sapiens

<400> SEQUENCE: 462
tccccacctc ccggcccc                                                18
```

-continued

```
<210> SEQ ID NO 463
<211> LENGTH: 18
<212> TYPE: DNA
<213> ORGANISM: Homo sapiens

<400> SEQUENCE: 463
ccccacctcc cggcccca                                                 18

<210> SEQ ID NO 464
<211> LENGTH: 18
<212> TYPE: DNA
<213> ORGANISM: Homo sapiens

<400> SEQUENCE: 464
cccacctccc ggccccat                                                 18

<210> SEQ ID NO 465
<211> LENGTH: 18
<212> TYPE: DNA
<213> ORGANISM: Homo sapiens

<400> SEQUENCE: 465
ccacctcccg gccccatt                                                 18

<210> SEQ ID NO 466
<211> LENGTH: 18
<212> TYPE: DNA
<213> ORGANISM: Homo sapiens

<400> SEQUENCE: 466
cacctcccgg ccccattc                                                 18

<210> SEQ ID NO 467
<211> LENGTH: 18
<212> TYPE: DNA
<213> ORGANISM: Homo sapiens

<400> SEQUENCE: 467
acctcccggc cccattca                                                 18

<210> SEQ ID NO 468
<211> LENGTH: 18
<212> TYPE: DNA
<213> ORGANISM: Homo sapiens

<400> SEQUENCE: 468
cctcccggcc ccattcag                                                 18

<210> SEQ ID NO 469
<211> LENGTH: 18
<212> TYPE: DNA
<213> ORGANISM: Homo sapiens

<400> SEQUENCE: 469
ctcccggccc cattcaga                                                 18

<210> SEQ ID NO 470
<211> LENGTH: 17
<212> TYPE: DNA
<213> ORGANISM: Homo sapiens

<400> SEQUENCE: 470
atggagtcct ccccacc                                                  17
```

```
<210> SEQ ID NO 471
<211> LENGTH: 17
<212> TYPE: DNA
<213> ORGANISM: Homo sapiens

<400> SEQUENCE: 471
tggagtcctc cccacct                                                   17

<210> SEQ ID NO 472
<211> LENGTH: 17
<212> TYPE: DNA
<213> ORGANISM: Homo sapiens

<400> SEQUENCE: 472
ggagtcctcc ccacctc                                                   17

<210> SEQ ID NO 473
<211> LENGTH: 17
<212> TYPE: DNA
<213> ORGANISM: Homo sapiens

<400> SEQUENCE: 473
gagtcctccc cacctcc                                                   17

<210> SEQ ID NO 474
<211> LENGTH: 17
<212> TYPE: DNA
<213> ORGANISM: Homo sapiens

<400> SEQUENCE: 474
agtcctcccc acctccc                                                   17

<210> SEQ ID NO 475
<211> LENGTH: 17
<212> TYPE: DNA
<213> ORGANISM: Homo sapiens

<400> SEQUENCE: 475
gtcctcccca cctcccg                                                   17

<210> SEQ ID NO 476
<211> LENGTH: 17
<212> TYPE: DNA
<213> ORGANISM: Homo sapiens

<400> SEQUENCE: 476
tcctccccac ctcccgg                                                   17

<210> SEQ ID NO 477
<211> LENGTH: 17
<212> TYPE: DNA
<213> ORGANISM: Homo sapiens

<400> SEQUENCE: 477
cctccccacc tcccggc                                                   17

<210> SEQ ID NO 478
<211> LENGTH: 17
<212> TYPE: DNA
<213> ORGANISM: Homo sapiens

<400> SEQUENCE: 478
ctccccacct cccggcc                                                   17
```

```
<210> SEQ ID NO 479
<211> LENGTH: 17
<212> TYPE: DNA
<213> ORGANISM: Homo sapiens

<400> SEQUENCE: 479
tccccacctc ccggccc                                                    17

<210> SEQ ID NO 480
<211> LENGTH: 17
<212> TYPE: DNA
<213> ORGANISM: Homo sapiens

<400> SEQUENCE: 480
ccccacctcc cggcccc                                                    17

<210> SEQ ID NO 481
<211> LENGTH: 17
<212> TYPE: DNA
<213> ORGANISM: Homo sapiens

<400> SEQUENCE: 481
cccacctccc ggcccca                                                    17

<210> SEQ ID NO 482
<211> LENGTH: 17
<212> TYPE: DNA
<213> ORGANISM: Homo sapiens

<400> SEQUENCE: 482
ccacctcccg gccccat                                                    17

<210> SEQ ID NO 483
<211> LENGTH: 17
<212> TYPE: DNA
<213> ORGANISM: Homo sapiens

<400> SEQUENCE: 483
cacctcccgg ccccatt                                                    17

<210> SEQ ID NO 484
<211> LENGTH: 17
<212> TYPE: DNA
<213> ORGANISM: Homo sapiens

<400> SEQUENCE: 484
acctcccggc cccattc                                                    17

<210> SEQ ID NO 485
<211> LENGTH: 17
<212> TYPE: DNA
<213> ORGANISM: Homo sapiens

<400> SEQUENCE: 485
cctcccggcc ccattca                                                    17

<210> SEQ ID NO 486
<211> LENGTH: 17
<212> TYPE: DNA
<213> ORGANISM: Homo sapiens

<400> SEQUENCE: 486
```

```
ctcccggccc cattcag                                                    17

<210> SEQ ID NO 487
<211> LENGTH: 16
<212> TYPE: DNA
<213> ORGANISM: Homo sapiens

<400> SEQUENCE: 487
tggagtcctc cccacc                                                     16

<210> SEQ ID NO 488
<211> LENGTH: 16
<212> TYPE: DNA
<213> ORGANISM: Homo sapiens

<400> SEQUENCE: 488
ggagtcctcc ccacct                                                     16

<210> SEQ ID NO 489
<211> LENGTH: 16
<212> TYPE: DNA
<213> ORGANISM: Homo sapiens

<400> SEQUENCE: 489
gagtcctccc cacctc                                                     16

<210> SEQ ID NO 490
<211> LENGTH: 16
<212> TYPE: DNA
<213> ORGANISM: Homo sapiens

<400> SEQUENCE: 490
agtcctcccc acctcc                                                     16

<210> SEQ ID NO 491
<211> LENGTH: 16
<212> TYPE: DNA
<213> ORGANISM: Homo sapiens

<400> SEQUENCE: 491
gtcctcccca cctccc                                                     16

<210> SEQ ID NO 492
<211> LENGTH: 16
<212> TYPE: DNA
<213> ORGANISM: Homo sapiens

<400> SEQUENCE: 492
tcctccccac ctcccg                                                     16

<210> SEQ ID NO 493
<211> LENGTH: 16
<212> TYPE: DNA
<213> ORGANISM: Homo sapiens

<400> SEQUENCE: 493
cctccccacc tcccgg                                                     16

<210> SEQ ID NO 494
<211> LENGTH: 16
<212> TYPE: DNA
<213> ORGANISM: Homo sapiens

<400> SEQUENCE: 494
```
ctccccacct cccggc                                                    16

<210> SEQ ID NO 495
<211> LENGTH: 16
<212> TYPE: DNA
<213> ORGANISM: Homo sapiens

<400> SEQUENCE: 495
tccccacctc ccggcc                                                    16

<210> SEQ ID NO 496
<211> LENGTH: 16
<212> TYPE: DNA
<213> ORGANISM: Homo sapiens

<400> SEQUENCE: 496
ccccacctcc cggccc                                                    16

<210> SEQ ID NO 497
<211> LENGTH: 16
<212> TYPE: DNA
<213> ORGANISM: Homo sapiens

<400> SEQUENCE: 497
cccacctccc ggcccc                                                    16

<210> SEQ ID NO 498
<211> LENGTH: 16
<212> TYPE: DNA
<213> ORGANISM: Homo sapiens

<400> SEQUENCE: 498
ccacctcccg gcccca                                                    16

<210> SEQ ID NO 499
<211> LENGTH: 16
<212> TYPE: DNA
<213> ORGANISM: Homo sapiens

<400> SEQUENCE: 499
cacctcccgg ccccat                                                    16

<210> SEQ ID NO 500
<211> LENGTH: 16
<212> TYPE: DNA
<213> ORGANISM: Homo sapiens

<400> SEQUENCE: 500
acctcccggc cccatt                                                    16

<210> SEQ ID NO 501
<211> LENGTH: 16
<212> TYPE: DNA
<213> ORGANISM: Homo sapiens

<400> SEQUENCE: 501
cctcccggcc ccattc                                                    16

<210> SEQ ID NO 502
<211> LENGTH: 16
<212> TYPE: DNA
<213> ORGANISM: Homo sapiens

```
<400> SEQUENCE: 502
ctcccggccc cattca                                                16

<210> SEQ ID NO 503
<211> LENGTH: 15
<212> TYPE: DNA
<213> ORGANISM: Homo sapiens

<400> SEQUENCE: 503
ggagtcctcc ccacc                                                 15

<210> SEQ ID NO 504
<211> LENGTH: 15
<212> TYPE: DNA
<213> ORGANISM: Homo sapiens

<400> SEQUENCE: 504
gagtcctccc cacct                                                 15

<210> SEQ ID NO 505
<211> LENGTH: 15
<212> TYPE: DNA
<213> ORGANISM: Homo sapiens

<400> SEQUENCE: 505
agtcctcccc acctc                                                 15

<210> SEQ ID NO 506
<211> LENGTH: 15
<212> TYPE: DNA
<213> ORGANISM: Homo sapiens

<400> SEQUENCE: 506
gtcctcccca cctcc                                                 15

<210> SEQ ID NO 507
<211> LENGTH: 15
<212> TYPE: DNA
<213> ORGANISM: Homo sapiens

<400> SEQUENCE: 507
tcctccccac ctccc                                                 15

<210> SEQ ID NO 508
<211> LENGTH: 15
<212> TYPE: DNA
<213> ORGANISM: Homo sapiens

<400> SEQUENCE: 508
cctccccacc tcccg                                                 15

<210> SEQ ID NO 509
<211> LENGTH: 15
<212> TYPE: DNA
<213> ORGANISM: Homo sapiens

<400> SEQUENCE: 509
ctccccacct cccgg                                                 15

<210> SEQ ID NO 510
<211> LENGTH: 15
<212> TYPE: DNA
<213> ORGANISM: Homo sapiens
```

<400> SEQUENCE: 510
tccccacctc ccggc                                                    15

<210> SEQ ID NO 511
<211> LENGTH: 15
<212> TYPE: DNA
<213> ORGANISM: Homo sapiens

<400> SEQUENCE: 511
ccccacctcc cggcc                                                    15

<210> SEQ ID NO 512
<211> LENGTH: 15
<212> TYPE: DNA
<213> ORGANISM: Homo sapiens

<400> SEQUENCE: 512
cccacctccc ggccc                                                    15

<210> SEQ ID NO 513
<211> LENGTH: 15
<212> TYPE: DNA
<213> ORGANISM: Homo sapiens

<400> SEQUENCE: 513
ccacctcccg gcccc                                                    15

<210> SEQ ID NO 514
<211> LENGTH: 15
<212> TYPE: DNA
<213> ORGANISM: Homo sapiens

<400> SEQUENCE: 514
cacctcccgg cccca                                                    15

<210> SEQ ID NO 515
<211> LENGTH: 15
<212> TYPE: DNA
<213> ORGANISM: Homo sapiens

<400> SEQUENCE: 515
acctcccggc cccat                                                    15

<210> SEQ ID NO 516
<211> LENGTH: 15
<212> TYPE: DNA
<213> ORGANISM: Homo sapiens

<400> SEQUENCE: 516
cctcccggcc ccatt                                                    15

<210> SEQ ID NO 517
<211> LENGTH: 15
<212> TYPE: DNA
<213> ORGANISM: Homo sapiens

<400> SEQUENCE: 517
ctcccggccc cattc                                                    15

<210> SEQ ID NO 518
<211> LENGTH: 22
<212> TYPE: DNA

<213> ORGANISM: Homo sapiens

<400> SEQUENCE: 518
gctggggaac agcatcacac cc    22

<210> SEQ ID NO 519
<211> LENGTH: 22
<212> TYPE: DNA
<213> ORGANISM: Homo sapiens

<400> SEQUENCE: 519
cctggagttg actggagact tg    22

<210> SEQ ID NO 520
<211> LENGTH: 20
<212> TYPE: DNA
<213> ORGANISM: Homo sapiens

<400> SEQUENCE: 520
gaggattgac cacaccacct    20

<210> SEQ ID NO 521
<211> LENGTH: 21
<212> TYPE: DNA
<213> ORGANISM: Homo sapiens

<400> SEQUENCE: 521
atgtggccat ttgacacgat a    21

<210> SEQ ID NO 522
<211> LENGTH: 50
<212> TYPE: DNA
<213> ORGANISM: Homo sapiens

<400> SEQUENCE: 522
tgacagttgt atttttgttt gtgacacgta ttatctgtta aaacattttc    50

<210> SEQ ID NO 523
<211> LENGTH: 61
<212> TYPE: DNA
<213> ORGANISM: Homo sapiens

<400> SEQUENCE: 523
tcttaaactt ttaaatgcca tttgatcttt gaaaatatat gttttaatag tgtattttaa    60
g    61

<210> SEQ ID NO 524
<211> LENGTH: 61
<212> TYPE: DNA
<213> ORGANISM: Homo sapiens

<400> SEQUENCE: 524
ccctcagcga gcaagtcaag ctcttcacag tgatgtctta caagcgcaga gggctctgtg    60
a    61

<210> SEQ ID NO 525
<211> LENGTH: 61
<212> TYPE: DNA
<213> ORGANISM: Homo sapiens

<400> SEQUENCE: 525
gctttgtccc tcccccgctt cctccctctg tggggaggac ccgggaccac agctgctggc    60

```
c                                                                61

<210> SEQ ID NO 526
<211> LENGTH: 61
<212> TYPE: DNA
<213> ORGANISM: Homo sapiens

<400> SEQUENCE: 526
ggagagactc cactctgaat ggggccggga ggtggggagg actccatttc agatggggtc    60
g                                                                61

<210> SEQ ID NO 527
<211> LENGTH: 54
<212> TYPE: DNA
<213> ORGANISM: Homo sapiens

<400> SEQUENCE: 527
tgacagttgt attttgttt gtgacactta cgtattatct gttaaaacat tttc            54
```